US006869770B1

(12) United States Patent
Roberts et al.

(10) Patent No.: US 6,869,770 B1
(45) Date of Patent: Mar. 22, 2005

(54) COMPOSITIONS AND METHODS FOR EARLY PREGNANCY DIAGNOSIS

(75) Inventors: Robert Michael Roberts, Columbia, MO (US); Jonathan Andrew Green, Columbia, MO (US); Sancai Xie, West Chester, OH (US)

(73) Assignee: The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 09/273,164

(22) Filed: Mar. 19, 1999

Related U.S. Application Data

(60) Provisional application No. 60/078,783, filed on Mar. 20, 1998, and provisional application No. 60/106,188, filed on Oct. 28, 1998.

(51) Int. Cl.$^7$ ................................................ G01N 33/53
(52) U.S. Cl. ........................ 435/7.1; 435/7.21; 435/7.4; 435/7.92; 435/7.95; 435/973; 436/514; 436/528; 436/530; 436/531; 436/161; 436/164; 424/1; 424/12
(58) Field of Search .......................... 424/1, 12; 435/7, 435/7.1, 7.92, 7.21, 7.4, 4, 5, 7.9, 7.95, 7.94, 970, 973, 975, 13, 969; 436/514, 528, 530, 531, 161, 164, 807, 808, 810, 811, 975

(56) References Cited

U.S. PATENT DOCUMENTS 4,271,140 A * 6/1981 Bunting .......................... 424/1

FOREIGN PATENT DOCUMENTS

WO         99/06038       2/1999   .......... A61K/31/19

OTHER PUBLICATIONS

Scott et al., Serum levels of pregnancy associated alpha2–glycoprotein during pregnancy in autoimmune thyroid disease: relationship to disease activity. Clinical and Experimental Immunology, 1985, 59, 564–570.*
Gerrie et al., Pregnancy–associated alpha2–glycoprotein:development of a sensitive enzyme–linked immunoassay and comparison of serum concentrations in adults and children. Clinical Chimica. Acta. 155, 51–60, 1986.*
Roberts et al., Glycoproteins of aspartyl proteinase gene family secreted by the developing placenta., Asprtic Prot., Struct., Funct., Biol., Biom. Impl., 231–240, 1995.*
Zoli et al., Radioimmunoassay of bovine pregnancy–associated glycoprotein, Biology and Reproduction., 45:1–10, 1991.*
Xie et al., Nov. 1997. Proc. Natl. Acad. Sci. USA., vol. 94., p. 12809–12816, Biochemistry.*
Sasser et al., Characteristics of pregnancy–specific protein B in cattle., J. Reprod. Fert., Suppl. 37, 1989, p. 109–113.*

Garabayo et al., "Caprine pregnancy–associated glycoproteins (PAG): Their cloning expression and evolutionary relationship to other PAG," Mo. Reprod Dev, 57:311–322, 2000.

Green et al., "Bovine pregnancy–associated glycoproteins (PAG) exhibit distinct expression patterns during gestation," Biol Reprod, 60(Suppl 1):497, 1999.

Green et al., "Identification of a family of Kunitz domain proteins expressed in bovine and ovine trophoblast," Biol Reprod, 58 (Suppl 1):310.

Green et al., Pregnancy–associated glycoprotein exhibit spatially and temporally distinct expression patterns during pregnancy., Bio. Reprod, 62:1624–1631, 2000.

Green et al., "Pregnancy–associated glycoproteins of the horse," Biol Reprod, 50 (Suppl 1):152, 1994.

Green et al., "Pregnancy–associated glycoproteins: A family of catalytically inactive aspartic proteinases," Mol Biol Cell, 6 (Suppl 1):454, 1995.

Green et al., "The establishment for an ELISA for the detection of pregnancy–associated glycoprotieins (PAGs) in the serum of pregnant cows and heifers," Departments of Animal Sciences and Biochemistry, University of Missouri–Columbia.

Ishiwata et al., "Characterization of gene expression profiles in early bovine pregnancy using a custom cDNA microarray," Mol Reprod Dev., 65(1):9–18, 2003.

Szafranska et al., "The genes for porcine and bovine pregnancy–associated glycoprotein 2: Its structural organization and analysis of its promoter," Mol. Reprod. De.v, 66:137–146, 2001.

Hughes et al., "Adaptive diversification within a large family of recently duplicated, placentally expressed genes," PNAS, 97:3319–3323, 2000.

(List continued on next page.)

Primary Examiner—Long V. Le
Assistant Examiner—Changhwa J. Cheu
(74) Attorney, Agent, or Firm—Fulbright & Jaworski L.L.P.

(57) ABSTRACT

Pregnancy-associated glycoproteins (PAGs) are structurally related to the pepsins, thought to be restricted to the hoofed (ungulate) mammals and characterized by being expressed specifically in the outer epithelial cell layer (chorion/trophectoderm) of the placenta. By cloning expressed genes from ovine and bovine placental cDNA libraries, the inventors estimate that cattle, sheep, and most probably all ruminant Artiodactyla, possess possibly 100 or more PAG genes, many of which are placentally expressed. The PAGs are highly diverse in sequence, with regions of hypervariability confined largely to surface-exposed loops. Selected PAG that are products of the iOnvasive binucleate cells, expressed highly in early pregnancy at the time of trophoblast invasion and expressed weakly, if at all, in late gestation are useful in the early diagnosis of pregnancy. In a preferred embodiment, the invention relates to immunoassays for detecting these PAGs.

24 Claims, 12 Drawing Sheets

OTHER PUBLICATIONS

Green et al., "Pregnancy–associated bovine and ovine glycoproteins exhibit spatially and temporally distinct expression patterns during pregnancy," *Bio. Of Repro.*, 62:1624–1631, 2000.

Atkinson et al., "Characterization of placentation–specific binucleate cell glycoproteins possessing a novel carbohydrate", *J. Biol. Chem.*, 268(35):26679–26685, 1993.

Birch and Loh, "Homology Cloning of Aspartic Proteases from an Endocrine Cell Line Using the Polymerase Chain Reaction," *Biochem. Biophys. Res. Commun.*, 177(3):920–926, 1991.

Cameron and Malmo, "Evaluation of an ultrasonic Doppler probe for pregnancy diagnosis in cattle," *Austr. Vet. J.*, 70:109–111, 1993.

Davies, "The structure and function of the aspartic proteinases," *Ann. Rev. Bioiphys. Chem.*, 19:189–215, 1990.

Green, et al., "Identification of a New Aspartic Proteinase Expressed by the Outer Chorionic Cell Layer of the Equine Placenta," *Bio. Reprod.*, 60:1069–1077, 1999.

Guillomot, "Cellular interactions during implantation in domestic ruminants," *J. Reprod. Fertil.*, 49(Suppl):39–51, 1995.

Guruprasad et al., "Comparative modelling and analysis of amino acid substitutions suggests that the family of pregnancy–associated glycoproteins includes both active and inactive aspartic proteinases," *Protein Engin.*, 9:849–856, 1996.

Haig, "Genetic Conflicts in Human Pregnancy," *Rev. Biol.*, 68:495–532, 1993.

Inoue, et al., "*Aspergillus niger* Var. Macrosporus Proteinase B. cDNA Cloning, Expression, and Activation of the Proenzyme," *Aspartic Proteinases*, 581–587, 1995.

King et al., "Development of the bovine placentome from days 20 to 29 of gestation," *J. Reprod. Fertil.*, 59:95–100, 1980.

Kiracofe et al., "Pregnancy–Specific Protein B in Serum of Postpartum Beef Cows," *J. Anim. Sci.*, 71:2199–2205, 1993.

Li et al., "Mutational analysis of the vesicular stomatitis virus glycoprotein G for membrane fusion domains," *J. Virol.*, 67(7):4070–4077, 1993.

Mialon et al., "Peripheral concentrations of a 60–kDa pregnancy serum protein during gestation and after calving and in relationship to embryonic mortality in cattle," *Reprod. Nutr. Dev.*, 33:269–282, 1993.

Mialon et al., "Detection of pregnancy by radioimmunoassay of a pregnancy serum protein (PSP60) in cattle," *Reprod. Nutr. Dev.*, 34:65–72, 1994.

Patel et al., "Effect of Fetal Mass, Number and Stage of Gestation on Pregnancy–Specific Protein B Concentrations in the Bovine," *Theriogenol.*, 44:827–833, 1995.

Patel, et al., Plasma bovine pregnancy–associated glycoprotein concentrations throughout gestation in relationship to fetal number in the cow, *Eur. J. Endoc.*, 137: 423–428, 1997.

Roberts, et al., "Glycoproteins of the aspartyl proteinase gene family secreted by the developing placenta," *Aspartic Prot., Struct., Funct., Biol., Biom. Impl.*, 231–240, 1995.

Roberts et al., "Maternal Recognition of Pregnancy," *Biol. Reprod.*, 54:294–302, 1996.

Roberts et al., "New and Atypical Families of Type I Interferons in Mammals: Comparative Functions, Structures, and Evolutionary Relationships," *Prog. Nucl. Acid Res. Mol. Biol.*, 56:287–326, 1997.

Sasser et al., "Detection of pregacy by radioimmunoassay of a novel pregnancy–specific protein in serum of cows and a profile of serum concentrations during gestation," *Biol. Reprod.*, 35:936–942, 1986.

Sasser et al., "Characteristics of pregnancy–specific protein B in cattle," *J. Reprod. Fertil.*, 37(Suppl):109–113, 1989.

Szafranska et al., Porcine Pregnancy–Associated Glycoproteins: New Members of the Aspartic Proteinase Gene Family Expressed in Trophectoderm, *Biol. Reprod.*, 53:21–28, 1995.

Szenci, et al., "Evaluation of false ultrasonographic diagnoses in cows by measuring plasma levels of bovine pregnancy–associated glycoprotein 1," *Vet. Record*, 304–306.

Wedemayer, "Structural Insights into the Evolution of an Antibody Combining Site," *Science*, 276(5319):1665–1669, 1997.

Wooding, "Current topic: the synepitheliochorial placenta of ruminants: binucleate cell fusions and hormone production," *Placenta*, 13:101–113, 1992.

Xie et al., "Identification of the major pregnancy–specific antigens of cattle and sheep as inactive members of the aspartic proteinase family," *Proc. Nat'l Acad. Sci. USA*, 88: 10247–10251, 1991.

Xie et al., "A novel glycoprotein of the aspartic proteinase gene family expressed in bovine placental trophectoderm," *Biol. Reprod.*, 51:1145–1153, 1994.

Xie et al., "The gene encoding bovine pregnancy–associated glycoprotein–1, an inactive member of the aspartic proteinase family," *Gene*, 159:193–197, 1995.

Xie et al., Trophoblast–specific processing and phosphorylation of pregnancy–associated glycoprotein–1 in day 15 to 25 sheep placenta, *Biol. Reprod.*, 54: 122–129, 1996.

Xie, et al., "The diversity of evolutionary relationships of the pregnancy–associated glycoproteins, as aspartic proteinase subfamily consisting of many trophoblast–expressed genes," *Proc. Natl. Acad. Sci.*, 94:12809–12816, 1997.

Xie et al., "Multiple pregnancy–associated glycoproteins are secreted by day 100 ovine placental tissue," *Biol. Reprod.*, 57:1384–1393, 1997.

Zoli et al., "Purification and characterization of a bovine pregnancy–associated glycoprotein," *Biol. Reprod.*, 45:1–10, 1991.

Zoli, et al., "Radioimmunoassay of a bovine pregnancy–associated glycoprotein in serum: its application for pregnancy diagnosis," *Biol. Reprod.*, 46:83–92 1992.

Zoli et al., "Light and electron microscopic immunolocalization of bovine pregnancy–associated glycoprotein in the bovine placentome," *Biol. Reprod.*, 46:623–629, 1992.

\* cited by examiner

FIG. 1A

```
Consensus  TFR.TNKIF. I.YGSG.MKG .L..DTVRIG .LVSTDQPFG LS.EE-.GF. ...-DGVLG  180 (120)

boPAG 8    ..QPL.QKIE LV....T... V.GS..IQ.. N..IVN.I.. ..QNQSS.VL EQVPY..I..  179
boPAG 2    S..EVGSPIT .F....IIQ. F.GS...... N...PE.S.. ..L...Y..D SLP.F..I..  174
boPAG12    S.GQ.HQPIS .S..P.IIQ. F.GS...... N...LK.S.. ..Q...Y..D GAP.F.....  174
boPAG11    ..L.RRP.H. .L....M.N. V.AY...... K......... ..LQQ.F..D NAP.F.....  177
boPAG 9    ..QP....T. .T....S... F.AY...... D......... ..VV..Y.LE GRN.Y.....  176
boPAG10    ..KA...I.N TN.TATSI.. Y.VY...... N...VA.... ..LK.F..D  DVP.F..I..  178
boPAG 4    ...LSRR..S .T....RIEA LVH....... D......Q.. ..CL...S..E GMR.F.....  177
boPAG 6    ...P.....R .T....R... VVH....... D......... ..CLKD.S..K GIP.F..I..  176
boPAG 1    ...L.....R .T....R... VVVH...... N......... ..I...Y..E GRI.Y.....  177
boPAG 3    ...L.....R .T....R... VVAH...... D......... ..V...Y..E GRAYY.....  178
boPAG 5    .SGL.Q...S .T....ST.. F.AY...... D.L....E.. ..M...H..E DLPF-.....  177
boPAG 7    ...P.....R .I....R.N. VIAY...... D......... ..V...Y..A HKRF-..I..  177

Consensus  L.YP..S..G AIPIFDNLKN QGAISEPVFA FLYS....EG SVVMFGGVDH .YYKGELNW.  240 (180)

boPAG 8    .A...SLAIQ. TT.V...... REV....... ...SRPENI  .T........ T.H.K.Q.I  239
boPAG 2    .AF.AMGIED T......WS  H..F...... ...NTNKP.. .......... R.......I  234
boPAG12    .A..SI.IK. I......WS  ...F...... ...NTCQP.. .......... R.......I  234
boPAG11    .S..SLAVP. T.....K..Q ........I. ...TRKEN.. ..L.L..... S.H.K...I  237
boPAG 9    .N..NI.FS. .......... .......... ...KNKQ... .........NR Q........I  236
boPAG10    .G..RRTIT. .N.....WK. ...V...... ...SQKEN.. ........A. A.......V  238
boPAG 4    .S.TNI.PS. .....YK... .......... ...KDER... .........A. R.......I  237
boPAG 6    .S..NKTFS. .F...K.... E......... ...KDKQ... .......... R.......V  236
boPAG 1    .N..NI.FS. .......K.. E.......R. ...KDER... .......... R.E.....V  237
boPAG 3    .N..NI.FS. .......... .......... ...KDEQ... .......... R.E.....V  238
boPAG 5    .N..DM.FIT T......... .......F.. ...GKVK--- .......... T........V  235
boPAG 7    .N.WNL.WSK .M....K... E......... ....NI---- ---------- ----------  213
```

FIG. 1B

| | P..Q.G.W.. | .MDRISM.R. | VIACS.GC.A | LVDTGTS.I. | GP.RLV.NI. | KLI.A.P-.G | 300 (239) |
|---|---|---|---|---|---|---|---|
| Consensus | | | | | | | |
| boPAG 8 | .VT.ARF.QV | A.SSMT.NGN | .VG...Q.Q. | ......LLV | ..TH..TD.L | ...NPN.ILN | 299 |
| boPAG 2 | .VS.TSH.QI | S.NN...NGT | .T...C..E. | .L.....M.Y | ..TK..T..H | ..MN.RL.EN | 293 |
| boPAG12 | .VS.TRY.QI | S.N....NGN | .T...R..Q. | .L.....M.H | ..T..IT...H | ..MN.RH.Q. | 293 |
| boPAG11 | .VS.TKS.LI | TV.....NGR | .G.EH..E.. | .......L.H | ..A.P.T..Q | .F.H.M..Y. | 296 |
| boPAG 9 | .LIEA.E.RV | H......K.T | .......D.E | ..H....H.E | ..G....N.H | R..RTR..FD | 295 |
| boPAG10 | .VS.V.S.HI | NI.S...NGT | .V..KR..Q. | SWIR.-RLSA | W.K.I.SK.Q | ...H.R..ID | 296 |
| boPAG 4 | .LMKA.D.SV | H.........K | .......G..K. | .......S.D.V | ..ST..N..W | ...G.T..Q. | 296 |
| boPAG 6 | .LI.V.D.FV | H...IT.K.K | .......D..K. | .......D.V | ..ST..N..W | ...R.R..L. | 295 |
| boPAG 1 | .LI.A.D.SV | H......IE.K | I......D.K. | .......D.V | ..R..N..H | R..G.I..R. | 296 |
| boPAG 3 | .LIEA.D.II | H......K.K | I......GS.E | I......A.E | ..RK..NK.H | ...G.R..RH | 297 |
| boPAG 5 | .LI.A.E.SL | H......K.K | .......G..E | FY.....L.L | ..R....N..Q | ...G.T..Q. | 294 |
| boPAG 7 | .......... | ----T.N.E | .......E.A. | ......S.N.Q | ..G..ID..Q | RI.G.T..R. | 257 |

| | SE..VSC.AV | ..LPSIIFTI | NGI.YPVP.. | AYI.KDSRG. | C....F.... | ----S..ET | 360 (295) |
|---|---|---|---|---|---|---|---|
| Consensus | | | | | | | |
| boPAG 8 | D.QML..D.I | NS..TLLL.. | ...V.....PD | Y..QRF.ERI | .FIS.QGGTE | ILKNLGTS.. | 359 |
| boPAG 2 | ...YV...D.. | KT..PV..N. | ...D..LRPQ | ...I.IQN-S | .RSV.QGGTE | ...N..SLN. | 348 |
| boPAG12 | ...YV...D.. | KT..PV..N. | ...D..L.PQ | ...T.AQN-F | .LSI.HGGTE | ...T..SP.. | 348 |
| boPAG11 | ...YM.L.PVI | SI..PV.... | ...D.S..RE | ...Q.I.NSL | .LST.HGD-D | ...T.--DQ | 348 |
| boPAG 9 | .KHY...F.T | KY....T.I. | ...K..MTAR | ...F.....R | .YSA.KENTV | ..R.TSR... | 351 |
| boPAG10 | R.HV...Q.I | GT..PAV... | ...D....AQ | ...QSL.G-Y | .FSN.LVRPQ | ...RVNES.. | 352 |
| boPAG 4 | ..HY...S.. | NS........ | KSNN.R..GQ | ...L.....R | .FTA.KGHQQ | ..S..ST.M | 352 |
| boPAG 6 | PQYF...S.. | NT........ | ...N.RL.AR | ..H......R | .YTA.KEHRF | ...S..PI.. | 351 |
| boPAG 1 | ..HY.P.SE. | NT....V... | ...N....GR | ...L.D..R | .YTT.QENRV | ...S..ST.. | 352 |
| boPAG 3 | .KYYI..S.. | NT........ | ...N.C.GR | ...VL....R | .YSM.QENKV | ...S..ST.. | 353 |
| boPAG 5 | ..HYI.F... | IS........ | ...NI...AR | ..H......H | .YPT.KENTV | ...ST.-T.. | 350 |
| boPAG 7 | .KYY...S.. | NI........ | .VN.....PR | ...L......H | .YTT.KEKRV | ...RR.-T.S | 313 |

FIG. 1C

| Consensus | WILGDVFLRL | YFSVFDRGND | RIGLA.AV | |
|---|---|---|---|---|
| boPAG 8 | .......... | ....Y....N | .....P.A | 388 (323) |
| boPAG 2 | .....I...Q | .......K.R | .....P.. | 387 |
| boPAG 12 | ....G....Q | ....R..... | S....-Q. | 376 |
| boPAG 11 | .......... | ....Y....N | .....P.. | 375 |
| boPAG 9 | ....A...R | .......... | .....R.. | 376 |
| boPAG 10 | .......... | ........N | .....P.. | 379 |
| boPAG 4 | .......... | ......RK. | .....TK. | 380 |
| boPAG 6 | .L........ | .......... | .....R.. | 380 |
| boPAG 1 | .Y........ | .......... | .....R.. | 379 |
| boPAG 3 | ........V | .......... | .....R.. | 380 |
| boPAG 5 | .......... | .......... | ....QV- | 381 |
| boPAG 7 | .V..E..... | .......... | .....RR. | 577 |
|  |  |  |  | 341 |

| | SSTFR.TNKT | F.I.YG.G.M. | KGVVAHDTVR | IGDLVSTDQP | FGLS..E.GF | ...PFDGVLG | 180 (120) |
|---|---|---|---|---|---|---|---|
| Consensus | | | | | | | |
| ovPAG 4 | ......T... | .W.T..A.T. | .......... | .......... | ...MA.Y.. | HGRR...... | 177 |
| ovPAG 7 | ......T... | .W.T..A.T. | .......... | ........I. | ...MA.Y.. | MDRR....I. | 177 |
| ovPAG 3 | .....LA... | .G.M..A.K. | .......V.. | .......... | ...VV.S.. | EHRQ......I. | 177 |
| ovPAG 6 | .....P..R. | .S.T..C.TV | .......V.. | .......... | ...TA.HVS | RCT....... | 177 |
| ovPAG 1 | .....F..D. | .R.YF.S.T. | R.F....... | .......... | ..IFL.SWL | D-I.....I. | 179 |
| ovPAG 5 | ...Y.H.T.P | .E.A..S.RI | ..HL.Y..IQ | ....N..... | ....LV.Y.. | NGL.....I. | 177 |
| ovPAG 9 | .....L..R. | .C.T..S.GL | ....I..... | ....N..... | ...TLK.Y.. | ENI....... | 176 |
| ovPAG 2 | .....L.RRP | .R.L..S.M. | N..L.Y.... | .......... | ...LQQF.. | DNA....... | 177 |
| ovPAG 8 | ...Y.L.... | .M.F.RV.KI | E...VR.... | ......A..T | ....IA.T.. | ENTTL..I.. | 177 |

| | LNYP..S..G | .IPIFDKLKN | EGAISEPVFA | FYLSKD.QEG | SVVMFGGVDH | .YYKGELNWV | 240 (180) |
|---|---|---|---|---|---|---|---|
| Consensus | | | | | | | |
| ovPAG 4 | ....RQ.CCR | PT........ | Q......... | .......E... | .......... | R......... | 237 |
| ovPAG 7 | ....RQ.CSK | TKW......S | Q......... | .......E... | .......... | T.......SL | 237 |
| ovPAG 3 | ....NL.FSK | T......... | .......... | .......E... | .......... | S...K..... | 237 |
| ovPAG 6 | ....SI.FWS | T......... | .......... | .......G... | .......... | R......... | 237 |
| ovPAG 1 | ....KI.FS. | A......... | ...F...... | .....N..K. | .......... | R......... | 239 |
| ovPAG 5 | ....N-.IL. | A......N..K | Q......... | ....GTVN. | ..L.L...K | A........I | 236 |
| ovPAG 9 | ....NI.FS. | AV........ | ....L..... | .......... | ..L.L.... | R.E....... | 236 |
| ovPAG 2 | .S..SLAVP. | T........Q | Q......... | ....F..E.. | .......... | R.E....... | 237 |
| ovPAG 8 | .S..NT.CF. | A......... | .......... | ....TNKEN. | ..L.L..... | S.H.K...I | 212 |
| | | | | ....N---- | ---------- | ---------- | |

FIG. 2B

| | | | | | | | | |
|---|---|---|---|---|---|---|---|---|
| Consensus | PL..AGDW.I | .VDRISM.R. | VIACS.GC.A | LVDTG.S.I. | GP.RLVDNIQ | KLIGA.P.G. | 300 | (240) |
| ovPAG 4 | ..VK.D..T. | Q......R.E | .....D..D. | .L...A.F.H | ..G..I.D.. | ....SE.RDL | 297 | |
| ovPAG 7 | ..VK.D..S. | H......R.E | .....D..D. | .L...A.F.H | ..G..I.D.. | ....SEQRDF | 297 | |
| ovPAG 3 | ..IK....SV | R..S.T.K.E | .....D..R. | .....S.H.Q | ..G..I..V. | ....TM.Q.S | 297 | |
| ovPAG 6 | ..IP..N.MV | HM...YIE.N | .....A..K. | V....AAF.E | ..KSQ...M. | .F...R.R.S | 297 | |
| ovPAG 1 | ..IHP.E.S. | PL.....R.K | .....G..E. | ..G..T.L.L | ..RTV.E... | .H...TQQCF | 299 | |
| ovPAG 5 | ..IRV...R. | R..H...KGK | L.G..G..E. | .....P.L.N | ..T...T... | R....M.L.P | 296 | |
| ovPAG 9 | ..TK....IV | RL....IG.K | .....GD.E. | V....TAF.G | ..RK..KK.. | .....RRR.N | 296 | |
| ovPAG 2 | .VSQTKS.L. | T......NGK | ..G.EH..E. | .....T.L.H | ..AGP.T... | .F.H.V.YDS | 297 | |
| ovPAG 8 | ---------. | TMK.-----E | .....D..R. | .....S.H.Q | ..G.....V. | .H..TM.Q.S | 258 | |
| Consensus | KHYVSCSAVN | TLPSIIFTIN | GINYPVPAQA | YILK.S.G.C | YT.F...RVR | .STE.WVLGD | 360 | (300) |
| ovPAG 4 | ...I...... | .......... | .......... | ....G.T.H. | ..A.RAK... | T...S..... | 357 | |
| ovPAG 7 | ...I...... | .......... | .......... | ....G.T.H. | ..A.RAK... | T...S..... | 357 | |
| ovPAG 3 | M...P..... | .......... | .......... | ....GFT.H. | ..A.RAK... | T...S..... | 357 | |
| ovPAG 6 | .Y..P..V.. | .......R.. | S......GR. | ....NHR.R. | ..T.KENQWS | P...I.I... | 357 | |
| ovPAG 1 | EYF......Y | A....V.... | .......P.. | .LV.D.R.Q. | .SP.QVN.AN | P.A.N.I... | 359 | |
| ovPAG 5 | ........TI. | I......... | ....TL.... | ....T.Q.G. | F.T.KGA..F | KHR.T..... | 356 | |
| ovPAG 9 | .--------- | ---------- | ---------- | ----DDA.R. | S.T.QEN... | L...S.L..N | 323 | |
| ovPAG 2 | EYM...PVIS | I..PV..... | S.D.S...E. | ..Q.I.NSL. | LSS.HGDN-- | --.DK.I... | 353 | |
| ovPAG 8 | M...P..... | .......... | .......GR. | ....DFR.R. | ..N.KKKIA. | TF..Y....E | 318 | |

FIG. 2C

```
Consensus  VFLRLYFSVF  DRGNDRIGLA  PAV  383 (323)

ovPAG 4    ..........  ..........  ..M  380
ovPAG 7    ..........  ..........  ..M  380
ovPAG 3    ..........  ..H.......  R.G  380
ovPAG 6    ..........  ..H.......  R..  380
ovPAG 1    ....R.....  ..........  R..  382
ovPAG 5    I........Y  ..EHN..A..  Q.R  379
ovPAG 9    ...V.L....  .....N....  ...  346
ovPAG 2    ........Y.  ..........  ...  376
ovPAG 8    P.........  ..........  ...  341
```

FIG. 2D

| boPAG | 2 | 4 | 5 | 6 | 7 | 8 | 9 | 10 | 11 | 12 |
|---|---|---|---|---|---|---|---|---|---|---|
| Hybrid (d25) | 4 |  | 1 | 1 | 1 | 5 | 1 | 1 | 1 |  |
| Immuno (d25) |  | 19 |  |  |  |  |  |  |  |  |
| RT-PCR (d19) | 9 |  |  |  |  | 11 | 3 |  | 3 | 6 |

FIG. 3

| BoPAG: | 1 | 2 | 3 | 4 | 5 | 6 | 7 | 8 | 9 | 10 | 11 | 12 |
|---|---|---|---|---|---|---|---|---|---|---|---|---|
| 1 | 100<br>100 | | | | | | | | | | | |
| 2 | 73<br>57 | 100<br>100 | | | | | | | | | | |
| 3 | 91<br>86 | 74<br>58 | 100<br>100 | | | | | | | | | |
| 4 | 88<br>76 | 73<br>55 | 87<br>73 | 100<br>100 | | | | | | | | |
| 5 | 86<br>75 | 60<br>61 | 86<br>74 | 85<br>76 | 100<br>100 | | | | | | | |
| 6 | 89<br>80 | 73<br>57 | 88<br>78 | 89<br>76 | 84<br>70 | 100<br>100 | | | | | | |
| 7 | 87<br>79 | 73<br>56 | 87<br>78 | 86<br>71 | 85<br>72 | 89<br>77 | 100<br>100 | | | | | |
| 8 | 68<br>53 | 68<br>55 | 67<br>51 | 67<br>49 | 70<br>54 | 69<br>53 | 71<br>53 | 100<br>100 | | | | |
| 9 | 87<br>77 | 74<br>59 | 88<br>78 | 85<br>68 | 85<br>74 | 87<br>74 | 86<br>71 | 68<br>53 | 100<br>100 | | | |
| 10 | 70<br>56 | 72<br>50 | 69<br>55 | 68<br>53 | 71<br>58 | 70<br>57 | 68<br>53 | 71<br>55 | 69<br>57 | 100<br>100 | | |
| 11 | 74<br>59 | 77<br>62 | 73<br>58 | 73<br>56 | 76<br>62 | 73<br>59 | 75<br>59 | 72<br>56 | 73<br>57 | 72<br>57 | 100<br>100 | |
| 12 | 75<br>61 | 90<br>83 | 75<br>60 | 74<br>58 | 77<br>63 | 75<br>59 | 74<br>58 | 70<br>56 | 75<br>60 | 73<br>60 | 79<br>64 | 100<br>100 |

FIG. 4

COMPOSITIONS AND METHODS FOR EARLY PREGNANCY DIAGNOSIS

This application claims priority to U.S. Provisional Application Serial No. 60/078,783 filed Mar. 20, 1998 and U.S. Provisional Application Serial No. 60/106,188 filed Oct. 28, 1998. The entire text of each of the above-referenced disclosures is specifically incorporated by reference herein without disclaimer. The government may own rights in the present invention pursuant to grant R37 HD29483 and USDA grant 9601842.

BACKGROUND OF THE INVENTION

I. Field of the Invention

The present invention relates generally to the fields of veterinary medicine, reproductive biology and diagnostics. More specifically, the present invention relates to the use of analytical methods to detect early stage pregnancy.

II. Related Art

Pregnancy diagnosis is an important component in sound reproductive management, particularly in the dairy industry (Oltenacu et al., 1990) where a high proportion of artificial inseminatioris fail (Streenan and Diskin, 1986). A reliable yet simple pregnancy test for cattle has long been sought. Several procedures are available, including a milk progesterone assay (Oltenacu et al., 1990; Markusfeld et al., 1990) estrone sulfate analysis (Holdsworth et al., 1982; Warnick et al., 1995), rectal palpation (Hatzidakis et al., 1993), ultrasound (Beal et al., 1992; Cameron and Malmo, 1993), and blood tests for pregnancy-specific antigens. Of these, the progesterone milk assay is the most cost effective for the producer (Oltenacu et al., 1990; Markusfeld et al., 1990). Next best is rectal palpation, performed at day 50 (Oltenacu et al., 1990). Even though all the procedures are potentially useful, all have fallen short of expectations in terms of their practical, on-farm use. For example, measurements of milk or serum progesterone around day 18–22 yield unacceptably high rates of false positives (Oltenacu et al., 1990; Markusfeld et al., 1990). Rectal palpation can be used to detect pregnancy as early as day 35, but this procedure can lead to 5–10% or greater embryonic mortality (Oltenacu et al., 1990; Hatzidakis et al., 1993). Rectal palpation on day 50 causes less damage to the embryos, but had only marginal economic value because of its lateness (Oltenacu et al., 1990). Ultrasonography has an advantage over rectal palpation in accuracy, particularly before day 45 (Beal et al., 1992; Cameron and Malmo, 1993), but the instrument is expensive, its use requires considerable training, and there is a finite risk to the animal. A related procedure, Doppler sonography, is more accurate than rectal palpation (Cameron and Malmo, 1993), but again requires well trained personnel. The presence of estrone sulfate in urine or serum provides another test but is only useful after day 100 as concentrations rise (Holdsworth et al., 1982; Warnick et al., 1995).

The discovery of pregnancy-specific protein B (PSP-B) (Butler et al., 1982) provided a new approach to pregnancy diagnosis since it could be detected in the blood of pregnant cows by the fourth week of pregnancy (Sasser et al., 1986; Humblot et al., 1988). Two other groups have developed immunoassays that may be based on an identical or immunologically similar antigen (Zoli et al., 1992a; Mialon et al., 1993; Mialon et al., 1994). In one case, the antigen (Mr ~67 kDa) was called bovine pregnancy-associated glycoprotein (boPAG; now boPAG-1) (Zoli et al., 1992a); in the second, it was designated as pregnancy serum protein 60 (PSP60) (Mialon et al., 1993; Mialon et al., 1994). The immunoassay for PSP-B/boPAG1/PSP60 has two advantages. First, it can detect pregnancy relatively early. Second, interpretation of the assays does not require knowledge of the exact date of service, since boPAG-1 immunoreactive molecules are always present in the maternal serum of pregnant cows by day 28, and concentrations increase as pregnancy advances (Sasser et al., 1986; Mialon et al., 1993; Mialon et al., 1994).

There remain, however, two major disadvantages to this procedure. First, positive diagnosis in the fourth week of pregnancy remains somewhat uncertain because antigen concentrations in blood are low and somewhat variable. Second, boPAG1 concentrations rise markedly at term (Sasser et al., 1986; Zoli et al., 1992a; Mialon et al., 1993) and, due to the long circulating half-life of the molecule (Kiracofe et al., 1993), the antigen can still be detected 80–100 day postpartum (Zoli et al., 1992a; Mialon et al., 1993; Mialon et al., 1994; Kiracofe et al., 1993), compromising pregnancy diagnosis in cows bred within the early postpartum period. Thus, the test can be carried out in dairy cows at day 30 only if artificial insemination ("AI") is performed at or after 70 day post-partum.

A pregnancy test that could be carried out reliably and early in pregnancy could provide definitive indication as to whether rebreeding or culling is required. In general, AI is successful less than 50% of the time and the producer must either rely on overt signs of return to estrus (that are easily missed) or delay rebreeding until pregnancy failure is confirmed by one of the methods described above. Such delays are extremely costly and constitute a major economic loss to the industry. In the North Island of New Zealand alone, over two million cows are bred in a six-week period. A precise knowledge of the pregnancy status of these animals would be an invaluable aid to that and other diary industries worldwide. As should be apparent, this field has a need for a feasible, sensitive and accurate pregnancy test in cattle that can be performed by the end of the third week after insemination.

SUMMARY OF THE INVENTION

Therefore, it is an objective of the present invention to provide a sensitive and accurate test for early pregnancy. Using a selected boPAG as the biochemical marker, the present invention provides an early pregnancy test in which the PAG antigen a) is produced abundantly in early, and preferably not in late, pregnancy, b) is a product of the binucleate cell, and absent or not present in significant amounts postpartum, and c) minimally cross-reacts with late PAG products that might persist in maternal serum during the post-partum interval. The early immunoassay will be particularly useful in the dairy industry where animals are usually confined for at least part of the day and where intensive management is practiced. A modified test also is likely to have value in captive breeding programs for other animals, e.g., for the ruminants okapi or giraffe and possibly for other non-ruminant species.

Thus, in a particularly preferred embodiment, there is provided a method for detecting pregnancy in a bovine animal comprising obtaining a sample from the animal; and detecting at least one of pregnancy associated antigen (PAG) wherein the PAG is present in early pregnancy and absent at about two months postpartum, whereby the presence of the PAG indicates that the animal is pregnant. Insemination is usually, but not invariably, performed about two months after calving in dairy cattle, until a successful conception results. The detection method may be applied within about 15 days of insemination and advantageously at about 20 to about 25 days after insemination. Given these facts, the time window for the disappearance of a useful PAG is about two months after calving, although earlier disappearance is also advantageous. However, PAGs which persist until about 65, about 70, about 75, about 80, about 85, about 90, about 95, or about 100 days after calving also are suitable for use. The exact day for this determination may vary depending on individual circumstances, however, given the teachings provided herein, an individual of skill in the art will understand the significance of testing for the absence of PAG during this time period and will be able to determine such a day. For example, if insemination occurs at a later date than 60 days post-partum, PAGs with a later disappearance profile may be useful. Thus, it is contemplated that the PAG of the present invention is detectable in early pregnancy but is not detectable at two months postpartum. Also, it is understood that the PAG indicative of early pregnancy may be absent in late pregnancy or present in amounts that are markedly less than those found in early pregnancy (for example, between day 15 and day 30 of pregnancy).

In particularly preferred embodiments, the PAG may be selected from the group consisting of PAG2, PAG4, PAG5, PAG6, PAG7 and PAG9. In more preferred embodiments, the PAG, independently, may be BoPAG2, BoPAG4, BoPAG5, BoPAG6, BoPAG7, BoPAG9, boPAG7v; boPAG9v; boPAG15; boPAG16; boPAG17; boPAG18; boPAG19; boPAG20 or boPAG21.

In particular aspects of the present invention, the sample may be a saliva, serum, blood, milk or urine sample. Methods of sample collection are well known to those of skill in the art, for example, blood may be collected by needle from a tail vein or other blood vessel, milk withdrawn from the udder. Saliva and urine also may be collected according to well known techniques. In defined embodiments, it is contemplated that the detecting comprises an immunologic detection. In preferred embodiments, the immunologic detection comprises detection BoPAG2, BoPAG4, BoPAG5, BoPAG6, BoPAG7, BoPAG9, boPAG7v; boPAG9v; boPAG15; boPAG16; boPAG17; boPAG18; boPAG19; boPAG20 or boPAG21 with polyclonal antisera. In alternative embodiments, the immunologic detection comprises detection of BoPAG2, BoPAG4, BoPAG5, BoPAG6, BoPAG7, BoPAG9, boPAG7v; boPAG9v; boPAG15; boPAG16; boPAG17; boPAG18; boPAG19; boPAG20 or boPAG21 with a monoclonal antibody in particularly preferred embodiment, the immunologic detection may comprise ELISA, in other embodiments, the immunologic detection may comprises RIA, in still further alternative embodiments, the immunologic detection comprises Western blot.

In certain aspects of the present invention, the method for detecting pregnancy may further comprise detecting a second PAG in the sample. The second PAG may be selected from the group consisting of BoPAG2, BoPAG4, BoPAG5, BoPAG6, BoPAG7, BoPAG9, boPAG7v; boPAG9v; boPAG15; boPAG16; boPAG17; boPAG18; boPAG19; boPAG20 or boPAG21. Alternatively, the second PAG may be any other pregnancy Likewise the present invention contemplates a pregnancy detection method that further comprises detecting a third PAG in the sample.

In those embodiments employing ELISA as an immunological technique, it is contemplated that the ELISA may be a sandwich ELISA comprising binding of a PAG to a first antibody preparation fixed to a substrate and a second antibody preparation labeled with an enzyme. Sandwich ELISA is well known to those of skill in the art. In particularly preferred embodiments, the enzyme may be alkaline phosphatase or horseradish peroxidase. In other embodiments, the first antibody preparation may be a monoclonal antibody preparation.

Other aspects of the present invention contemplate an antibody composition that reacts immunologically with BoPAG2, BoPAG4, BoPAG5, BoPAG6, BoPAG7, BoPAG9, boPAG7v; boPAG9v; boPAG15; boPAG16; boPAG17; boPAG18; boPAG19; boPAG20 or boPAG21. Particularly preferred embodiments contemplate an provide an antibody composition that reacts immunologically with BoPAG4. Further embodiments provide an antibody composition that reacts immunologically with BoPAG5. Still further embodiments contemplate an antibody composition that reacts immunologically with BoPAG6. Other embodiments contemplate an antibody composition that reacts immunologically with BoPAG7. Still further embodiments, contemplate an antibody composition that reacts immunologically with BoPAG9. It is contemplated that the antibody composition. may be a monoclonal antibody composition or a polyclonal antibody composition.

The present invention further provides a hybridoma cell that secretes a monoclonal antibody that reacts immunologically with BoPAG2, BoPAG4, BoPAG5, BoPAG6, BoPAG7, BoPAG9, boPAG7v; boPAG9v; boPAG15; boPAG16; boPAG17; boPAG18; boPAG19; boPAG20 or boPAG21.

Also contemplated herein is a method of making a monoclonal antibody to BoPAG2, BoPAG4, BoPAG5, BoPAG6, BoPAG7, BoPAG9, boPAG7v; boPAG9v; boPAG15; boPAG16; boPAG17; boPAG18; boPAG19; boPAG20 or boPAG21 comprising the steps of immunizing an animal with a BoPAG preparation; obtaining antibody secreting cells from the immunized animal; immortalizing the antibody secreting cells; and identifying an immortalized cell that secretes antibodies that bind immunologically with the immunizing BoPAG.

Another aspect of the present invention provides a method of identifying a pregnancy associated glycoprotein (PAG) that is an early indicator of pregnancy in an Eutherian animal comprising the steps of obtaining a cDNA library prepared from the placenta of the animal between days 15 and 30 of pregnancy; and hybridizing the library under high stringency conditions with a PAG-derived nucleic acid probe; whereby hybridization of the probe identifies the PAG.

Also provided by the present invention is a method of identifying a pregnancy associated glycoprotein (PAG) that is an early indicator of pregnancy in an Eutherian animal comprising the steps of obtaining an RNA preparation from the placenta of the animal between days 15 and 30 of pregnancy; and performing RT-PCR™ on the preparation using PAG-derived primers; whereby amplification identifies the PAG.

In particularly preferred embodiments, the PAG detected in cattle (*Bos taurus*) may be any one or more of the following PAGs that are so far known to be produced in early pregnancy, namely: BoPAG2, BoPAG4, BoPAG5, BoPAG6, BoPAG7, BoPAG9, boPAG7v; boPAG9v; boPAG15; boPAG16; boPAG17; boPAG18; boPAG19; boPAG20 or boPAG21. More specifically, the bovine PAGs that may be detected comprise the sequence of one or more of the following amino acid sequences: SEQ ID NO:25, SEQ ID NO:27, SEQ ID NO:28, SEQ ID NO:29, SEQ ID NO:30, and SEQ ID NO:32; SEQ ID NO:40; SEQ ID NO:42; SEQ ID NO:44; SEQ ID NO:46; SEQ ID NO:48; SEQ ID NO:50; SEQ ID NO:52; SEQ ID NO:54; SEQ ID NO:56. When applied to other species, the present invention will allow detection of other PAGs produced at the time the trophoblast (pre-placenta) begins either to attach or to implant into the uterine wall of the mother. The "early" PAGs in these species may cross-react immunologically with the PAGs useful in detecting early pregnancy in cattle.

The present invention contemplates an isolated and purified BoPAG2 polypeptide. In preferred embodiment, the BoPAG2 polypeptide comprises the sequence of SEQ ID NO:25. Further, the invention contemplates an isolated and purified BoPAG4 polypeptide. In particularly preferred embodiments, the BoPAG4 polypeptide comprises the sequence of SEQ ID NO:27. Another embodiment contemplates an isolated and purified BoPAG5 polypeptide. A particularly preferred BoPAG5 polypeptide comprises the sequence of SEQ ID NO:28. Yet another embodiment provides an isolated and purified BoPAG6 polypeptide. In preferred embodiments, the BoPAG6 polypeptide comprises the sequence of SEQ ID NO:29. Another embodiment contemplates an isolated and purified BoPAG7 polypeptide. An especially preferred BoPAG7 polypeptide comprises the sequence of SEQ ID NO:30. Further contemplated by the present invention is an isolated and purified BoPAG9 polypeptide. In preferred embodiments, the BoPAG9 polypeptide comprises the sequence of SEQ ID NO:32. Further contemplated by the present invention is an isolated and purified BoPAG7v polypeptide. In preferred embodiments, the BoPAG7v polypeptide comprises the sequence of SEQ ID NO:40. Further contemplated by the present invention is an isolated and purified BoPAG9v polypeptide. In preferred embodiments, the BoPAG9v polypeptide comprises the sequence of SEQ ID NO:42. Further contemplated by the present invention is an isolated and purified BoPAG15 polypeptide. In preferred embodiments, the BoPAG15 polypeptide comprises the sequence of SEQ ID NO:44. Further contemplated by the present invention is an isolated and purified BoPAG16 polypeptide. In preferred embodiments, the BoPAG16 polypeptide comprises the sequence of SEQ ID NO:46. Further contemplated by the present invention is an isolated polypeptide. In preferred embodiments, the BoPAG16 polypeptide comprises the and purified BoPAG17 polypeptide. In preferred embodiments, the BoPAG17 polypeptide comprises the sequence of SEQ ID NO:48. Further contemplated by the present invention is an isolated and purified BoPAG18 polypeptide. In preferred embodiments, the BoPAG18 polypeptide comprises the sequence of SEQ ID NO:50. Further contemplated by the present invention is an isolated and purified BoPAG19 polypeptide. In preferred embodiments, the BoPAG19 polypeptide comprises the sequence of SEQ ID NO:52. Further contemplated by the present invention is an isolated and purified BoPAG20 polypeptide. In preferred embodiments, the BoPAG20 polypeptide comprises the sequence of SEQ ID NO:54. Further contemplated by the present invention is an isolated and purified BoPAG2 1 polypeptide. In preferred embodiments, the BoPAG21 polypeptide comprises the sequence of SEQ ID NO:56.

Alternative embodiments of the present invention define an isolated and purified nucleic acid encoding BoPAG2. In particularly preferred embodiments, the BoPAG2 encoding nucleic acid comprises the sequence of SEQ ID NO:2. In other preferred embodiments, the BoPAG2 encoding nucleic acid encodes a BoPAG2 polypeptide comprising the sequence of SEQ ID NO:25.

Another embodiment provides an isolated and purified nucleic acid encoding BoPAG4. In preferred embodiments the BoPAG4 encoding nucleic acid comprises the sequence of SEQ ID NO:4. In other equally preferred embodiments, the BoPAG4 encoding nucleic acid encodes a BoPAG4 polypeptide comprising the sequence of SEQ ID NO:27.

In yet another embodiment, there is contemplated an isolated and purified nucleic acid encoding BoPAG5. In preferred embodiments, the BoPAG5 encoding nucleic acid comprises the sequence of SEQ ID NO:5. In other preferred embodiments, the BoPAG5 encoding nucleic acid encodes a BoPAG5 polypeptide comprising the sequence of SEQ ID NO:28.

In still another aspect of the present invention there is provided an isolated and purified nucleic acid encoding BoPAG6. In particularly preferred aspects the BoPAG6 encoding nucleic acid comprises the sequence of SEQ ID NO:6. In particularly preferred embodiments, the nucleic acid encodes a BoPAG6 polypeptide comprising the sequence of SEQ ID NO:29.

Also contemplated by the present invention is an isolated and purified nucleic acid encoding BoPAG7. In preferred embodiments, the nucleic acid comprises the sequence of SEQ ID NO:7. In other preferred embodiments, the nucleic acid encodes a BoPAG7 polypeptide comprising the sequence of SEQ ID NO:30.

Yet another embodiment contemplates an isolated and purified nucleic acid encoding BoPAG9. In particular embodiments the BoPAG9 encoding nucleic acid comprises the sequence of SEQ ID NO:9. In other particularly preferred embodiments, the BoPAG9 encoding nucleic acid encodes a BoPAG9 polypeptide comprising the sequence of SEQ ID NO:32.

Yet another embodiment contemplates an isolated and purified nucleic acid encoding BoPAG7v. In particular embodiments the BoPAG7v encoding nucleic acid comprises the sequence of SEQ ID NO:39. In other particularly preferred embodiments, the BoPAG7v encoding nucleic acid encodes a BoPAG7v polypeptide comprising the sequence of SEQ ID NO:40.

Yet another embodiment contemplates an isolated and purified nucleic acid encoding BoPAG9v. In particular embodiments the BoPAG9v encoding nucleic acid comprises the sequence of SEQ ID NO:41. In other particularly preferred embodiments, the BoPAG7v encoding nucleic acid encodes a BoPAG9v polypeptide comprising the sequence of SEQ ID NO:42.

Yet another embodiment contemplates an isolated and purified nucleic acid encoding BoPAG15. In particular embodiments the BoPAG15 encoding nucleic acid comprises the sequence of SEQ ID NO:43. In other particularly preferred embodiments, the BoPAG7v encoding nucleic acid encodes a BoPAG15 polypeptide comprising the sequence of SEQ ID NO:44.

Yet another embodiment contemplates an isolated and purified nucleic acid encoding BoPAG16. In particular embodiments the BoPAG16 encoding nucleic acid comprises the sequence of SEQ ID NO:45. In other particularly preferred embodiments, the BoPAG7v encoding nucleic acid encodes a BoPAG16 polypeptide comprising the sequence of SEQ ID NO:46.

Yet another embodiment contemplates an isolated and purified nucleic acid encoding BoPAG17. In particular embodiments the BoPAG17 encoding nucleic acid comprises the sequence of SEQ ID NO:47. In other particularly preferred embodiments, the BoPAG7v encoding nucleic acid encodes a BoPAG17 polypeptide comprising the sequence of SEQ ID NO:48.

Yet another embodiment contemplates an isolated and purified nucleic acid encoding BoPAG18. In particular embodiments the BoPAG18 encoding nucleic acid comprises the sequence of SEQ ID NO:49. In other particularly preferred embodiments, the BoPAG7v encoding nucleic acid encodes a BoPAG18 polypeptide comprising the sequence of SEQ ID NO:50.

Yet another embodiment contemplates an isolated and purified nucleic acid encoding BoPAG19. In particular embodiments the BoPAG19 encoding nucleic acid comprises the sequence of SEQ ID NO:51. In other particularly preferred embodiments, the BoPAG7v encoding nucleic acid encodes a BoPAG19 polypeptide comprising the sequence of SEQ ID NO:52.

Yet another embodiment contemplates an isolated and purified nucleic acid encoding BoPAG20. In particular embodiments the BoPAG20 encoding nucleic acid comprises the sequence of SEQ ID NO:53. In other particularly preferred embodiments, the BoPAG7v encoding nucleic acid encodes a BoPAG20 polypeptide comprising the sequence of SEQ ID NO:54.

Yet another embodiment contemplates an isolated and purified nucleic acid encoding BoPAG21. In particular embodiments the BoPAG21 encoding nucleic acid comprises the sequence of SEQ ID NO:55. In other particularly preferred embodiments, the BoPAG7v encoding nucleic acid encodes a BoPAG21 polypeptide comprising the sequence of SEQ ID NO:56.

Also contemplated herein are oligonucleotides comprising at least 15 consecutive base pairs of any PAG encoding sequence, or a complement thereof, disclosed herein. Particularly contemplated is an oligonucleotide comprising at least about 15 consecutive bases of the sequence of SEQ ID NO:9, or the complement thereof. In other embodiments, the oligonucleotide is about 20 bases in length. Also contemplated is an oligonucleotide comprising at least about 15 consecutive bases of the sequence of SEQ ID NO:7, or the complement thereof. another embodiments contemplates an oligonucleotide comprising at least about 15 consecutive bases of the sequence of SEQ ID NO:6, or the complement thereof. Yet another embodiments provides an oligonucleotide comprising at least about 15 consecutive bases of the sequence of SEQ ID NO:5, or the complement thereof. In still a further embodiment, there is contemplated an oligonucleotide comprising at least about 15 consecutive bases of the sequence of SEQ ID NO:4, or the complement thereof. Yet another embodiment contemplates an oligonucleotide comprising at least about 15 consecutive bases of the sequence of SEQ ID NO:2 or the complement thereof Yet another embodiment contemplates an oligonucleotide comprising at least about 15 consecutive bases of the sequence of SEQ ID NO:39 or the complement thereof. Yet another embodiment contemplates an oligonucleotide comprising at least about 15 consecutive bases of the sequence of SEQ ID NO:41 or the complement thereof Yet another embodiment contemplates an oligonucleotide comprising at least about 15 consecutive bases of the sequence of SEQ ID NO:43 or the complement thereof. Yet another embodiment contemplates an oligonucleotide comprising at least about 15 consecutive bases of the sequence of SEQ ID NO:45 or the complement thereof. Yet another embodiment contemplates an oligonucleotide comprising at least about 15 consecutive bases of the sequence of SEQ ID NO:47 or the complement thereof. Yet another embodiment contemplates an oligonucleotide comprising at least about 15 consecutive bases of the sequence of SEQ ID NO:49 or the complement thereof. Yet another embodiment contemplates an oligonucleotide comprising at least about 15 consecutive bases of the sequence of SEQ ID NO:51 or the complement thereof. Yet another embodiment contemplates an oligonucleotide comprising at least about 15 consecutive bases of the sequence of SEQ ID NO:53 or the complement thereof. Yet another embodiment contemplates an oligonucleotide comprising at least about 15 consecutive bases of the sequence of SEQ ID NO:55 or the complement thereof. Of course it is understood that oligonucleotides of longer lengths are also contemplated including oligonucleotides of 17, 18, 19, 20, 21, 22, 23, 24, 25, 30, 35, 40, 45, 50 or more consecutive base pairs in length.

The present invention further provides a kit comprising a first monoclonal antibody preparation that binds immunologically to BoPAG2, BoPAG4, BoPAG5, BoPAG6, BoPAG7, BoPAG9, boPAG7v; boPAG9v; boPAG15; boPAG16; boPAG17; boPAG18; boPAG19; boPAG20 or boPAG21; and a suitable container means therefor. It is contemplated that in particular embodiments, the kit may further comprise a second monoclonal antibody preparation that binds immunologically to the same BoPAG as the first monoclonal antibody, but wherein the first and the second monoclonal antibodies bind to different epitopes; and a suitable container means therefor. In particularly preferred aspects the first antibody preparation is attached to a support. It is contemplated that the support may be any support routinely used in immunological techniques. In particularly preferred embodiments, the support independently is a polystyrene plate, test tube or dipstick.

In particular embodiments, the second antibody preparation comprises a detectable label. The detectable label may be independently a fluorescent tag, a chemilluminescent tag, or an enzyme. In particularly defined embodiment, the enzyme is alkaline phosphatase or horseradish peroxidase. In further preferred embodiments, the kit may also comprise a substrate for the enzyme. In other embodiments, the kit may further comprise a buffer or diluent; and a suitable container means therefor.

In another embodiment, there is provided a kit including a first antibody composition that binds immunologically to BoPAG2, BoPAG4, BoPAG5, BoPA6, BoPAG7, BoPAG9, boPAG7v; boPAG9v; boPAG15; boPAG16; boPAG17; boPAG18; boPAG19; boPAG20 or boPAG21; and a suitable container means therefor as well as a second antibody composition that binds immunologically to the same boPAG as the first antibody composition, but the first and second antibody compositions bind to different epitopes; and included in this defined kit is a suitable container means therefor. More specifically, this aspect of the invention encompasses a second antibody composition including a detectable label. Other kit components, including reagent reservoirs, instructions and the like are well known to those of skill in the art and also are contemplated for use in the kits described herein.

In other embodiments, there is provided a method for detecting pregnancy in a non-bovine Eutherian animal comprising obtaining a sample from the animal; and detecting at least one of pregnancy associated antigen (PAG) in the sample, wherein the PAG is present in early pregnancy, whereby the presence of the PAG indicates that the animal is pregnant. The PAG may be absent at a period postpartum. As used herein, the term "absent" means not present using a given detection method. In other embodiments the PAG may be diminished postpartum. As used herein, "diminished" means dropping to undetectable or almost undetectable levels using a given protocol. In particularly preferred embodiment, the PAG may be selected from the group consisting of PAG2, PAG4, PAG5, PAG6, PAG7 and PAG9. In various embodiments, the animal in which pregnancy is being determined, may include all Artiodactyla which include Suidae (pigs and their relatives) and Camellidae (camels). It is contemplated that the animal may be a member of the suborder Ruminantia. In more defined embodiments, the Ruminantin may be a member of the family Bovidae. In more particular embodiments, the animal is a goat or sheep. In other embodiments the animal may be a member of the order Perissodactyla. In preferred embodiments, the animal may be a horse or rhinoceros. In alternative preferred embodiments, the animal is a member of the order Carnivora. More particularly the animal may be an animal of the canine or feline species. Even more particularly, the animal may be a dog or a cat. In other embodiments, the animal may be a human or a panda.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1. Aligned amino acid sequences of different boPAGs. Each structure was inferred from the sequences of its cDNA. The likely signal sequence is underlined and a known site of propeptide sequence cleavage (ISG↓RG/DS) for certain PAGs is shown (vertical arrow). Many additional sequences, some from cDNA not containing entire ORF, others differing less than 5% in nucleotide sequence from those shown, are known. Numbering at end of rows is by amino acid residue starting the Met1. Numbers in parentheses show the equivalent residue of pepsin. Boxes indicate the conserved sequences around the catalytic aspartic acid residues (Asp32 and Asp 215). GenBank Accession codes for boPAG1 through boPAG12 are M73961, L06 151, L06 153 and AF020506 through AF 020514, respectively.

FIG. 2. The aligned amino acid sequences of different ovPAGs. See legend to FIG. 1 for details. GenBank Accession codes for ovPAG1 through ovPAG9 are M73962, U30251 and U94789 through U94795, respectively.

FIG. 3. Summary of cloning data for boPAG expressed in day 19 and 25 bovine placenta. Early boPAG clones were identified by three independent procedures. Numbers indicate how many clones of identical sequence were isolated by each procedure. First, a day 25 bovine cDNA library was screened by homologous hybridization (Hybrid) with a probe consisting of ov, bo and poPAG1 and 2 as well as eqPAG cDNA. Sixteen clones with full length cDNA were purified and partially sequenced. The library was then immunoscreened (Immuno) with and anti-boPAG1antiserum and 19 clones were purified and partially sequenced. RNA from a day 19 Holstein cow placenta was reverse transcribed and amplified with PCR™ (RT-PCR™). The PCR™ products were subcloned and partially sequenced. Note, most of the early boPAG were identified by homologous hybridization.

FIG. 4. Pairwise comparisons of the amino acid and nucleotide sequences of bovine PAG The data show percent nucleotide sequence identity (shaded) and percent amino acid sequence identity of translated sequences (unshaded).

DETAILED DESCRIPTION OF ILLUSTRATIVE EMBODIMENTS

I. The Present Invention

Figure 5:
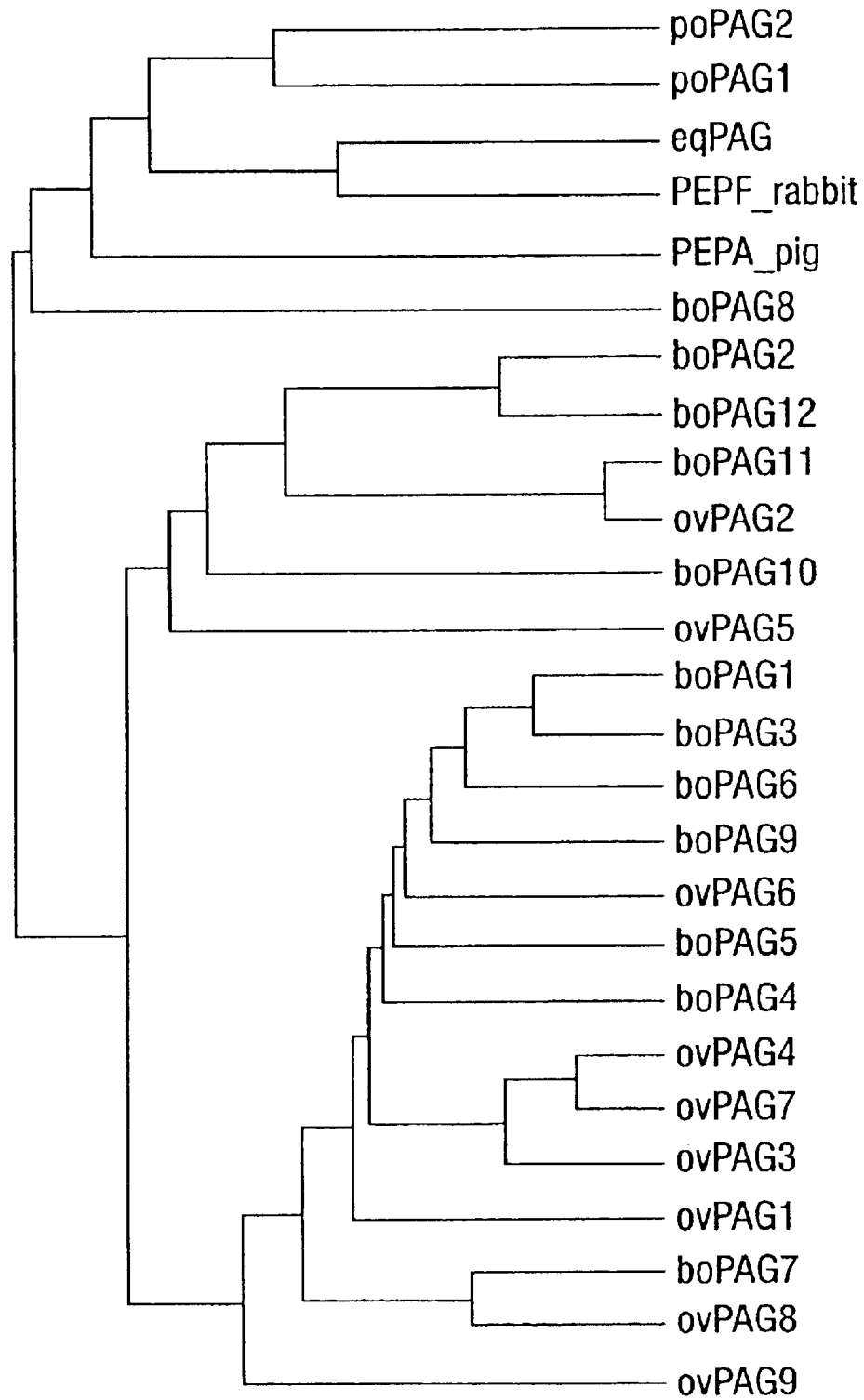
FIG. 5. A phylogram based on amino acid sequences showing the relationship of all known cloned PAGs to common mammalian aspartic proteinases. The tree was constructed by the Wisconsin GCG programs Distances and GrowTree. The lengths of the branches are proportional to the degree of amino acid diversity within pairs of proteins. Protein data bank symbols: PEPA_pig, porcine pepsinogen A; PEPF_rabbit, rabbit pepsinogen F.

Despite the availability of several assays to detect pregnancy, there remains a need to provide improved assays for accurate and early detection of pregnancy, especially in cattle that are bred within two to three months postpartum or earlier. In the context of the present invention, a preferred species is bovine. The present invention identifies several placentally expressed polypeptides, designated pregnancy associated glycoproteins (PAGs) that can be utilized to make early and accurate diagnoses of bovine and other pregnancies. Additional embodiments include the development of reagents from these polypeptides, and their corresponding genes, for use in assays to detect pregnancy. Extrapolation to other closely and distantly related species extends the application of these methods.

For use according to the present invention, selected PAGs are those that a) is produced abundantly in early and preferably not in late pregnancy, b) is a product of the binucleate cell, and absent or not present in significant amounts postpartum, and c) minimally cross-reacts with late PAG products that might persist in maternal serum during the post-partum interval. Further, the PAG should be detectable in serum at concentrations sufficient for a straightforward and rapid detection. Finally, the PAGs should be amenable to reproducible polyclonal and monoclonal antibody production in suitable host species. The remaining disclosure describes various features of the invention and their implementation.

II. Pregnancy Associated Glycoproteins

The placenta is the hallmark of the eutherian mammal. Rather than being the most anatomically conserved mammalian organ, however, it arguably is the most diverse (Haig, 1993). Placentation ranges from the invasive hemochorial type, as in the human, where the trophoblast surface is in direct contact with maternal blood, to the epitheliochorial (e.g., pig), where the uterine epithelium is not eroded (Amoroso, 1952). Not only is placental structure highly variable, the polypeptide hormones the placenta produces also vary between species (Haig, 1993; Roberts et al., 1996). For example, no group of mammals other than higher primates possesses a chorionic gonadotrophin homologous to hCG for luteal support in early pregnancy, and only the ruminant ungulates are known to produce Type I interferon as an antilyteolytic hormone (Roberts et al., 1996).

Placentation in ruminants, such as cattle and sheep, is superficial, relatively noninvasive, and known as synepitheliochorial cotyledonary (Wooding, 1992). 'Synepitheliochorial' describes the fetal-maternal syncytium formed by the fusion of trophoblast binucleate cells and uterine epithelial cells, whereas, 'cotyledonary' describes the gross structure of the placenta and specifically the tufts of villous trophoblast (cotyledons) that insinuate themselves into the crypts of the maternal caruncles. These regions of interdigitated and partially fused fetal cotyledonary and maternal caruncles are the placentomes and are the main sites for nutrient and gas exchange in the placenta. The binucleate cells, which compose about 20% of the surface epithelium (trophectoderm) migrate and fuse with maternal uterine epithelial cells and deliver their secretory products directly to the maternal system. Among the products are the placental lactogens (Wooding, 1981) and the pregnancy-associated glycoproteins (Zoli et al., 1992a.)

Bovine pregnancy-associated glycoproteins (boPAGs), also known under a variety of other names including pregnancy-specific protein-B (Butler et al., 1982), were discovered in attempts to develop pregnancy tests for livestock (Sasser et al., 1986; Zoli et al., 1991; Zoli et al., 1992a). Rabbits were injected with extracts of placental cotyledons, and antibodies not directed against placental antigens were removed by adsorption with tissue extracts from nonpregnant animals. The resulting antisera provided the basis of an accurate pregnancy test for cattle and sheep as early as one month post-insemination.

Xie et al. (1991) used an antiserum directed against purified boPAGs from cattle and from sheep to screen cDNA libraries from late placental tissue. The full-length cDNAs shared 86% nucleotide sequence identities with each other and a surprising 60% sequence identity to pepsinogens. The boPAGs had mutations in and around their active sites that would render them inactive as proteinases (Xie et al., 1991; Guruprasad et al., 1996). The similarities to pepsin A (~50% amino acid identity) and chymosin (~45%) in primary structure has allowed atomic models of ovine (ov)PAG1 and boPAG1 to be built (Guruprasad et al., 1996). Both molecules have the bibbed structure typical of all known eukaryotic aspartic proteinases and possess a cleft between the two lobes capable of accommodating peptides up to 7 amino acids long. Modeling strongly suggested that both ovPAG1 and boPAG1 can bind the pepsin inhibitor pepstatin, a prediction that has been validated.

Even in initial studies (Butler et al., 1982; Zoli et al., 1991; Xie et al., 1991; Xie et al., 1994; Xie et al., 1996), it was clear that the boPAGs were heterogenous in molecular weight and charge, and as more isoforms have been purified it has become evident that they differ in their amino terminal sequences (Atkinson et al., 1993; Xie et al., 1997a). Further library screening has revealed additional transcripts in ruminants (Xie et al., 1994; Xie et al., 1995; Xie et al., 1997b) and the existence of PAGs in non-ruminant species such as the pig (Szafranska et al., 1995), and the horse (Guruprasad et al., 1996).

Despite their apparent lack of proteolytic activity, all of the PAGs whose amino terminal sequences have been determined are proteolytically processed in a manner typical of other aspartic proteases such as pepsin (Davies, 1990). For example, a pro-peptide of most PAGs, which constitutes the first 38 amino acids of the secreted form and which normally folds into the active site region, has been cleaved from the secreted forms of PAG. Thus, the calculated molecular weight of the mature, non-glycosylated PAG, i.e. with signal sequence propeptide removed would be ~36,000 daltons and the circulating antigen in serum would also lack this segment. The observed molecular weight of secreted PAG, however, is much larger ranging from 45,000 daltons to 90,000 daltons (Xie et al., 1991; Sasser et al., 1989; Xie et al., 1996), probably due to extensive glycosylation (Holdsworth et al., 1982). Multiple boPAG genes in the bovine genome have most likely contributed to the triphasic alterations of PAG concentrations in maternal serum.

A. BoPAG1

Bovine (bo) PAG1 was initially identified as a unique placental antigen by raising antisera to total bovine placental extracts (Zoli et al., 1991). It is a product of binucleate trophoblast cells (Xie et al., 1991; Zoli et al., 1992b) which constitute the invasive component of the placenta (Wooding, 1992; Guillomot, 1995). In 1991, cDNA for both boPAG1 and ovine PAG1 was identified (ovPAG1) (Xie et al., 1991). Surprisingly, the PAG1 belong to the aspartic proteinase (AP) gene family, a grouping that includes pepsin, chymosin, renin, and cathepsin D and E (Guruprasad et al., 1996). Unlike other members of the AP family, both ovPAG1 and boPAG1 appear to be enzymatically inactive, since the catalytic domain in the active site region is mutated (Xie et al., 1991; Guruprasad et al., 1996).

BoPAG1 gene contains 9 exons and 8 introns (Xie et al., 1996), an identical organization to that of other mammalian aspartic genes. Southern genomic blotting with a probe encompassing exon 7 and exon 8, which represent the most conserved region of PAG relative to other AP, indicated that there were probably many PAG genes. In addition, when a bovine genomic library was probed with boPAG1 cDNA, 0.06% positive phage plaques were identified, suggesting that there may be 100 or more PAG genes in the bovine genome (Xie et al., 1995). This approximation has recently been confirmed by a variety of other approaches (Xie et al., 1997b).

Levels of boPAG1 or related molecules that cross-react with a boPAG-1 antiserum are very low around day 21 to day 27 (Warnick et al., 1995; Beal et al., 1992; Cameron and Malmo, 1993; Butler et al., 1982), are maintained at a higher, but still low concentration until about day 100 of the pregnancy and then rise quickly to ~100 ng/ml. The concentrations then remain relatively constant until the last quarter of pregnancy when they peak at 1 $\mu$g/ml of serum or greater right before parturition. One explanation for the triphasic profile of boPAG1 immunoreactivity is that expression of boPAG1 is very low in early pregnancy, rises considerably at mid gestation and peaks before parturition (Sasser et al., 1986; Zoli et al., 1992a; Patel et al., 1995). Alternatively, the presence of immunoreactive antigen in very early pregnancy may be due to the production of other boPAGs. The rise in the second trimester may reflect production of yet a different class of boPAG or possibly the initiation of low PAG1 expression. The exponential rise of boPAGs just prior to parturition could represent a sudden increase in the synthesis of one or more boPAG1 related molecules or increased "escape" across a leakier uteroplacental junction.

Immunocytochemistry and in situ hybridization analyses have shown that boPAG1 and ovPAG1, and their close relatives (since neither the antisera nor the probes are expected to be monospecific) are localized to binucleate cells (Xie et al., 1991; Zoli et al., 1992b) In contrast, the antigenically distinct boPAG2 is expressed in predominantly mononucleate cells of the trophectoderm (Xie et al., 1994). In the ruminants, binucleate cells are the invasive components of the trophoblast and do not appear until about day 13 in sheep and day 17 in cattle (Wooding, 1992). They then quickly increase in number. By day 21 in cattle they constitute up to 20% of cells in the trophectoderm, and a high percentage are actively fusing with maternal uterine epithelial cells (Wooding, 1992; King et al., 1980; Guillomot, 1995). Binucleate cell granules, which contain PAG1 (Zoli et al., 1992b), are discharged from the fusion cell towards the maternal stroma and its network of capillaries. Therefore, the binucleate cell products have ready access to the maternal circulation.

B. Novel OvPAG and BoPAG Species

Figure 1A:
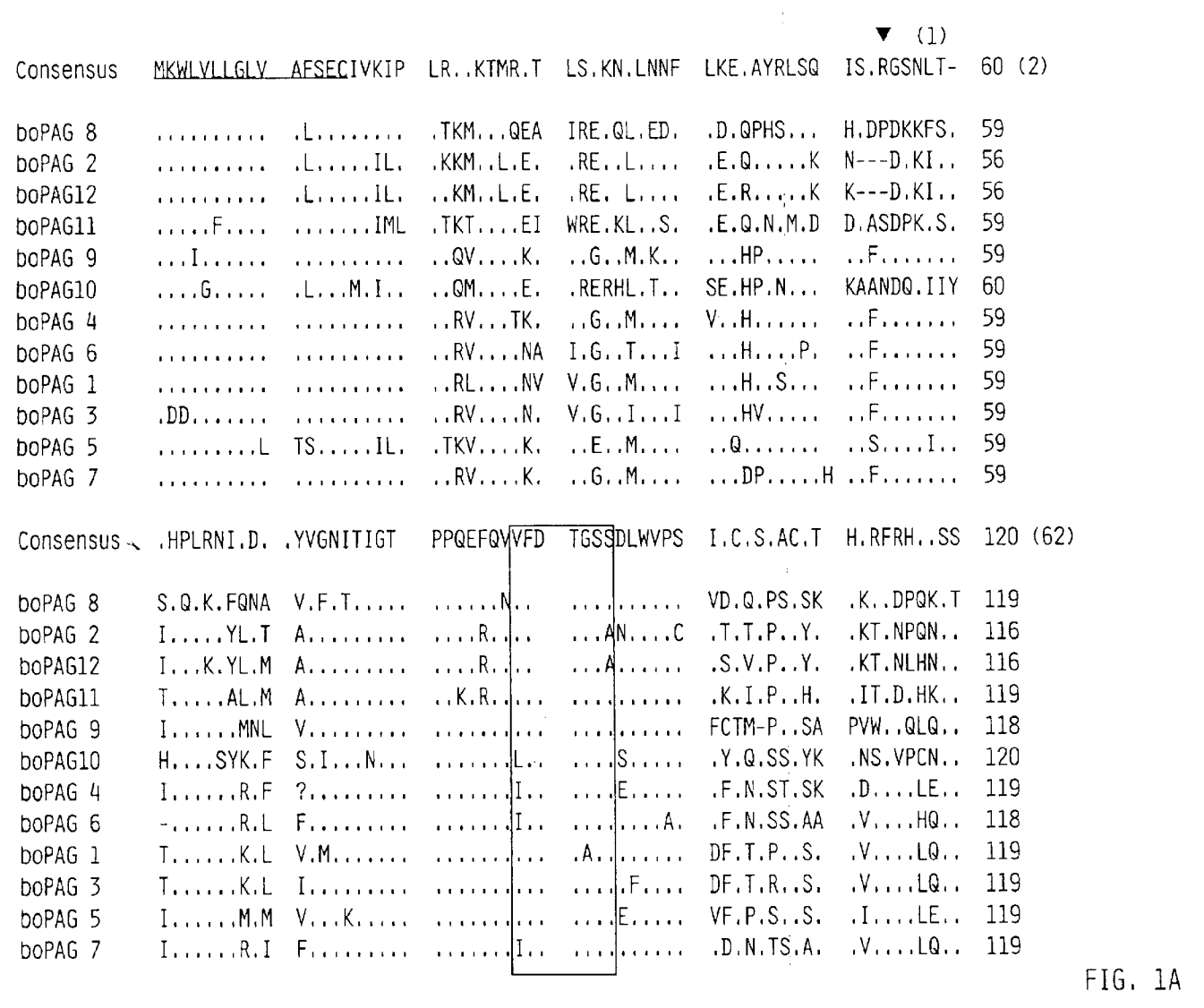
Figure 2A:
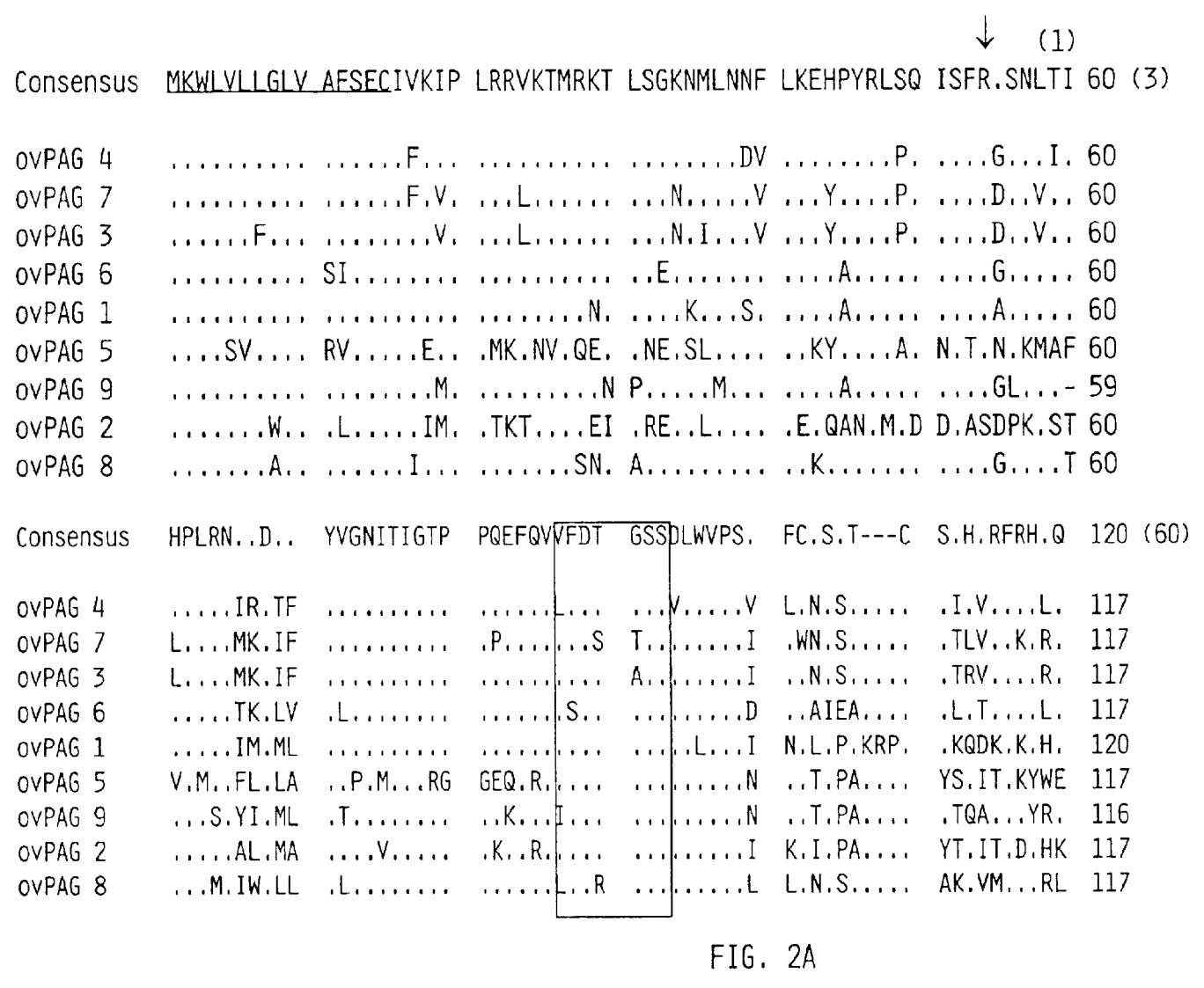

According to the present invention, cDNA for a series of novel boPAGs have been identified and cloned (FIG. 1). A similar large family of ovine (ov) PAGs have been identified from sheep placenta (Xie et al., 1991; Xie et al., 1997a; Xie et al., 1997b; FIG. 2). Certain of the boPAGs are useful in detection of early pregnancy in cattle. These molecules are homologous to, but different from, boPAG1 (Xie et al., 1991; FIG. 1; FIG. 3). The inventors now estimate that there are at least 100 PAG-related genes in cattle, and the inventors have already cloned and wholly or partially sequenced at least 20 distinct cDNA (including 10 complete cDNA from early pregnancy). Apparently, PAGs constitute a polymorphic group (Xie et al., 1994; Xie et al., 1995; Xie et al., 1997a; Xie et al., 1997b), whose members either show variable degrees of immunocrossreactivity or do not cross-react at all with the antisera that have been developed. Some of the cloned PAGs are only expressed in binucleate cells of the placenta (see Example 3). These cells are known to have an endocrine function (Wooding, 1992). They produce placental lactogen and steroids, for example. However, the functions of the PAG family members are unknown, although they enter the maternal circulation.

One important aspect of the present invention is that PAGs are not expressed uniformly throughout pregnancy (see Example 4). Some are found early in pregnancy, while are others are expressed in later stages. For example, PAGs that are expressed most strongly in the invasive binucleate cells at implantation are not dominant in late pregnancy. Conversely, boPAG1 (PSP-B) (Xie et al., 1991; Butler et al., 1982; Sasser et al., 1986) primarily is a product of binucleate cells of the late placenta, and antiserum raised against it fails to recognize the dominant PAG produced by binucleate cells in early pregnancy. Therefore, the test developed by the other groups and based on boPAG1/PSP-B/PSP60 (Butler et al., 1982; Sasser et al., 1986; Zoli et al., 1992a; Mialon et al., 1993; Kiracofe et al., 1994) is only marginally useful early in pregnancy because the antigen is produced in extremely small amounts, if at all, at that time. The expression pattern of boPAG1 also helps explain the concentration profile of the antigen measured in serum. At term, levels can exceed 5 μg/ml, while at day 40, when the development of the placenta in terms of size is almost complete, concentrations are around 10 ng/ml, i.e., 500-fold lower.

Certain of the novel boPAGs disclosed in this invention (boPAG4, 5, 6, 7, and 9), having the sequences of SEQ ID NO:27, SEQ ID NO:28, SEQ ID NO:29, SEQ ID NO:30, and SEQ ID NO:32 are present at day 25 of pregnancy. These PAGs are expressed in invasive binucleate cells which release their secretory granules into maternal uterine capillary bed (see Example 3). Of these five, boPAG4 appears to cross react with the late pregnancy PAG, boPAG1, which has been the basis of the earlier pregnancy test (see Example 1). By virtue of their early expression, these PAGs can be detected by conventional immunological techniques in physiological fluids of heifers or cows (especially in serum, urine, and milk) to detect the presence of a fetus or fetuses in the uterus prior to day 30 of pregnancy. Thus, the presence of these antigens provide a diagnostic test of early pregnancy in cattle.

Figure 6:
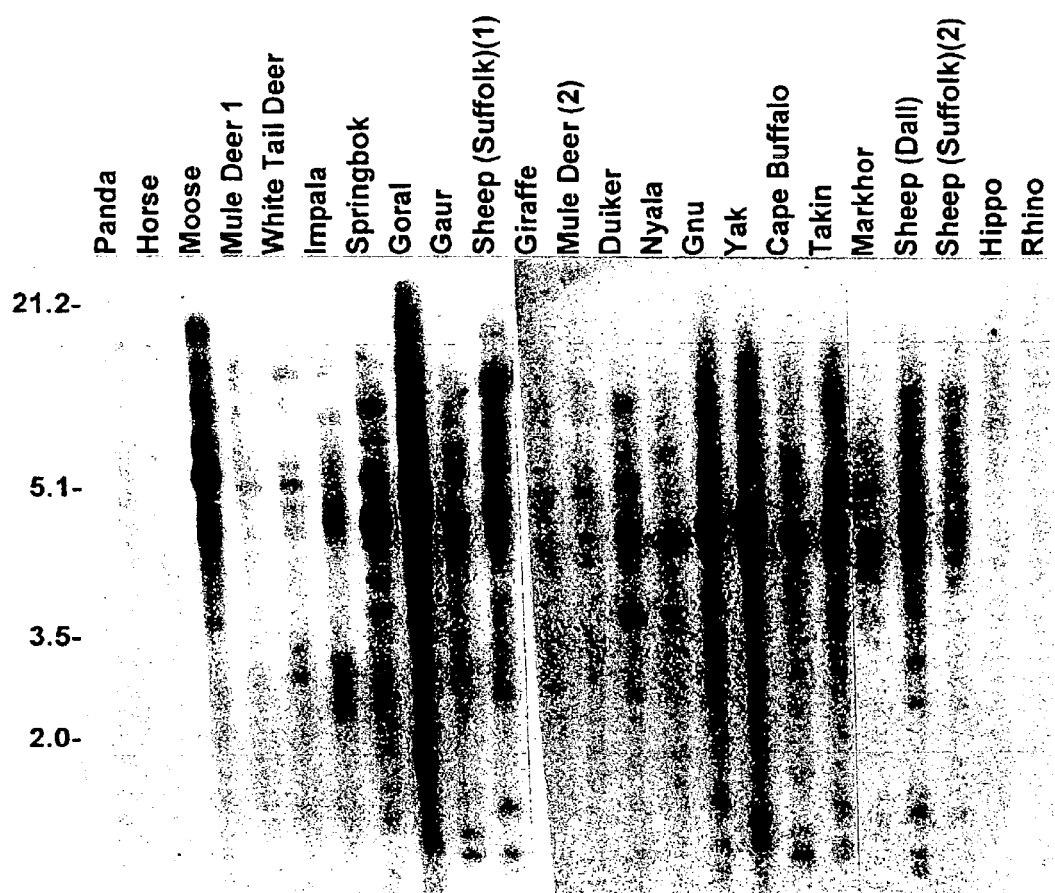
FIG. 6. Southern genomic blotting of DNA from some selected ruminant and nonruminant ungulate species and from a member of the family Carnivora (Panda). DNA was digested with EcoRI and probed with a boPAG1 probe. DNA size markers are on the left. Some samples of DNA, e.g., Suffolk Sheep and Mule Deer were analyzed twice.

Similar observations on the diversity of PAGs, the localization of different PAGs to either mononucleated and binucleated cells, and the likely varied timing of PAG expression have been noted in sheep (Xie et al., 1991; Xie et al., 1997a; Xie et al., 1997b). Because of the large number of genes noted in other species (FIG. 6) these observations are likely also to hold for other Artiodactyla, as well.

C. Structural, Functional and Evolutionary Aspects of PAGs

PAGs are members of the aspartic proteinase gene family (Xie et al., 1991; Xie et al., 1994; Xie et al., 1995), although the inventors do not believe they are necessarily active as proteolytic enzymes. cDNAs for these antigens (called pregnancy-associated glycoproteins or PAG) have been cloned from early placenta and expressed in a variety of systems in order to produce recombinant products.

The active aspartic proteinases, which include the various pepsins, chymosins, cathepsin E and D and renin, are clustered in the central branches of the tree. Included among them is eqPAG1, which is paired with rabbit pepsinogen F. EqPAG1 is an active proteinase after propeptide excision (Green et al., 1998) and may therefore be the horse homolog of pepsin F. Unfortunately little is known about pepsinogen F; it has been cloned from the stomach of a neonatal rabbit (Kageyama et al., 1990), but its overall expression pattern in the fetus has not been studied, nor has pepsinogen F been described in any other species.

BoPAG1 and 2 occupy an intermediate position between the enzymatically functional aspartic proteinases and the PAGs from cattle and sheep. Of the latter, boPAG8, boPAG10 and ovPAG5 are the three most distant and possibly most ancient gene products so far identified. Most closely related to them are ovPAG2 and boPAG2, 11 and 12. As determined by in situ hybridization analysis, their genes are expressed in both the mononucleated as well as the larger invasive binucleated cells of the outer trophectoderm layer of the placenta. The remaining PAG genes, ovPAG1, 3, 4, 6, 7, 8 and 9 and boPAG1, 3, 4, 5, 6, 7 and 9, which have diverged less than the grouping above, have strictly binucleate cell-specific expression. Because binucleate cells are a typical feature of the trophectoderm of the synepitheliochorial placentas of the pecoran ruminants (suborder: Ruminantia) (Wooding, 1992), it is tempting to speculate that the PAG1related genes diverged relatively recently.

If the entire PAG gene family arose by a series of relatively recent duplications during the diversification of the even toed ungulates (Artiodactyla), the expected lengths of the branches leading to the individual PAG might be expected to be relatively short. Instead many are long, far exceeding the distance between human, rabbit and rat cathepsin E (FIG. 8) whose divergence encompasses more than 100 million years of evolutionary time. There seem to be two alternative explanations. One is that the recent origin theory is wrong and that duplication of PAGs occurred early in the diversification of mammals. The second is that the genes duplicated late but accumulated mutations at a high rate. Early diversification seems unlikely in view of the fact that large numbers of aspartic proteinase gene family members have not been described in either rodents or man despite considerable efforts to clone them (Birch and Loh, 1991). The inventors' data for the horse (Perissodactyla) and cat (Carnivora) indicate only a limited number (and possibly only a single) expressed PAG gene in each species. Therefore, the inventors favor a late and rapid diversification of the PAG within the Artiodactyla. In this regard, the relatedness of ovPAG2 and boPAG11 (94% at the amino acid level) suggests they are functional homologs. These genes are the most closely related of all the PAGs shown in FIG. 8, despite a species separation of around 18 million years (Miyamoto et al., 1993).

An analysis (Nei, 1987; Li, 1993) of the nucleotide substitutions within the protein-coding regions of the PAG genes reveals that the ratio of synonymous (silent) mutations per synonymous site (Ks) to nonsynonymous (replacement) mutations per nonsynonymous site (Ka) in pairwise comparisons among all PAGs averages 1.18±0.27 (mean±S.D.). A closer examination indicates that within highly conserved regions the Ks to Ka ratio is high, while it is low in the hypervariable loop-encoding regions. For example, the Ks to Ka ratio averages 3.07±1.08 for the highly conserved 29 codons encoding the buried carboxyl end of the molecules. By contrast, the value for the preceding 21 codons, which are hypervariable and encode the two loops (291–296 and 281–287) shown in FIG. 5B, is 0.53±0.18. Thus, mutations that alter amino acids have accumulated faster than silent mutations.

Mutations that lead to amino acid changes are much more likely to be deleterious and therefore to be eliminated than synonymous changes. For this reason Ks/Ka ratios are generally greater than 2.0 (Ohta, 1992). The PAGs appear exceptional in this respect, with the data suggesting that their high variability has occurred as the result of positive selection. Other related aspartic proteinases, such as ovine and bovine chymosins, enzymes whose coding regions are 95% identical in sequence (Moir et al., 1982; Pungercar et al., 1990) despite 18 million years of separation (Miyamoto et al., 1993), exhibit a Ks to Ka ratio of 2.47, a value more than twice as high as the average PAG pair. The only PAG pair that exhibits a comparable value to the chymosins is ovPAG2 and boPAG1 I (ratio 2.92) proteins whose relatedness has been commented upon earlier (FIG. 8) and which may be functional homologs. Equine PAG and rabbit pepsinogen F, both active enzymes, provide a value of 2.61. Conceivably these genes have also acquired a function that is less able to tolerate changes in the surface loop regions than PAGs in general.

In a more general context, the evolution of multigene families has been the subject of several recent reviews (Ohta, 1995; Hughes, 1994; Fryxell, 1996). All agree that most duplicated genes are likely either to be quickly lost or accumulated as pseudogenes, as a result of "purifying" Darwinian selection, unless they acquire a novel function. By this argument it must be assumed that individual PAGs are not only functional molecules, but that each has a subtly different role. Hughes (1994) has argued that weak bifunctionality must be acquired prior to gene duplication and that, once duplicated, genes become separated by a burst of amino acid replacements that allows a specific function to become fixed and enhanced. These mutations are likely to be acquired by a combination of nonsynonymous point mutations, and by gene conversion events which can probably occur readily between closely linked, structurally similar genes (Ohta, 1995). Genetic drift and natural selection will ensure the retention of those mutations that are not deleterious. At present it is not possible to estimate what kinds of mutational changes contributed most to PAG diversity.

Fryxell (1996) has argued that the retention of a duplicated gene will in general, require the presence of a preexisting or similarly evolving family of complementary molecules with which the products of the duplicated genes can interact. Among the best known rapidly evolving gene families are immunoglobulins, T cell receptors and MHC antigens, the cytochrome p450 system and the odorant receptors. In each of these cases, diversification is linked to a more exacting capacity to bind particular ligands. For the PAGs, it is tempting to speculate that their function relates to their peptide-binding capabilities, although a function involving some structural feature other than the cleft, such as the propeptide or carbohydrate, cannot be ruled out. Even though the regions around the two catalytic aspartyl residues are generally conserved in all aspartic proteinases (Davis, 1990; Takahashi et al., 1995), substitutions elsewhere can markedly influence what peptides gain access to the catalytic center, clearly evident when the exceedingly narrow substrate specificity of renin is compared with that of pepsin A. The reorganization of the combining site of an antibody against a nitrophenyl phosphate hapten as it evolved from its gernline precursor led to a 30,000-fold greater affinity for ligand and involved only a handful of amino acids, many of which were in a surface location and none of which made direct contact with the ligand (Wedemayer et al., 1997). Small additive changes in the packing of loops provided a combining site able to lock in the hapten with much greater efficiency. Similar events could presumably modify the peptide-binding cleft of PAGs and provide molecules with a considerable range of specificities.

D. Variants of PAGS

It is contemplated that, for various uses, variants of PAGs can be utilized according to the present invention. These changes may improve stability or function, for example, antigenicity or immunoreactivity. It may be desirable to create substitutional, insertional or deletion variants or fusion proteins from the identified PAGs. Deletion variants lack one or more residues of the native protein. Insertional mutants typically involve the addition of material at a non-terninal point in the polypeptide. This may include the insertion of an immunoreactive epitope or simply a single residue. Terminal additions, are fusion proteins. Substitutional variants typically contain the exchange of one amino acid for another at one or more sites within the protein, and may be designed to modulate one or more properties of the polypeptide, such as stability against proteolytic cleavage, without the loss of other functions or properties. Substitutions of this kind may be termed "conservative," that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological ftnctional activity, certain amino acid substitutions can be made in a protein sequence, and its underlying DNA coding sequence, and nevertheless obtain a protein with like properties. It is thus contemplated by the inventors that various changes may be made in the DNA sequences of genes without appreciable loss of their biological utility or activity, as discussed below. Table 1 shows the codons that encode particular amino acids.

Another embodiment for the preparation of polypeptides according to the invention is the use of peptide mimetics. Mimetics are peptide-containing molecules that mimic elements of protein secondary structure. See, for example, Johnson et al., "Peptide Turn Mimetics" in *BIOTECHNOLOGY AND PHARMACY*, Pezzuto et al., Eds., Chapman and Hall, New York (1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used, in conjunction with the principles outline above, to engineer second generation molecules having many of the natural properties of PAGs, but with altered and even improved characteristics.

E. Purification of the Proteins

It will be desirable to purify the various PAGs identified by the inventors or variants thereof. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number" (i.e., 2-fold, 5-fold, 10-fold, 50-fold, 100-fold, 1000-fold, etc.). The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat or acid pH denaturation of contaminating proteins, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE and according to how extensively it is glycosylated (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of min, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and Helix pomatia lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

F. Synthetic Peptides

The present invention also describes portions of PAG-related peptides for use in various embodiments of the present invention. Because of their relatively small size, the peptides of the invention can also be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979), each incorporated herein by reference. Short peptide sequences, or libraries of overlapping peptides, usually from about 6 up to about 35 to 50 amino acids, which correspond to the selected regions described herein, can be readily synthesized and then screened in screening assays designed to identify reactive peptides. Alternatively, recombinant DNA technology may be employed wherein a nucleotide sequence which encodes a peptide of the invention is inserted into an expression vector, transformed or transfected into an appropriate host cell and cultivated under conditions suitable for expression.

G. Antigen Compositions

The present invention provides for the use of PAGs or peptides as antigens for the generation of polyclonal antisera and monoclonal antibodies for use in the detection of pregnancy. It is envisioned that some variant of a PAG, or portions thereof, will be coupled, bonded, bound, conjugated or chemically-linked to one or more agents via linkers, polylinkers or derivatized amino acids. This may be performed such that a bispecific or multivalent composition or vaccine is produced. It is further envisioned that the methods used in the preparation of these compositions will be familiar to those of skill in the art and should be suitable for administration to animals, i.e., pharmaceutically acceptable. Preferred agents are the carriers such as keyhole limpet hemocyannin (KLH) or glutathione-S-transferase.

In order to formulate PAGs for immunization, one will generally desire to employ appropriate salts and buffers to render the polypeptides stable. Aqueous compositions of the present invention comprise an effective amount of the PAG antigen to the host animal, dissolved or dispersed in a pharmaceutically acceptable carrier or aqueous medium. Such compositions may be referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the vectors or cells of the present invention, its use in therapeutic compositions is contemplated. Supplementary active ingredients also can be incorporated into the compositions.

The compositions of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, described supra.

The PAGs also may be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It should be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases; it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the PAGs in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCi solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, preparations should meet applicable sterility, pyrogenicity, general safety and purity standards.

III. Nucleic Acids

A. PAG-Encoding Sequences

The present invention provides, in another embodiment, genes encoding the various PAG polypeptides. Specifically, those encoding PAG2, PAG4, PAG5, PAG6, PAG7, and PAG9 are envisioned. Those nucleic acid sequences encoding the proteins having the sequences of SEQ ID NO:25; SEQ ID NO:27; SEQ ID NO:28; SEQ ID NO:29; SEQ ID NO:30; and SEQ ID NO:32 are encompassed by the present invention, as are those polynucleotides disclosed in SEQ ID NO:2; SEQ ID NO:4; SEQ ID NO:5; SEQ ID NO:6; SEQ ID NO:7; and SEQ ID NO:9. The present invention is not limited in scope to these genes, however, as one of ordinary skill in the art could, using these nucleic acids, readily identify related PAGs in various other species.

In addition, it should be clear that the present invention is not limited to the specific nucleic acids disclosed herein. As discussed below, a given "PAG gene" may contain a variety of different bases and yet still produce a corresponding polypeptide that is functionally (i.e., antigenically, immunologically), and in some cases structurally, indistinguishable from the genes disclosed herein.

Similarly, any reference to a nucleic acid should be read as encompassing a host cell containing that nucleic acid and, in some cases, capable of expressing the product of that nucleic acid. In addition to therapeutic considerations, cells expressing nucleic acids of the present invention may prove useful in the context of screening for agents that induce, repress, inhibit, augment, interfere with, block, abrogate, stimulate or enhance the detectability of PAGs.

Nucleic acids according to the present invention may encode an entire PAG gene, a domain of a PAG that contains a relevant epitope, or any other fragment of the PAG sequences set forth herein. The nucleic acid may be derived from genomic DNA, i.e., cloned directly from the genome of a particular organism. In preferred embodiments, however, the nucleic acid would comprise complementary DNA (cDNA). At a minimum, these and other nucleic acids of the present invention may be used as molecular weight standards in, for example, gel electrophoresis.

The term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There may be times when the full or partial genomic sequence is preferred. It also is contemplated that a given PAG from a given species may be represented by natural variants that have slightly different nucleic acid sequences but, nonetheless, encode the same protein (see Table 1).

As used in this application, the term "a nucleic acid encoding a PAG" refers to a nucleic acid molecule that has been isolated free of total cellular nucleic acid. In preferred embodiments, the invention concerns a nucleic acid sequence essentially as set forth in for example, SEQ ID NO:25; SEQ ID NO:27; SEQ ID NO:28; SEQ ID NO:29; SEQ ID NO:30; or SEQ ID NO:32. The term "as set forth in, for example, SEQ ID NO:25; SEQ ID NO:27; SEQ ID NO:28; SEQ ID NO:29; SEQ ID NO:30; or SEQ ID NO:32" means that the nucleic acid sequence substantially corresponds to a portion of SEQ ID NO:25; SEQ ID NO:27; SEQ ID NO:28; SEQ ID NO:29; SEQ ID NO:30; or SEQ ID NO:32 respectively. The term "functionally equivalent codon" is used herein to refer to codons that encode the same amino acid, such as the six codons for arginine or serine (Table 1), and also refers to codons that encode biologically equivalent amino acids, as discussed in the following pages.

TABLE 1

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |

TABLE 1-continued

| Amino Acids | | | Codons |
|---|---|---|---|
| Valine | Val | V | GUA GUC GUG GUU |
| Tryptophan | Trp | W | UGG |
| Tyrosine | Tyr | Y | UAC UAU |

Allowing for the degeneracy of the genetic code, sequences that have at least about 50%, usually at least about 60%, more usually about 70%, most usually about 80%, preferably at least about 90% and most preferably about 95% of nucleotides that are identical to the nucleotides of FIG. 1 will be sequences that are "as set forth in FIG. 1." Sequences that are essentially the same as those set forth in FIG. 1 may also be functionally defined as sequences that are capable of hybridizing to a nucleic acid segment containing the complement of FIG. 1 under standard conditions.

Naturally, the present invention also encompasses DNA segments that are complementary, or essentially complementary, to the sequence set forth in FIG. 1. Nucleic acid sequences that are "complementary" are those that are capable of base-pairing according to the standard Watson-Crick complementary rules. As used herein, the term "complementary sequences" means nucleic acid sequences that are substantially complementary, as may be assessed by the same nucleotide comparison set forth above, or as defined as being capable of hybridizing to the nucleic acid segment of SEQ ID NO:2; SEQ ID NO:4; SEQ ID NO:5; SEQ ID NO:6; SEQ ID NO:7; or SEQ ID NO:9 under relatively stringent conditions such as those described herein. Such sequences may encode the entire PAGs encompassed herein or finctional or non-functional fragments thereof.

B. PAG-Encoding Fragments

Alternatively, the hybridizing segments may be shorter oligonucleotides. Sequences of 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that exemplary oligonucleotides of 8, 9, 10, 11, 12, 13, 14, 15, 16, 17, 18, 19, 20, 25, 30, 35, 40, 45, 50, 55, 60, 65, 70, 75, 80, 85, 90, 95, 100 or more base pairs will be used, although others are contemplated. Longer polynucleotides are contemplated as well. Such oligonucleotides will find use, for example, as probes in Southern and Northern blots and as primers in amplification reactions. These reagents are particularly useful in identifying structurally related PAGs.

Suitable hybridization conditions will be well known to those of skill in the art. In certain applications, for example, substitution of amino acids by site-directed mutagenesis, it is appreciated that lower stringency conditions are required. Under these conditions, hybridization may occur even though the sequences of probe and target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated, and thus will generally be a method of choice depending on the desired results.

In other embodiments, hybridization may be achieved under conditions of, for example, 50 mM Tris-HCl (pH 8.3), 75 mM KCl, 3 mM $MgCl_2$, 10 mM dithiothreitol, at temperatures between approximately 20° C. to about 37° C. Other hybridization conditions utilized could include approximately 10 mM Tris-HCl (pH 8.3), 50 mM KCl, 1.5 $\mu$M $MgCl_2$, at temperatures ranging from approximately 40° C. to about 72° C. Formamide and SDS also may be used to alter the hybridization conditions.

As stated above, one method of using probes and primers of the present invention is in the search for genes related to the PAG encompassed in the instant invention or, more particularly, homologs of PAG from other species. The existence of a variety of homologies strongly suggests that other homologs will be discovered in additional species. Normally, the target DNA will be a genomic or cDNA library, although screening may involve analysis of RNA molecules. By varying the stringency of hybridization, and the region of the probe, different degrees of homology may be discovered.

Another way of exploiting probes and primers of the present invention is in site-directed, or site-specific mutagenesis. Site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

C. Vectors for Cloning, Gene Transfer and Expression

Within certain embodiments, expression vectors may be utilized to produce PAGs which can then be purified and, for example, be used to generate antisera or monoclonal antibody with which further studies may be conducted. Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

Throughout this application, the term "expression construct" is meant to include any type of genetic construct containing a nucleic acid coding for a gene product in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding a gene of interest.

In preferred embodiments, the nucleic acid encoding a gene product is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene. Typically, the promoter is selected for high level expression, such as lac inducible promoter for use in *E. coli*, alcohol oxidase for yeast, CMV IE for various mammalian systems, or the polyhedron promoter for Baculovirus. Other elements include polyadenylation signals, origins of replication, internal ribosome entry sites (IRES) and selectable markers (e.g., neomycin, puromycin, hygromycin, DHFR, GPT, zeocin and histidinol).

Transfer of expression constructs into cells also is contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988).

In certain embodiments of the invention, the expression construct comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). Retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins, making them attractive candidates for transformation of cells. Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

In a further embodiment of the invention, the expression construct (and PAGs) may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991).

IV. Generating Antibodies Reactive with PAGs

In another aspect, the present invention contemplates an antibody that is immunoreactive with a PAG molecule of the present invention, or any portion thereof. An antibody can be a polyclonal or a monoclonal antibody composition, both of which are preferred embodiments of the present invention. Means for preparing and characterizing antibodies are well known in the art (see, e.g., Harlow and Lane, 1988).

Briefly, a polyclonal antibody is prepared by immunizing an animal with an immunogen comprising a peptide or polypeptide of the present invention and collecting antisera from that immunized animal. A wide range of animal species can be used for the production of antisera. Typically an animal used for production of anti-antisera is a non-human animal including rabbits, mice, rats, hamsters, pigs or horses. Because of the relatively large blood volume of rabbits, a rabbit is a preferred choice for production of polyclonal antibodies.

Antibodies, both polyclonal and monoclonal, specific for isoforms of antigen may be prepared using conventional immunization techniques, as will be generally known to those of skill in the art. A composition containing antigenic epitopes of the compounds of the present invention can be used to immunize one or more experimental animals, such as a rabbit or mouse, which will then proceed to produce specific antibodies against the compounds of the present invention. Polyclonal antisera may be obtained, after allowing time for antibody generation, simply by bleeding the animal and preparing serum samples from the whole blood.

It is proposed that the monoclonal antibodies of the present invention will find useful application in standard immunochemical procedures, such as ELISA and Western blot methods and in immunohistochemical procedures such as tissue staining, as well as in other procedures which may utilize antibodies specific to PAG-related antigen epitopes. Additionally, it is proposed that monoclonal antibodies specific to the particular PAG of different species may be utilized in other useful applications.

In general, both polyclonal and monoclonal antibodies against PAG may be used in a variety of embodiments. For example, they may be employed in antibody cloning protocols to obtain cDNAs or genes encoding other PAG polypeptides. They may also be used in inhibition studies to analyze the effects of PAG related peptides in cells or animals. Anti-PAG antibodies will also be useful in immunolocalization studies to analyze the distribution of PAG polypeptides during various cellular events, for example, to determine the cellular or tissue-specific distribution of PAG polypeptides under different points in the cell cycle. A particularly useful application of such antibodies is in purifying native or recombinant PAG, for example, using an antibody affinity column. The operation of all such immunological techniques will be known to those of skill in the art in light of the present disclosure.

Means for preparing and characterizing antibodies are well known in the art (see, e.g., Harlow and Lane, 1988; incorporated herein by reference). More specific examples of monoclonal antibody preparation are give in the examples below.

As is well known in the art, a given composition may vary in its immunogenicity. It is often necessary therefore to boost the host immune system, as may be achieved by coupling a peptide or polypeptide immunogen to a carrier.

Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimide and bis-biazotized benzidine.

As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate mAbs.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified PAG. The immunizing composition is administered in a manner effective to stimulate antibody producing cells. Rodents such as mice and rats are preferred animals, however, the use of rabbit, sheep or frog cells is also possible. The use of rats may provide certain advantages (Goding, 1986), but mice are preferred, with the BALB/c mouse being most preferred as this is most routinely used and generally gives a higher percentage of stable fusions.

Following immunization, somatic cells with the potential for producing antibodies, specifically B-lymphocytes (B-cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, 1986; Campbell, 1984). For example, where the immunized animal is a mouse, one may use P3-X63/Ag8, P3-X63-Ag8.653, NS1/l.Ag 4 l Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with cell fusions.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler and Milstein, 1975; 1976), and those using polyethylene glycol (PEG), such as 37% (v/v) PEG, by Gefter et al., (1977). The use of electrically induced fusion methods is also appropriate (Goding, 1986).

Fusion procedures usually produce viable hybrids at low frequencies, around $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

V. Assays for PAG Expression in the Detection of Pregnancy

According to the present invention, the present inventors have determined that certain PAGs are advantageously expressed in early stages of pregnancy and, therefore, can be used as markers in the detection of pregnancy at an early stage. While the present invention is exemplifed in cattle, its extension to other species including sheep (e.g. deer, antelopes, and giraffes), horses (Perissodactyla), and all other ruminant ungulates and even more distantly related species (dogs, cats, humans) is contemplated. In addition, the immunoassays, may be qualitative or quantitative.

In cattle, the boPAGs may be used individually or in combination to provide a diagnostic evaluation of pregnancy. According to the present invention, these boPAGs include BoPAG2, BoPAG4, BoPAGS, BoPAG6, BoPAG7, BoPAG9, boPAG7v; boPAG9v; boPAG15; boPAG16; boPAG17; boPAG18; boPAG19; boPAG20 or boPAG21. Other boPAGs, and PAGs from other species, may prove useful, alone or in combination, for similiar purposes.

A. Immunologic Detection of Pregnancy

The present invention entails the use of antibodies in the immunologic detection of PAGs. Various useful immunodetection methods have been described in the scientific literature, such as, e.g., Nakamura et al. (1987; incorporated herein by reference). Immunoassays, in their most simple and direct sense, are binding assays. Certain preferred immunoassays are the various types of enzyme linked immunosorbent assays (ELISAs) and radioimmunoassays (RIA). Immunohistochemical detection using tissue sections also is particularly useful. However, it will be readily appreciated that detection is not limited to such techniques, and Western blotting, dot blotting, FACS analyses, and the like also may be used in connection with the present invention.

In general, immunobinding methods include obtaining a sample suspected of containing a protein, peptide or antibody, and contacting the sample with an antibody or protein or peptide in accordance with the present invention, as the case may be, under conditions effective to allow the formation of immunocomplexes. Preferred samples, according to the present invention, are fluids, such as milk, urine, blood, serum or saliva.

Contacting the chosen biological sample with the protein, peptide or antibody under conditions effective and for a period of time sufficient to allow the formation of immune complexes (primary immune complexes) is generally a matter of simply adding the composition to the sample and incubating the mixture for a period of time long enough for the antibodies to form immune complexes with PAGs. After this time, the PAG-antibody mixture will be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any radioactive, fluorescent, biological or enzymatic tags or labels of standard use in the art. U.S. Patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody or a biotin/avidin ligand binding arrangement, as is known in the art.

Usually, the primary immune complexes may be detected by means of a second binding ligand that has binding affinity for the PAG or the PAG-specific first antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the PAG or anti-PAG antibody is used to form secondary immune complexes, as described above. The second binding ligand contains an enzyme capable of processing a substrate to a detectable product and, hence, amplifying signal over time. After washing, the secondary immune complexes are contacted with substrate, permitting detection.

B. ELISA

As a part of the practice of the present invention, the principles of an enzyme-linked immunoassay (ELISA) may be used. ELISA was first introduced by Engvall and Perlmann (1971) and has become a powerful analytical tool using a variety of protocols (Engvall, 1980; Engvall, 1976; Engvall, 1977; Gripenberg et al., 1978; Makler et al., 1981; Sarngadharan et al., 1984). ELISA allows for substances to be passively adsorbed to solid supports such as plastic to enable facile handling under laboratory conditions. For a comprehensive treatise on ELISA the skilled artisan is referred to "ELISA; Theory and Practise" (Crowther, 1995 incorporated herein by reference).

The sensitivity of ELISA methods is dependent on the turnover of the enzyme used and the ease of detection of the product of the enzyme reaction. Enhancement of the sensitivity of these assay systems can be achieved by the use of fluorescent and radioactive substrates for the enzymes. Immunoassays encompassed by the present invention include, but are not limited to those described in U.S. Pat. No. 4,367,110 (double monoclonal antibody sandwich assay) and U.S. Pat. No. 4,452,901 (western blot). Other assays include immunoprecipitation of labeled ligands and immunocytochemistry, both in vitro and in vivo.

In a preferred embodiment, the invention comprises a "sandwich" ELISA, where anti-PAG antibodies are immobilized onto a selected surface, such as a well in a polystyrene microtiter plate or a dipstick. Then, a test composition suspected of containing PAGs, e.g., a clinical sample, is contacted with the surface. After binding and washing to remove non-specifically bound immunocomplexes, the bound antigen may be detected by a second antibody to the PAG.

In another exemplary ELISA, polypeptides from the sample are immobilized onto a surface and then contacted with the anti-PAG antibodies. After binding and washing to remove non-specifically bound immune complexes, the bound antibody is detected. Where the initial antibodies are linked to a detectable label, the primary immune complexes may be detected directly. Alternatively, the immune complexes may be detected using a second antibody that has binding affinity for the first antibody, with the second antibody being linked to a detectable label.

Another ELISA in which the PAGs are immobilized involves the use of antibody competition in the detection. In this ELISA, labeled antibodies are added to the wells, allowed to bind to the PAG, and detected by means of their label. The amount of PAG in a sample is determined by mixing the sample with the labeled antibodies before or during incubation with coated wells. The presence of PAG in the sample acts to reduce the amount of antibody available for binding to the well, and thus reduces the ultimate signal.

Irrespective of the format employed, ELISAs have certain features in common, such as coating, incubating or binding, washing to remove non-specifically bound species, and detecting the bound immune complexes. In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the control human cancer and/or clinical or biological sample to be tested under conditions effective to allow immune complex (antigen/antibody) formation. Detection of the immune complex then requires a labeled secondary binding ligand or antibody, or a secondary binding ligand or antibody in conjunction with a labeled tertiary antibody or third binding ligand.

"Under conditions effective to allow immune complex (antigen/antibody) formation" means that the conditions preferably include diluting the antigens and antibodies with solutions such as BSA, bovine gamma globulin (BGG), evaporated or powdered milk, and phosphate buffered saline (PBS)/Tween. These added agents also tend to assist in the reduction of nonspecific background.

The "suitable" conditions also mean that the incubation is at a temperature and for a period of time sufficient to allow effective binding. Incubation steps are typically from about 1 h to 2 h to 4 h, at temperatures preferably on the order of 25° C. to 27° C., or may be overnight at about 4° C. or so.

To provide a detecting means, the second or third antibody will have an associated label to allow detection. Preferably, this will be an enzyme that will generate color development upon incubating with an appropriate chromogenic substrate. Thus, for example, one will desire to contact and incubate the first or second immune complex with a urease, glucose oxidase, alkaline phosphatase or hydrogen peroxidase-conjugated antibody for a period of time and under conditions that favor the development of further immunecomplex formation (e.g., incubation for 2 h at room temperature in a PBS-containing solution such as PBS-Tween).

After incubation with the labeled antibody, and subsequent to washing to remove unbound material, the amount of label is quantified, e.g., by incubation with a chromogenic substrate such as urea and bromocresol purple or 2,2'-azido-di-(3-ethylbenzthiazoline-6-sulfonic acid [ABTS] and $H_2O_2$, in the case of peroxidase as the enzyme label. Quantitation is then achieved by measuring the degree of color generation, e.g., using a visible spectra spectrophotometer.

A variant of ELISA is the enzyme-linked coagulation assay, or ELCA (U.S. Pat. No. 4,668,621), which uses the coagulation cascade combined with the labeling enzyme RVV-XA as a universal detection system. The advantage of this system for the current invention, is that the coagulation reactions can be performed at physiological pH in the presence of a wide variety of buffers. It is therefore possible to retain the integrity of complex analytes.

C. Immunohistochemistry

While primarily useful in research contexts, immunohistochemistry may be useful according to the present invention in identifying new PAGs. This involves testing of both fresh-frozen and formalin-fixed, paraffin-embedded tissue blocks prepared from study by immunohistochemistry (IHC). For example, each tissue block consists of 50 mg of residual "pulverized" placental tissue. The method of preparing tissue blocks from these particulate specimens has been successfully used in previous IHC studies of various prognostic factors, e.g., in breast, and is well known to those of skill in the art (Brown et al., 1990; Abbondanzo et al., 1990; Allred et al., 1990).

Briefly, frozen-sections may be prepared by rehydrating 50 ng of frozen "pulverized" placental tissue at room temperature in phosphate buffered saline (PBS) in small plastic capsules; pelleting the particles by centrifugation; resuspending them in a viscous embedding medium (OCT); inverting the capsule and pelleting again by centrifugation; snap-freezing in −70° C. isopentane; cutting the plastic capsule and removing the frozen cylinder of tissue; securing the tissue cylinder on a cryostat microtome chuck; and cutting 25–50 serial sections containing an average of about 500 remarkably intact placental cells.

Permanent-sections may be prepared by a similar method involving rehydration of the 50 mg sample in a plastic microfuge tube; pelleting; resuspending in 10% formalin for 4 h fixation; washing/pelleting; resuspending in warm 2.5% agar; pelleting; cooling in ice water to harden the agar; removing the tissue/agar block from the tube; infiltrating and embedding the block in paraffin; and cutting up to 50 serial permanent sections.

D. Immunodetection Kits

In further embodiments, the invention provides immunological kits for use in detecting PAGs in biological samples. Such kits will generally comprise one or more PAGs or PAG-binding proteins that have immunospecificity for various PAGs and for antibodies. More specifically, the immunodetection kits will thus comprise, in suitable container means, one or more PAGs, antibodies that bind to PAGs, and antibodies that bind to other antibodies via Fc portions.

In certain embodiments, the PAG or primary anti-PAG antibody may be provided bound to a solid support, such as a column matrix or well of a microtitre plate. Alternatively, the support may be provided as a separate element of the kit.

The immunodetection reagents of the kit may include detectable labels that are associated with, or linked to, the given antibody or PAG itself. Detectable labels that are associated with or attached to a secondary binding ligand are also contemplated. Such detectable labels include chemilluminescent or fluorescent molecules (rhodamine, fluorescein, green fluorescent protein, luciferase), radiolabels ($^3$H, $^{35}$S, $^{32}$P, $^4$C, $^{131}$I) or enzymes (alkaline phosphatase, horseradish peroxidase).

The kits may further comprise suitable standards of predetermined amounts, including both antibodies and PAGs. These may be used to prepare a standard curve for a detection assay.

The kits of the invention, regardless of type, will generally comprise one or more containers into which the biological agents are placed and, preferably, suitable aliquoted. The components of the kits may be packaged either in aqueous media or in lyophilized form.

The container means of the kits will generally include at least one vial, test tube, flask, bottle, or even syringe or other container means, into which the antibody or antigen may be placed, and preferably, suitably aliquoted. Where a second or third binding ligand or additional component is provided, the kit will also generally contain a second, third or other additional container into which this ligand or component may be placed.

The kits of the present invention will also typically include a means for containing the antibody, PAG and any other reagent containers in close confinement for commercial sale. Such containers may include injection or blow-molded plastic containers into which the desired vials are retained.

VI. Methods for Identifying Additional PAGs

By following the basic teachings of the examples, it will be possible to identify additional PAGs and, further, correlate their expression with early and late stage pregnancy. This is done by obtaining various tissues (e.g., placenta) as described in the examples and detecting the presence of various PAG transcripts therein. One of the best known nucleic acid amplification methods is the polymerase chain reaction (referred to as PCR™) which is described in detail in U.S. Pat. Nos. 4,683,195, 4,683,202 and 4,800,159, and in Innis et al., 1990, each of which is incorporated herein by reference in its entirety. These methods may be applied directly to the identification of PAGs.

Briefly, in PCR™, two primer sequences are prepared that are complementary to regions on opposite complementary strands of the marker sequence. An excess of deoxynucleoside triphosphates are added to a reaction mixture along with a. DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

Where transcripts are the nucleic acid sample of interest, a reverse transcriptase (RT)-PCR™ amplification procedure may be performed in order to convert the mRNA transcript to DNA and then amplify it for detection or cloning. Methods of reverse transcribing RNA into cDNA are well known and described in Sambrook et al., 1989. Alternative methods for reverse transcription utilize thermostable, RNA-dependent DNA polymerases. These methods are described in WO 90/07641 filed Dec. 21, 1990. Polymerase chain reaction methodologies are well known in the art.

Using PAG-related sequences as primers for either reverse transcription or for amplification, one may selectively amplify PAGs from these samples. Alternatively, one may simply create a cDNA library and screen the library using standard probing formats (e.g., Southern blotting). Identified clones may then be sequenced. Partial clones coding for less than a full length transcripts can, in turn, be used to isolate the complete sequence from other cDNA or even genomic libraries.

VII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

A. Example 1

Cloning of boPAGs from Placental Tissues Early in Pregnancy

Materials and Methods: Bovine PAG transcripts were cloned from day 19 and 25 placentae. RNA from six (Simmunental×Hereford) placentas at day 25 of pregnancy was used to construct a cDNA library in λZAPII (Clontech, Palo Alto, Calif.). The library was screened with a mixed probe of $^{32}$P-labeled bovine, ovine and porcine PAG1 and PAG2, and equine PAG cDNA (Xie et al., 1991, Xie et al., 1994; Xie et al., 1995; Szafranska et al., 1995). The positive clones were isolated and analyzed for the size of inserts by PCR™ and restriction endonuclease digestion. Sixteen clones of the expected length were partially sequenced. The second screening identified boPAG transcripts that reacted with an anti-boPAG1 antiserum (Zoli et al., 1991; Xie et al., 1991). Duplicate filter screening was employed to increase the frequency of isolation of full length clones. The first filter was allowed to react with antiserum to identify immunopositive clones (Xie et al., 1991), while the second filter was hybridized with a $^{32}$P-labeled probe corresponding to exons1 and 2 of boPAG1, ovPAG1 and ovPAG2. The clones positive on both filters were purified and partially sequenced.

PAG transcripts from a day 19 trophoblast of a Holstein cow were cloned by reverse transcription (RT) and PCR™ procedures. Cellular RNA, extracted from day 19 trophoblast, was first reverse transcribed into cDNA then amplified by PCR™ with a pair of well-conserved primers (boPAGexp3'5' CCCAAGCTTATGAAGTGGCTTGT-GCTCCT3' (SEQ ID NO:16), and boPAGexp3' 5'GGGAAGCTTACTTGTCATCGTCGTCCT-TGTAGTCGGTACCCACCTGTGCCAG GCCAATCCT-GTCATTTC3' (SEQ ID NO:17). The RT-PCR™ products were cloned into TA cloning vectors (Invitrogen, CA USA). All the novel boPAG cDNAs were fully sequenced.

Results: Alignment of amino acid sequences of all boPAG available is shown in FIG. 1. BoPAG1, 2 and 3 have been identified previously at Day 260 of pregnancy, i.e., close to term (Xie et al., 1991; Xie et al., 1994; Xie et al., 1995) and are, therefore, "late" PAGs. Transcripts for boPAGs 4, 5, 6, 7, 8, 9, 10 and bo PAG11 (SEQ ID NO:4; SEQ ID NO:5; SEQ ID NO:6; SEQ ID NO:7; SEQ ID NO:8; SEQ ID NO:9; SEQ ID NO:10; SEQ ID NO:11) were all present in the day 25 library (FIG. 3). BoPAG12 (SEQ ID NO:12) was present in the day 19 Holstein placenta (FIG. 3). All these are, therefore, "early" PAGs and candidates for early pregnancy antigens. Note that PAG2 (SEQ ID NO:2), previously detected in late pregnancy (Xie et al., 1994), is also present at day 19 and 25, but that boPAG1 (SEQ ID NO:1) is not expressed on any of these days as determined by a combination of procedures, including immuno screening. This point is important as the antisera used by others for detecting pregnancy (Sasser et al., 1986; Zoli et al., 1992a; Mialon et al., 1993) appear to recognize boPAG1. Note also that the antiserum against boPAG1 does recognize one of the "early" PAGs, namely PAG4. It seems likely, therefore, that these previous investigators were able to detect early pregnancy in cows because their antiserum fortuitously cross-reacted, albeit weakly, with boPAG4.

A considerable degree of amino acid sequence identity exists among the 12 boPAGs listed in FIG. 1. The most related are boPAG1 and boPAG3, sharing a 86% amino acid identity. The least related are boPAG4 and boPAG10 with only 49% identity. Interestingly boPAG1 and boPAG4, which as noted above cross react with the anti-boPAG1 antiserum, exhibit only 76% identity at the amino acid level. Presumably a common epitope exists on the two molecules.

The hypervariable regions noted in FIG. 1 coincide with surface loop regions on the modeled structures (Xie et al., 1997b) and are potential distinguishing epitopes. In this regard, boPAG1 and boPAG4 share one common loop (LSKDEREGS:209–217; PAG1 numbering) (FIG. 1), which may explain their immunological cross reactivity. Other loops could be mimicked as synthetic peptides and used to immunize rabbits or mice in order to raise specific antibodies against particular PAGs.

These data show that boPAG1, the antigen used as the basis for previous pregnancy tests, is a "late" PAG and not ideal as an early pregnancy antigen. The data also show that the "early" PAGs are relatively numerous and differ considerably from each other and from boPAG1 in sequence. These differences are most marked in surface loop regions, which are likely to be the most immunoreactive features of the molecule.

B. Example 2

Structural Relationships Among boPAGS

Materials and Methods: The amino acid sequences of various PAGs and pepsin were assembled into multiple sequence alignments with the Pile Up Program of the Wisconsin GCG Package, Version 9.0 (Madison, Wis.). A distance matrix was then created (Program Distances) and a phylogenetic tree constructed by a neighbor-joining procedure (Nei, 1987).

Results: The data in FIG. 5 is a phylogenetic tree relating all of the bovine PAGs (FIG. 1) and ovine PAGs (FIG. 2) that have so far been cloned as cDNA. The methods used for cloning these PAG cDNAs is described by Xie et al., 1997b. Also included in FIG. 5 are rabbit pepsinogen F and porcine pepsinogen A, the aspartic proteinases structurally most similar to PAGs. Note that the bovine and ovine PAGs fall largely into two structurally related groups. One contains boPAG2, -10, -11, and -12, along with ovPAG2 and ovPAG5. The other is comprised of boPAG1, 3, 4, 5, 6, 7, and 9. As pointed out below and by Xie et al., (1997b) the boPAGs in this second group are expressed only in binucleate cells, the invasive component of the trophoblast and the cell type considered to release PAGs into the maternal bloodstream. Note that among the PAGs in the second group are the "early" PAGs, boPAG4, 5, 6, 7, and 9.

C. Example 3

Certain Early PAGs are Expressed in Trophoblast Binucleate Cells and in the Syncytium Formed Between Trophectoderm and Uterine Epithelium Materials and Methods: Riboprobes (cRNA) were prepared by using the Riboprobe Preparation System (Promega, Wis., USA). Briefly, two regions of the boPAG cDNA, representing poorly conserved sequences, were used as the probe in situ hybridization (and ribonuclease protection assay: see next section). The first fragment (536bp) of boPAG2, 4, 8, 9 or 11 cDNA, that was in the region of exons 6, 7, 8 and 9, was amplified by using PCR™ with a pair of primers (Forward 5'CCTCTTTTGCCTTCTACTTGA3' (SEQ ID NO: 18, and Reverse 5'GCGCTCGAGTTACACT-GCCCGTGCCAGGC3' (SEQ ID NO:19). However, another region (407bp) was chosen for boPAG1, 5, 6 and 7 cDNA, corresponding to exons 3, 4 and 5. Again it was amplified by a PCR™ procedure with two well conserved primers (Forward B: 5'TGGGTAACATCACCATTGGAA3' (SEQ ID NO:20, Reverse B: 5'TTTCTGAGCCT-GTTTTTGCC5' (SEQ ID NO:21). The PCR™ products were subcloned into TA cloning vectors (Invitrogen, CA, USA). The orientation and sequence of the inserts were determined by sequencing.

The subcloned cDNA fragments were then transcribed in vitro into cRNA in the presence of [$^{35}$S]-CTP. Non-incorporated [$^{35}$S]CTP was removed by centrifugation of the labeling mix through a Sephadex G-50 column. The control probes, sense cRNA of boPAG, were prepared in essentially the way described above. The probes were used within 3 days. Day 25 or Day 100 tissue was sectioned (14μm) at −18° C. with an IEC cryostat (International Equipment Co., Needham Heights, Mass.) and mounted onto prechilled microscope slides.

The sections were then fixed and processed as described by Xu et al., (1995). Hybridization was performed by application of about 200 μl of probe solutions (4×10$^6$ cpm) to cover each section and incubated at 55° C. for 12 to 18 h. After hybridization, the slides were dipped in 2×SSC to remove the excess hybridization buffer, treated with RNase A(50 μl/ml in PBS) for 30 min at 37° C. to eliminate probes that were not hybridized. The sections were then washed at 55° C. in 2×SSC for 15 min, in 50% formamide in 2×SSC for 30 min and twice in 0.1×SSC for 15 min. Slides were again dehydrated, air dried, coated with Kodak NTB-2 emulsion (Eastman Kodak, Rochester, N.Y.) and exposed for 1 to 4 weeks at 4° C. Finally, the slides were developed, counterstained with hematoxylin and eosin and examined microscopically.

In situ hybridization was performed with [$^{35}$S]-antisense probes on sections through placentomes (areas of fused cotyledonary, i.e., fetal and caruncular, i.e., maternal, villi). Resulting autoradiographs were stained with hemotoxylin and cosin and photographed. No specific hybridization signals were shown with sense probe. BoPAG9 mRNA was concentrated in the more scattered binucleate cells, while that for boPAG11 was found in all the cells of the chorionic epithelium (trophectoderm).

In situ hybridization was performed with [$^{35}$S]-antisense probes on day 25 endometrium-placental sections using darkfield micrographs at 20× and 40×. The silver-grains appear to be white dots under darkground illumination. The cell layer at the edge of the section gave an intense boPAG6 signal. Abundant silver stains were localized to the cells at the margin of the section. In contrast, boPAG2 mRNA gave only a weak signal within the syncytial region. Few silver grains were visible at the edge of the section.

Results:

1. Localization of boPAG mRNAs at Day 100 of Pregnancy

The outer layer of the placenta consists of two populations of trophoblast cells, mono- and binucleate trophoblast cells. To localize the site of each PAG expression specifically to mono- or binucleate trophoblast cells, in situ hybridization were performed to detect individual PAG mRNA. Previous published data have shown that while boPAG1 is expressed in trophoblast binucleate cells (Xie et al., 1994), boPAG2 is expressed throughout the trophectodern, including the more abundant mononucleated cells that comprise 80% or more of the epithelium (Xie et al., 1994).

Here, in situ hybridization has been on sections of placentomes employed to determine in what cell type the remaining characterized boPAGs are expressed. BoPAG9 is expressed largely in the scattered binucleate cells, which are heavily covered with silver grains. By contrast, mRNA for boPAG11 is found throughout the epithelium covering the cotyledonary villi.

There is a correspondence between the PAGs that are expressed in binucleate cells and their positions in the phylogenetic tree (FIG. 5), and that four of the PAGs known to be expressed early, namely boPAG4, 5, 6, 7 and 9, are produced by the invasive binucleate cell, and therefore, likely to enter the maternal bloodstream.

2. Localization at Day 25 of Pregnancy

Bovine placenta on day 25 of pregnancy is not fully developed and the cotyledons are not firmly interdigitated with the caruncular endometrium. Therefore, the thickened placental membrane was processed with the attached endometrium. By the time it had been through the in situ hybridization procedures, most of the membrane was lost. Only the layer that fused with the endometrium survived the harsh procedure and remained on the surface of endometrium.

It was very difficult to identify individual cells since most cells (the remaining placental tissue) were fused with the underlining endometrial cells. Nevertheless, these fused multicellular syncytium contained plentiful amount of boPAG6 mRNA. As observed previously, only binucleate trophoblast can fuse with endometrium. Therefore, the placental cells in the syncytium are most likely to be binucleate trophoblast cells in origin. Similarly the sections hybridized to boPAG4, 5, 7 and 9 probes, also had very strong signals at the interface between the remaining placental membrane and the endometrial epithelium. Hence, they are most likely to be expressed by the binucleate trophoblast cells.

In contrast, very little mRNA for boPAG2, 8, 10, 11 was localized to the syncytical layer. A plausible explanation is that either those boPAG are not expressed or are expressed at low levels in the fused binucleate trophoblast cells at day 25 placenta. They are less likely, therefore, to be found in maternal blood than boPAG4, 5, 6, 7 and 9.

D. Example 4

Relative Expression of mRNA for Different boPAG Transcripts Varies Over Gestation in Cows Materials and Methods: Riboprobes (cRNA) were prepared by the Riboprobe Preparation System (Promega, Wis., USA). Briefly, two regions of the boPAG cDNA, that represent poorly conserved regions of PAGs in general were used as probes for RPA as well as for in situ hybridization. The first fragment (536 bp) of boPAG2, 4, 8, 9 and 11 cDNA, in the region of exons 6, 7, 8 and 9, was amplified by using PCR™ with the same pair of primers (SEQ ID NO:18 and SEQ ID NO:19) described in Example 3 for in situ hybridization. Similarly a region (407 bp) of boPAG1, 5, 6, or 7 cDNA corresponding to exons 3, 4 and 5, was amplified as described in Example 3 with primers (SEQ ID NO:20 and SEQ ID NO:21).

After subcloning, the cDNA fragments were transcribed in vitro into cRNA in the presence of [$^{32}$P-α]CTP. Total cellular RNA was extracted from placental tissue at different stages of pregnancy by using guanidium isothiocyanate and purified over a cesium chloride gradient (Sambrook et al., 1989; Ausubel et al., 1987). Twenty µg of RNA was used for each RPA reaction according to the manufacturer's recommendations (Ambion Inc., Austin, Tex.). In short, the sample RNA was co-precipitated with $^{32}$P-labeled probes $2 \times 10^6$ cpm/sample) and the pellet suspended in 10 µl of hybridization buffer and incubated at 68° C. for 10 min. Unhybridized cRNA was digested with a mixture of RNase A/TI for 45 min at 37° C. The cRNA probe and mRNA hybrids were precipitated and separated in 6% long range sequence gels and visualized by autoradiography.

A fragment of boPAG cDNA was amplified by PCR™ and the products subsequently subcloned into TA cloning vectors. Those fragments were then in vitro transcribed into riboprobes in the presence [$^{32}$P]CTP. RNA was extracted from bovine conceptus and placenta on days 25, 45, 88, 250 and term of pregnancy. The total tissue RNA (20 µm) was then hybridized with cRNA probes of boPAG1, boPAG2, boPAG4, boPAG5, boPAG6, boPAG7, boPAG8, boPAG9, boPAG10 and boPAG11. The protected DNA fragments were separated and visualized by autoradiography.

Results: The length of gestation in cattle is about 285 days. Initial immunoscreening of cDNA libraries previously identified three boPAG (boPAG1, 2 and 3). More recently two additional cDNA (boPAG13 and boPAG14) were cloned from mRNa of term placenta by using hybridization screening (SEQ ID NO: 13) and (SEQ ID NO:14) in a day 260 placental cDNA library (Xie et al., 1991; Xie et al., 1995). On day 25 pregnancy, ten distant PAG were identified (Example 1, FIG. 1, FIG. 2 and FIG. 5). Only boPAG2 was isolated from both stages of pregnancy. These cloning data imply that expression of individual boPAG is temporally controlled. To confirm the temporal expression of boPAG, ribonuclease protection assays were carried out to delineate the stages at which individual boPAGgenes were expressed in the cattle placenta. This procedure was repeated at least twice for each boPAG riboprobe and for each RNA sample. The major band represents the protected boPAG mRNA. In addition, there were multiple small bands in each lane. Those smaller bands almost certainly protected sequences highly related to, but distinct from, that of the riboprobe.

In summary boPAG2, was found in RNA at days 19, 25 and 260 and was therefore expressed through gestation. Similarly boPAG8, 10 and 11 were expressed at all stages of pregnancy examined. BoPAG1, which was originally characterized from day 260 placenta and is the basis of the pregnancy test of Sasser et al., (1986), Zoli et al., (1992a) and Mialon et al., (1992; 1993) was expressed at a very low level on day 25 of pregnancy. By day 45, its expression was elevated markedly. Other boPAG in the same group had varied expression on day 25. However, none of them showed enhanced expression by day 45 of pregnancy.

E. Example 5

Artiodactyla Species Related to *Bos taurus* Also Have Multiple PAG Genes

Materials and Methods: Southern genomic blots of bovine DNA were performed with probes corresponding to a segment of the boPAG1 encompassing part of intron 6, exon 7, intron 7, exon 8 the proximal end and the proximal end of intron 8 (Xie et al., 1995). The restriction enzyme EcoRI was chosen that did not cleave the probe. Conditions of hybridization were such that the PAG1 probe did not bind the PAG2 gene, nor would there be hybridization to genes for other known aspartic proteinases.

Results: Multiple PAG genes were detectable in all species of the Bovidae family examined. Signals were especially strong in the species closely related to *Bos taurus* within the subfamilies Bovinae (e.g., *Bos frontalis gaurus*, gaur; *Bos grunniens*, yak: *Syncerus caffer*, Cape buffalo) and Caprinae (e.g., *Ovis aires*, domestic sheep; *ovis dalli*, Dall sheep; *Capra falconeri*, Markhor goat, *Nemorhaedus goral*, goral; *Budorcas taxicolor*, takin). Gazelle and antelope species in other related subfamilies, including the impala, gnu, duiker, and nyala, also gave strong signals.

In general hybridization, although detectable, was weaker to DNA of members of the Cervidae family, including the whitetail deer and mule deer, than to DNA from Bovidae. Unexpectedly, moose (*Alces alces*) gave a relatively strong signal. The giraffe (family Giraffidae) provided the weakest signal of the true pecoran ruminants, possibly reflecting its early divergence (Kageyama et al., 1990). Hybridization to DNA from the Nile hippopotamus was barely detectable with the boPAG1 probe employed. since the hippo (family Hippotamidae; suborder Suiformes) is related to the domestic pig (*Sus Scrofa*), a species with multiple PAGs (Szafranska et al., 1995), this result indicates the considerable divergence of the genes within the Artiodactyla order over the 55 to 65 million years of its existence.

These data together show that there are multiple PAG genes with considerable structural similarity to boPAG1 in all ruminant ungulate species examined. Thus, a pregnancy test developed for domestic cattle (*Bos taurus*) on the basis of "early" PAG secretion by the placenta might also have utility in these other species as well.

F. Example 6

The Placenta of the Domestic Cat (*Feli catus*) Expresses a PAG Related to boPAGs Materials and Methods: Day 30 cat placentas from a single litter were obtained from the University of Missouri Veterinary Taching Hospital. Tissue was cut into small chunks and frozen in liquid $N_2$. Total RNA was extracted from frozen tissues and polyA$^+$ mRNA purified by using the micro-FastTrack™ kit from Invitrogen, CA. This RNA was reverse transcribed and the resulting cDNA collected ( ). PCR™ was conducted with the following primers, which represent highly conserved regions of the majority of boPAG genes (5'TGGGTAACATCACCATTGGAAC3' (215–236), (SEQ ID NO:22, ovPAGe5r 5'CAAACATCACCACACT-GCCCTCC3' (667–645), (SEQ ID NO:23).

PCR™ reactions were run for 35 cycles. Each cycle was 94° C. for1 min.; 42° C. for 1 min.; 72° C. for 1 min. The TA cloning kit (Invitrogen, CA) was employed to clone the PCR™ products. Plasmid DNA was isolated by using a Mini Prep Kit (Promega, Madison, Wis.). The isolated plasmid DNA were digested with the EcoRI restriction enzyme to check the sizes of inserts. In order to localize the site of cat PAG expression more precisely, in situ hybridization (as described in Example 3, section C) was used to detect cat PAG mRNA in frozen day 30 cat placental tissue. Cat PAG transcripts were detected with an antisense $^{35}$S-labeled riboprobe.

Results: The open reading frame of the cat PAG cDNA was 1164bp and encoded a polypeptide of 388 amino acids with a predicted Mr of 43,035 Cat PAG (SEQ ID NO:15). The amino acid sequence (SEQ ID NO:38) of cat PAG showed between 50 and 60% identity to all known bovine PAGs and 59.4% identity to porcine pepsinogen A.

Together these data suggest that the PAG occur outside the Ungulata order and are also found in non-hoofed species such as the domestic cat. By inference they are likely to be also found in related cat species (Felidae) as well as in the dogs (Canidae). A pregnancy test based on "early" PAG antigens could have utility in these species, particularly in the domestic dog (*Canis familiarus*).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VIII. References

The following references, to the extent that they provide exemplary procedural or other details supplementary to those set forth herein, are specifically incorporated herein by reference:

Abbondanzo et al., *Breast Cancer Res. Treat.*, 16:182(151), 1990.
Allred et al., *Breast Cancer Res. Treat.*, 16:182(149), 1990.
Amoroso, In: *Marshall's Physiology of Reproduction*, Vol. 2, Parkes, A. S. (Ed.), Little Brown and Co., Boston, pp 127–311, 952, 1952.
Atkinson et al., *J. Biol. Chem.*, 268(35):26679–26685, 1993.
Ausubel et al., *Curr. Protocols Molec. Biol.*, 2:16.9.1–16.9.10, 1997.
Baichwal and Sugden, In: *Gene Transfer*, Kucherlapati R. (Ed.), Plenum Press, New York, pp 117–148, 1986.
Barany and Merrifield, In: *The Peptides*, Gross and Meienhofer (Eds.), Academic Press, New York, pp 1–284, 1979.
Beal et al., *J. Anim. Sci.*, 70:924–929, 1992.
Birch and Loh, *Biochem. Biophys. Res. Commun.*, 177(3):920–926, 1991.
Brown et al., *Breast Cancer Res. Treat.*, 16: 192(#191), 1990.
Butler et al., *Biol. Reprod.*, 26:925–933, 1982.
Cameron and Malmo, *Austr. Vet. J.*, 70:109–111, 1993.
Campbell et al., *J. Mol. Biol.*, 180:1–19, 1984.
Capaldi et al., *Biochem. Biophys. Res. Comm.*, 76:425, 1977.
Chen and Okayama, *Mol. Cell Biol.*, 7:2745–2752, 1987.
Coffin, In: *Virology*, Fields B N and Knipe D M (Ed.), Raven Press, New York, pp 1437–1500, 1990.
Coupar et al., *Gene*, 68:1–10, 1988.
Crowther, "ELISA: Theory and Practice," In: *Methods in Molecule Biology*, Vol. 42, Humana Press; New Jersey, 1995.
Davies, *Ann. Rev. Bioiphys. Chem.*, 19:189–215, 1990.
Engvall and Perlmann, *Immunochem.*, 8:871–873, 1971.
Engvall, *Lancet*, 2(8000):1410, 1976.

Engvall, *Med Biol.*, 55(4): 193–200, 1977.
Engvall, *Methods Enzymol*, 70(A):419–39, 1980.
Fechheimer et al., *Proc. Nat'l Acad. Sci. USA*, 84:8463–8467, 1987.
Fraley et al., *Proc. Natl. Acad. Sci. USA*, 76:3348–3352, 1979.
Friedmann et al., *Science*, 244:1275–1281, 1989.
Fryxell, *Trends Genet*, 12(9):364–369, 1996.
Gefter et al., *Somatic Cell Genet.*, 3:231–236, 1977.
Ghosh and Bachhawat, In: Liver Diseases, Targeted Diagnosis and Therapy Using Specific Receptors and Ligands, Wu and Wu (Ed.), Marcel Dekker, New York, pp 87–104, 1991.
Goding, In: *Monoclonal Antibodies: Principles and Practice*, 2d ed., Academic Press, Orlando, Fla., pp 60–61, 71–74, 1986.
Gopal, *Mol. Cell Biol.*, 5:1188–1190, 1985.
Graham and Van Der Eb, *Virology*, 52:456–467, 1973.
Gripenberg et al., *Scand J. Immunol.*, 7(2):151–7, 1978.
Guillomot, *J Reprod. Fertil.*, 49(Suppl):39–51, 1995.
Guruprasad et al., *Protein Engin.*, 9:949–856, 1996.
Haig, *Rev. Biol.*, 68:495–532, 1993.
Harland and Weintraub, *J. Cell Biol.*, 101:1094–1099, 1985.
Harlow and Lane, In: *Antibodies, a Laboratory Manual*, Cold Spring Harbor Laboratory, pp 139–281, 1988.
Hatzidakis et al., *J. Reprod. Fertil.*, 98:235–240, 1993.
Hermonat and Muzycska, *Proc. Nat. Acad. Sci. USA*, 81:6466–6470, 1984.
Holdsworth et al., *J. Endocrin.*, 95:7–12, 1982.
Horwich et al., *J. Virol.*, 64:642–650, 1990.
Hughes, *Mol. Biol. Evol.*, 11 (6):899–910, 1994.
Humblot et al., *Theriogenol.*, 30:257–268, 1988.
Innis et al., In: *PCR Protocols*, Academic Press, Inc., San Diego, Calif., 1990.
Johnson et al., "Peptide turn mimetics," In: *Biotechnology and Pharmacy*, Pezzuto et al. (Eds.), Chapman and Hall, New York, 1993.
Kageyama et al., *J. Biol. Chem.*, 265(28), 17031–17038, 1990.
King et al., *J. Reprod. Fertil.*, 59:95–100, 1980.
Kiracofe et al., *J. Anim. Sci.*, 71:2199–2205, 1993.
Kohler and Milstein, *Eur. J. Immunol.*, 6:511–519, 1976.
Kohler and Milstein, *Nature*, 256:495–497, 1975.
Li et al., *J. Virol.*, 67(7):4070–4077, 1993.
Markusfeld et al., *Br. Vet. J.*, 146: 504–508, 1990.
Merrifield, *Science*, 232:341–347, 1986.
Mialon et al., *Reprod. Nutr. Dev.*, 33:269–282, 1993.
Mialon et al., *Reprod. Nutr. Dev.*, 34:65–72, 1994.
Mialon, *Aviat. Space Environ Med.*, 63(4):287–291, 1992.
Miyamoto et al., In: *Mammalian Phylogeny*, Szalcy, F. S., Novacek, M. J. and McKenna, C. (Eds.), Springer, New York, pp 268–281, 1993.
Moir et al., *Gene*, 19:127–138, 1982.
Nakamura et al., In: *Handbook of Experimental Immunology* (4$^{th}$ Ed.), Weir, E., Herzenberg, L. A., Blackwell, C., Herzenberg, L. (Eds.), Vol. 1, Chapter 27, Blackwell Scientific Publ., Oxford, 1987.
Nei et al., In: *Molecular Evolutionary Genetics*, Columbia Univ. Press, New York, pp 293–298, 1987.
Nicolas and Rubenstein, In: *Vectors: A Survey of Molecular Cloning Vectors and Their Uses,"* Rodriguez and Denhardt (Eds.), Butterworth, Stoneham, pp 494–513, 1988.
Nicolau and Sene, *Biochim. Biophys. Acta*, 721:185–190, 1982.
Ohta et al., *Biochm. Biophys. Res. Commun.*, 185(3): 1128–1132, 1992.
Ohta, *Immunol. Lett*, 44(1):35–40, 1995.

Oltenacu et al., *J. Dairy Sci.*, 73:2826–2831, 1990.
Patel et al., *Theriogenol.*, 44:827–833, 1995.
Potter et al., *Proc. Nat'l Acad. Sci. USA*, 81:7161–7165, 1984.
Pungercar et al., *Nucl. Acids Res.*, 18:4602, 1990.
*Remington's Pharmaceutical Sciences*, 15th ed., pp 1035–1038 and 1570–1580.
Ridgeway, In: *Vectors: A Survey of Molecular Cloning Vectors and Their Uses*, Rodriguez R. L. and Denhardt D. T. (Ed.), Butterworth, Stoneham, pp 467–492, 1988.
Rippe et al., *Mol. Cell Biol.*, 10:689–695, 1990.
Roberts et al., *Biol. Reprod.*, 54:294–302, 1996.
Roberts et al., *Prog. Nucl. Acid Res. Mol. Biol.*, 56:287–326, 1996.
Sambrook et al., In: *Cold Spring Harbor Laboratory Press*, 2nd Ed., 1989.
Samgadharan et al., *Princess Takamatsu Symp.*, 15:301–8, 1984.
Sasser et al., *J. Reprod Fertil.*, 37(Suppl):109–113, 1989.
Sasser et al., *Biol. Reprod.*, 35:936–942, 1986.
Smith and Johnson et al., *Gene*, 67 31–40, 1988.
Stewart and Young, In: *Solid Phase Peptide Synthesis*, 2nd. ed., Pierce Chemical Co., 1984.
Streenan and Diskin, In: *Embryonic Mortality in Farm Animals*, Sreenan and Diskin (Eds.), Martinus Nijhoff Publishers, 1–11 , 1986.
Szafranska et al., *Biol. Reprod.*, 53:21–28, 1995.
Takahasi, *Adv. Exp. Med. Biol.*, 362:581–587, 1995.
Tam et al., *J. Am. Chem. Soc.*, 105:6442, 1983.
Temin, In: *Gene Transfer*, Kucherlapati (Ed.), Plenum Press, New York, pp 149–188, 1986.
Tur-Kaspa et al., *Mol. Cell Biol.*, 6:716–718, 1986.
U.S. Pat. No. 3,817,837.
U.S. Pat. No. 3,850,752.
U.S. Pat. No. 3,939,350.
U.S. Pat. No. 3,996,345.
U.S. Pat. No. 4,196,265.
U.S. Pat. No. 4,275,149.
U.S. Pat. No. 4,277,437.
U.S. Pat. No. 4,366,241.
U.S. Pat. No. 4,367,1 10.
U.S. Pat. No. 4,452,901.
U.S. Pat. No. 4,668,621.
U.S. Pat. No. 4,683,195.
U.S. Pat. No. 4,683,202.
U.S. Pat. No. 4,800,159.
Warnick et al., *Theriogenol.*, 44:811–825, 1995.
Wedemayer, *Science*, 276(5319):1665–1669, 1997.
Wooding et al., *Placenta*, 13:101–113, 1992.
Wooding, *J. Reprod. Fertil.*, 62:15–19, 1981.
Wu and Wu, *Biochemistry*, 27:887–892, 1988.
Wu and Wu, *J. Biol. Chem.*, 262:4429–4432, 1987.
Xie et al., *Biol. Reprod.*, 51:1145–1153, 1994.
Xie et al., *Biol. Reprod.*, 54: 122–129, 1996.
Xie et al., *Biol. Reprod.*, 57:1384–1393, 1997a.
Xie et al., *Gene*, 159:193–197, 1995.
Xie et al., *Proc. Nat'l Acad. Sci. USA*, 88: 10247–10251, 1991.
Xie et al., *Proc. Nat'l Acad. Sci. USA*, 94:12809–12816, 1997b.
Xu et al., *Endocrinol.*, 136:981–989, 1995.
Yang et al., *Proc. Natl. Acad. Sci USA*, 87:9568–9572, 1990.
Zoli et al., *Biol. Reprod.*, 46:623–629, 1992b.
Zoli et al., *Biol. Reprod.*, 45:1–10, 1991.
Zoli et al., *Biol. Reprod.*, 46:83–92, 1992a.

What is claimed is:

1. A method for detecting pregnancy in a bovine animal comprising:
   (a) obtaining a sample from said animal; and
   (b) contacting said sample with an antibody that binds immunologically to at least one pregnancy associated antigen (PAG), wherein said PAG is present in early pregnancy and undetectable at about two months postpartum, and wherein said PAG is selected from the group consisting of PAG4 (SEQ ID NO:27), PAG6 (SEQ ID NO:29), PAG7 (SEQ ID NO:30), PAG16 (SEQ ID NO:46); PAG17 (SEQ ID NO:29), PAG7 (SEQ ID NO:30), PAG16 (SEQ ID NO:46); PAG17 (SEQ ID NO:48); PAG20 (SEQ ID NO:54) and PAG21 (SEQ ID NO:56); and
   (c) detecting said PAG bound to said antibody;
   whereby the presence of said PAG in said sample indicates that said animal is pregnant.

2. The method of claim 1, wherein said sample is saliva, serum, blood, milk or urine.

3. The method of claim 2, wherein said sample is saliva.

4. The method of claim 2, wherein said sample is serum.

5. The method of claim 2, wherein said sample is blood.

6. The method of claim 2, wherein said sample is milk.

7. The method of claim 2, wheren said sample is urine.

8. The method of claim 1, wherein said detection comprises detection with polyclonal antisera.

9. The method of claim 1, wherein said detection comprises detection with a monoclonal antibody preparation.

10. The method of claim 1, wherein said detection comprises ELISA.

11. The method of claim 1, wherein said detection comprises RIA.

12. The method of claim 1, wherein said detection comprises Western blot.

13. The method of claim 1, further comprising detecting a second PAG in said sample.

14. The method of claim 13, rther comprising detecting a third PAG in said sample.

15. The method of claim 10, wherein said ELISA is a sandwich ELISA comprising binding of a PAG to a first antibody preparation fixed to a substrate and a second antibody preparation labeled with an enzyme.

16. The method of claim 15, wherein said enzyme is alkaline phosphatase or horseradish peroxidase.

17. The method of claim 15, wherein said first antibody preparation is monoclonal.

18. The method of claim 1, wherein said PAG is PAG4 (SEQ ID NO:27).

19. The method of claim 1, wherein said PAG is PAG6 (SEQ ID NO:29).

20. The method of claim 1, wherein said PAG is PAG7 (SEQ ID NO:30).

21. The method of claim 1, wherein said PAG is PAG16 (SEQ ID NO:46).

22. The method of claim 1, wherein said PAG is PAG17 (SEQ ID NO:48).

23. The method of claim 1, wherein said PAG is PAG20 (SEQ ID NO:54).

24. The method of claim 1, wherein said PAG is PAG21 (SEQ ID NO:56).

* * * * *

UNITED STATES PATENT AND TRADEMARK OFFICE
CERTIFICATE OF CORRECTION

PATENT NO.    : 6,869,770 B1
DATED         : March 22, 2005
INVENTOR(S)   : Roberts et al.

It is certified that error appears in the above-identified patent and that said Letters Patent is hereby corrected as shown below:

Column 125,
Line 12, delete "PAG17 (SEQ ID NO:29)" and replace with
-- PAG17 (SEQ ID NO:48) -- therefor.

Column 126,
Line 7, delete "rther" and replace with -- further -- therefor.

Signed and Sealed this

Twenty-first Day of June, 2005

JON W. DUDAS
*Director of the United States Patent and Trademark Office*

SEQUENCE LISTING

<160> NUMBER OF SEQ ID NOS: 56

<210> SEQ ID NO 1
<211> LENGTH: 1295
<212> TYPE: DNA
<213> ORGANISM: bovidae

<400> SEQUENCE: 1

```
cttggatcca ggaaataaac atgaagtggc ttgtgctcct cgggctggtg gccttctcag      60
agtgcatagt caaataccct ctaaggagac tgaagaccat gagaaatgtc gtcagtggaa     120
aaaacatgct gaacaatttt ctgaaggagc atgcttacag tctgtcccag atttcttttc     180
gtggctcaaa tctaactact cacccgctga gaaacatcaa ggatttggtc tacatgggta     240
acatcaccat ggaacacccc cctcaggaat tccaggttgt ctttgacaca gcctcatctg     300
acttgtgggt gccctccgac ttttgcacta gtccagcctg ttctacacac gttaggttca     360
gacatcttca gtcttccact ttccggctta ccaataagac cttcaggatc acctatggat     420
ctgggagaat gaaggagtt gttgttcatg acacagttcg gattgggaac cttgtaagta     480
ctgaccagcc atttggtcta agcattgagg aatacgggtt tgagggcaga atttatgatg     540
gtgtcttggg cttgaactac cccaacatat ccttctctgg agccatcccc atctttgaca     600
agctgaagaa tcaacgtgcc atttctgagc ctgttttgc cttctacttg agcaaagatg     660
agcgggaggg cagtgtggtg atgtttggtg ggtggacca ccgctattat gagggagagc     720
tcaactgggt accctgatc caagcaggcg actggagtgt acacatggac cgcatctcca     780
ttgaaagaaa gattattgct tgttctgatg gctgcaaggc ccttgtggac accgggacat     840
cagatatcgt aggtccaaga agactggtca ataacatcca taggctcatc ggtgccatac     900
cacggggttc cgagcactac gttccatgtt ctgaggtcaa tacccctgcc ctctattgtct     960
tcaccatcaa cggcatcaac tacccagtgc caggtcgagc ctacatcctc aaggatgata    1020
gaggccgctg ctataccacc tttcaagaga accgagtgag ttcatctaca gagacctggt    1080
acctgggtga cgtcttcctg agactgtatt tctcggtctt tgatcgagga aatgacagaa    1140
ttggcctggc acgggcagtg taaatgctta gagtggttca ggaatcagta aggccactcc    1200
taacacacac tcactcacac tttggcactc ctgcccagaa tgctggtgaa ctgtatttgg    1260
tggtcttcac actctattct tagtaaagaa taaag                                1295
```

<210> SEQ ID NO 2
<211> LENGTH: 1258
<212> TYPE: DNA
<213> ORGANISM: bovidae

<400> SEQUENCE: 2

```
gaaagaagca tgaagtggct tgtgctcctc gggctggtgg ccctctcaga gtgcatagtc      60
attttgcctc taagaaaat gaagaccttg cgagaaaccc tgagggaaaa aaacttgctg     120
aacaatttcc tggaggaaca agcttacaga ctgtccaaga tgactccaa ataactatt      180
cacccgctga ggaactatct ggatactgcc tacgtgggta acatcaccat ggaacaccc     240
cctcaggagt tccgggtcgt ctttgacaca ggctcagcta acttgtgggt gccctgcatc    300
acctgtacca gtccagcctg ttatacacac aaaaccttca atcctcaaaa ttcttcaagc    360
ttccgggaag taggctcgcc tatcaccatc ttctatggat ctgggataat tcagggattt    420
cttggctctg acaccgttcg gatcgggaac cttgttagcc ctgaacagtc gtttggccta    480
```

-continued

```
agcctggagg aatacgggtt tgattctcta ccctttgatg gtatcctggg cttggctttt      540
cccgccatgg gcatcgaaga taccatcccc atctttgaca acttgtggtc acacggtgcc      600
ttttctgagc ctgtcttcgc cttctacttg aacacaaaca agccagaggg cagtgtggtg      660
atgtttggtg gggtggacca ccgctactac aagggagagc tcaactggat accagtgtcc      720
caaactagcc attggcagat aagcatgaac aacatcagca tgaatgggac tgtgactgct      780
tgttcttgtg gatgtgaggc ccttttggac accgggacat caatgatcta cggcccaaca      840
aaactggtca ccaacatcca caagctcatg aacgccaggc ttgagaattc tgagtatgtg      900
gtttcatgtg atgctgtcaa gaccctgcct cctgtcatct tcaacatcaa tggcatcgac      960
tatccactgc gccctcaagc ctacatcatc aagattcaaa acagctgccg cagcgtcttt     1020
caaggaggca cagaaaatag ctctctaaac acctggatcc ttggtgatat cttcctgagg     1080
cagtacttct cggtttttga tcgtaaaaat agaaggattg gcctggctcc ggcagtgtaa     1140
atgcttggac tatcagcaag catttgacta aatcagtcag gctgctccta acacacactc     1200
gctcacacta ggcactcctg ccagcgatgc tggtgaattg tgtttggtgc tgcaaacc      1258
```

<210> SEQ ID NO 3
<211> LENGTH: 1266
<212> TYPE: DNA
<213> ORGANISM: bovidae

<400> SEQUENCE: 3

```
ggcttgtgct cctcgggctg gtggccttct cagagtgcat agtcaaaata cctctaagga       60
gagtgaagac catgagaaat accgtcagtg gaaaaaacat actgaacaat atcctgaagg      120
agcatgttta cagactgtcc cagatttctt ttcgtggctc aaatctaact actcacccgc      180
tgagaaacat caaggatttg atatacgtgg gtaacatcac cattggaaca ccccctcagg      240
aattccaggt tgtcttt gac acaggctcat ctgacttttg ggtgccctct gactttt gca      300 ctagtcgagc ctgttctaca cacgttaggt tcagacatct tcagtcttcc accttccggc      360
tcaccaataa gaccttcagg atcacctatg gatctgggag aatgaaagga gttgttgctc      420
atgacacagt tcggattggg gaccttgtaa gtactgacca accgtttggt ctaagtgtgg      480
aggaatatgg gtttgagggc agagcttatt atgatggtgt cttgggcttg aactacccca      540
acatatcctt ctctggagcc atccccatct tgacaacct gaagaatcaa ggtgccattt      600
ctgagcctgt ttttgccatt ctactgagca aagacgagca ggagggcagt gtggtgatgt      660
ttggtggggt ggaccaccgc tactatgagg gagagctcaa ctgggtacca ttgattgaag      720
cgggtgactg gattatacac atggaccgca tctccatgaa aagaaagatt attgcttgtt      780
ctggcagctg cgaggccatt gttgacactg gacatcagc aatagaaggc ccaagaaaac      840
tggtaaataa gatacacaag ctcatcggcg ccaggccacg gcattccaag tactacattt      900
catgttctgc ggtcaatacc ctgccttcta ttatcttcac catcaacggc atcaactacc      960
catgtccagg tcgagcctac gtgctcaagg attctagagg ccgctgctat tccatgtttc     1020
aagagaacaa agtgagttca tctacagaga cctggatcct gggcgatgtc tttctgaggg     1080
tgtatttctc agtctttgat cgaggaaatg acaggattgg cctggcacga gcagtgtaaa     1140
tgcttggagt ggttcaggaa tcagtaaggc cgctcctaac acacactcac tcacactagg     1200
cactcctgcc aggatggtg gtgaactgta tttggtggtc tgtacaccct attctctcgt      1260
gccgtt                                                              1266
```

<210> SEQ ID NO 4
<211> LENGTH: 1359
<212> TYPE: DNA
<213> ORGANISM: bovidae

<400> SEQUENCE: 4

| | | | | | |
|---|---|---|---|---|---|
| acaaaaaccc | tcagtggaaa | aaacatgctg | aacaatttcg | tgaaggagca | tgcttacaga | 60 |
| ctgtcccaga | tttcttttcg | tggctcaaat | ctaactattc | acccgctgag | aaacatcagg | 120 |
| gatttttct | atgtgggtaa | catcaccatt | gggacacccc | ctcaggaatt | ccaggttatc | 180 |
| tttgacacag | gctcatctga | gttgtgggtg | ccctccatct | tttgcaacag | ctcaacctgt | 240 |
| tctaaacacg | ataggttcag | acatcttgag | tcttctacct | tccggcttag | caggaggacc | 300 |
| ttcagcatca | cctatggatc | tgggagaatt | gaagcacttg | ttgttcatga | cacagttcgg | 360 |
| attggggacc | ttgtaagtac | tgatcagcag | ttcggtctat | gcctagaaga | atctgggttt | 420 |
| gagggcatga | gatttgatgg | cgtcttgggc | ttgagctata | ccaacatatc | ccctctgga | 480 |
| gccatcccca | tcttttacaa | gctgaagaat | gaaggtgcca | tttctgaacc | tgttttgcc | 540 |
| ttctacttga | gcaaagatga | gcgggagggc | agtgtggtga | tgtttggtgg | ggcggaccac | 600 |
| cgctactaca | agggagagct | caactggata | ccattgatga | aagcaggcga | ctggagtgta | 660 |
| cacatggacc | gcatctccat | gaaaagaaag | gttattgctt | gctctggcgg | ctgcaaggcc | 720 |
| cttgtggaca | cggggtcatc | agatatcgta | ggcccaagta | cactggtcaa | taacatctgg | 780 |
| aagctcatcg | gtgccacgcc | acagggttct | gagcactacg | tttcatgttc | tgcggtcaat | 840 |
| agcctaccct | ctattatctt | caccatcaaa | agcaacaact | accgagtgcc | aggtcaagcc | 900 |
| tacatcctca | aggattctag | aggccgctgc | tttactgcct | ttaaagggca | tcaacagagt | 960 |
| tcatctacag | agatgtggat | cctgggtgac | gtctttctga | ggctgtattt | ctcagtcttt | 1020 |
| gatcgaagaa | aggacagaat | tggcctggcc | accaaggtgt | gaatgcttgg | agtggttcag | 1080 |
| gaatcagtaa | ggccactcct | aacacacact | cactcacact | ttgggcactc | ctgcccaagg | 1140 |
| aatgctggtg | aactgtaatt | tggtggtctg | tacaccctat | tctctgggaa | gaaggcaatg | 1200 |
| gcacccccact | ccagtactct | tgcctggaaa | atcacatgga | cagaagcctg | gtgggctcca | 1260 |
| gtccatgggg | tttctaagag | tcgggcaata | actgagcacc | ttcacttata | ctttcacttt | 1320 |
| acaccctatt | ctcaataaaa | gataaatggt | ttcactctt | | | 1359 |

<210> SEQ ID NO 5
<211> LENGTH: 1317
<212> TYPE: DNA
<213> ORGANISM: bovidae

<400> SEQUENCE: 5

| | | | | | |
|---|---|---|---|---|---|
| ccctgagtac | ttggagccag | gaaagaagta | tgaagtggct | tgtgctcctt | gggctgctga | 60 |
| cctcctcaga | gtgcatagtc | atcctacctc | taacaaaagt | gaagaccatg | agaaaaaccc | 120 |
| tcagtgaaaa | aaacatgctg | aacaatttcc | tgaaggaaca | ggcttacaga | ctgtcccaga | 180 |
| tttcttctcg | tggctcaaat | ataactattc | atccctgag | aacatcatg | gatatggtct | 240 |
| atgtgggtaa | aatcaccatt | ggaacacccc | ctcaggaatt | ccaggttgtc | tttgacacag | 300 |
| gctcatctga | gttgtgggtg | ccctccgtct | tttgccccag | ttcagcctgt | tctactcaca | 360 |
| ttaggttcag | acatcttgag | tcttccactt | ccggcctaac | ccaaaagacc | ttcagcatca | 420 |
| cctatggatc | tgggagcacg | aagggatttc | ttgcttatga | caccgttcgg | attggggacc | 480 |
| ttctaagtac | tgatcaggaa | ttcggactaa | gcatggaaga | acacggggttt | gaggatctac | 540 |

-continued

```
cttttgatgg cgtcttgggc ttgaactacc ctgacatgtc cttcataaca accatcccca    600
tctttgacaa cctcaagaat caaggtgcct tttctgagcc tgttttttgcc ttctacttgg    660
gcaaggtgaa gggcagtgtg gtgatgtttg gtggggtgga ccacacctac tacaagggag    720
agctcaactg ggtgccattg atccaggcag gtgagtggag tctacacatg gaccgcatct    780
ccatgaaaag aaaggttatt gcttgttctg gtggctgcga ggccttctat gacactggaa    840
catcactgat ccttggccca agaagactgg tcaataacat ccagaagctc atcggtgcca    900
cgccacaggg ttccgagcac tacatttcat gttttgctgt catatccctg ccctctatta    960
tcttcaccat caacggcatc aacatcccag tgccagctcg agcctacatc cacaaggatt   1020
ctagaggcca ctgctatccc acctttaaag agaacacagt gagtacatcc acagagacct   1080
ggatcctggg tgacgtcttc ctgaggctct atttctcagt ttttgatcga ggaaatgaca   1140
ggattggcct ggcacaggtg taaatgcttg gagtggttca ggaatcagta aggccgctcc   1200
taacacacac tcactcacac tttgagactc ctgcccagga tgctggtgaa ctgtatttgg   1260
tggtctgcac accctattct caggaaagaa taaagggttt cactcttaat ggtgctg      1317
```

<210> SEQ ID NO 6
<211> LENGTH: 1322
<212> TYPE: DNA
<213> ORGANISM: bovidae

<400> SEQUENCE: 6

```
ggagccagaa aatcacatga agtggcttgt gctcctcggg ctggtggcct tctcagagtg     60
catagtcaaa atacctctaa ggagagtgaa gacaatgaga aatgctatca gtggaaaaaa    120
cacgctgaac aaatatcctga aggagcatgc ttacagactg ccccagattt cttttcgtgg    180
ctcaaatcta actcacccac tgagaaacat cagggatttg ttctacgtgg gtaacatcac    240
cattgggaca ccccctcagg aattccaggt tatctttgac acaggctcat ctgacttgtg    300
ggtggcctcc atcttttgca acagctcatc ctgtgctgca cacgttaggt tcagacatca    360
tcagtcttcc accttccggc ctaccaataa gaccttcagg atcacctatg gatctgggag    420
aatgaaagga gttgttgttc atgacacagt tcggattggg gaccttgtaa gtactgacca    480
gccattcggt ctatgcctga aagactctgg gtttaagggc atacctttg atggcatctt    540
gggcttgagc taccccaaca aaaccttctc tggagccttc cccatctttg acaagctgaa    600
gaatgaaggt gccatttctg agcctgtttt tgccttctac ttgagcaaag acaagcagga    660
gggcagtgtg gtgatgtttg gtggggtgga ccaccgctac tacaaggggg agctcaactg    720
ggtaccattg atccaagtgg gtgactggtt tgtacacatg gaccgcacta ccatgaaaag    780
aaaggttatt gcttgttctg atggctgcaa ggcccttgtg gacaccggga catcagatat    840
cgtaggccca agtacactgg tcaataacat ctggaagctc atccgtgcca ggccactggg    900
tcctcagtac ttcgtttcat gttctgcggt caatacactg ccctctatta tcttcaccat    960
caacggcatc aactaccgac tgccagctcg agcctacatc cacaaggatt ctagaggccg   1020
ctgctatacc gcctttaaag agcaccgatt cagttcacct atagagacct ggctcctggg   1080
tgacgtcttc ctgaggcggt atttctcagt ctttgatcga ggaaatgaca ggattggcct   1140
ggcacgggca gtgtaaatgc ttagagtggc tcaggaatca gtaaggccgt tcctaacaca   1200
ccttaactca cactttgggc actcttgcct aggatgctgg tgaactgtat ttggtgctcg   1260
tacacccatt ctagtaaaga ataaagggtt tcacttaacg ggtgctgaaa aaaaaaaaaa   1320
```

| aa | 1322 |

<210> SEQ ID NO 7
<211> LENGTH: 1211
<212> TYPE: DNA
<213> ORGANISM: bovidae

<400> SEQUENCE: 7

| acaccaaaac ttccctgagt acttggaacc aggaagaag catgaagtgg cttgtgctcc | 60 |
| tcgggctggt ggccttctca gagtgcatag tcaaaatacc tctaaggaga gtgaagacca | 120 |
| tgagaaaaac tctcagtgga aaaaacatgc tgaacaattt cttgaaggag atccttaca | 180 |
| gactgtccca catttctttt cgtggctcaa atctaactat tcacccgctg agaaacatca | 240 |
| gagatatctt ctatgtcgga acatcacca ttggaacacc ccctcaggaa ttccaggtta | 300 |
| tctttgacac aggctcatct gacttgtggg tgccctcgat cgattgcaac agtacatcct | 360 |
| gtgctacaca tgttaggttc agacatcttc agtcttccac cttccggcct accaataaga | 420 |
| ccttcaggat catctatgga tctgggagaa tgaacggagt tattgcttat gacacagttc | 480 |
| ggattgggga ccttgtaagt accgaccagc catttggtct aagcgtggag gaatatgggt | 540 |
| ttgcgcacaa aagatttgat ggcatcttgg cttgaacta ctggaaccta tcctggtcta | 600 |
| aggccatgcc catctttgac aagctgaaga atgaaggtgc catttctgag cctgtttttg | 660 |
| ccttctactt gagcaacatc accatgaaca gagaggttat tgcttgttct gaaggctgtg | 720 |
| cggcccttgt ggacactggg tcatcaaata tccaaggccc aggaagactg attgataaca | 780 |
| tacagaggat catcggcgcc acgccacggg gttccaagta ctacgtttca tgttctgcgg | 840 |
| tcaatatcct gccctctatt atcttcacca tcaacgcgt caactaccca gtgccacctc | 900 |
| gagcttacat cctcaaggat tctagaggcc actgctatac cacctttaaa gagaaaagag | 960 |
| tgaggagatc tacagagagc tgggtcctgg gtgaagtctt cctgaggctg tatttctcag | 1020 |
| tctttgatcg aggaaatgac aggattggcc tggcacggcg agtgtaaatg cttggtctgg | 1080 |
| ctcaagaatc attaaggcca ctcctaacac acactcactc acactttggg cactgctgcc | 1140 |
| aggatgctgg tgaactgtat ttgtgttctg tacacctat tctcagtaaa gaataaaggg | 1200 |
| tttcagctct t | 1211 |

<210> SEQ ID NO 8
<211> LENGTH: 1340
<212> TYPE: DNA
<213> ORGANISM: bovidae

<400> SEQUENCE: 8

| caggaattcg cggccgcgtc gacggaaaga agcatgaagt ggcttgtgct tctcgggctg | 60 |
| gtggccctct cagagtgcat agtcaaaatc cctctaacga agatgaagac catgcaagaa | 120 |
| gccatcaggg aaaaacaatt gctggaagat ttcttggatg aacaacctca cagcctgtcc | 180 |
| cagcattctg atcctgacaa gaaattctct tctcaccaac tgaagaattt ccagaatgct | 240 |
| gtctactttg gtacgatcac cattggaaca cctcctcaag agttccaggt caactttgac | 300 |
| accggctcat ctgacttgtg ggtgccctct gtcgactgcc aaagtccctc ctgctctaaa | 360 |
| cataagagat tcgaccctca gaagtccacc accttccagc ctttgaacca gaaaattgaa | 420 |
| ctcgtctacg gctctgggac catgaaaggg gttcttggct ctgacaccat tcagatcggg | 480 |
| aaccttgtca tcgtgaacca gattttggc ttgagccaga tcagtccag tggcgtcctg | 540 |
| gaacaagtac cttatgatgg catcctgggc ttggcctacc ccagcctcgc catccagggg | 600 |

-continued

```
accaccccag tcttcgacaa cctgaagaat cgagaagtca tttctgagcc agtctttgcc        660
ttctacttga gctcccggcc agaaaacatc agcacggtga tgtttggcgg ggtggaccac        720
acctaccaca agggaaaact ccagtggatc ccagtgaccc aagcccgctt ctggcaggta        780
gccatgagca gcatgaccat gaacgggaat gtggtcggtt gttcccaagg atgtcaggcc        840
gttgtggata ctgggacctc gttgctggtt gggccaactc acctggtcac tgacatcctg        900
aagctcatca accctaatcc tatcctgaat gacgagcaaa tgctttcatg tgatgccatc        960
aatagcctgc ctacgctcct cctcaccatc aacggcatcg tctaccctgt gcccctgac        1020 tactacatcc agaggttttc tgaaaggatc tgctttatca gctttcaagg gggcacagag       1080
atcttgaaaa atttgggaac ctcggagacc tggatcctgg gtgatgtctt cctgaggctg       1140 tattttcag tttatgaccg aggaaataac aggattggcc tggctcctgc agcataaatt       1200
cgggctgcta caggaatcaa tcagggccag acaaacacac actcactcac atgcagggcc       1260
atcccaccca gggatgctgg tgaactatgc ctgatgctct gcaaagccgt attctcagta       1320
aagaataaaa gattcatttc                                                  1340

<210> SEQ ID NO 9
<211> LENGTH: 1311
<212> TYPE: DNA
<213> ORGANISM: bovidae

<400> SEQUENCE: 9
accccaaact tccctgagta cctggagcca gtaaagaagc atgaagtgga ttgtgctcct        60
cgggctggtg gccttctcag agtgcatagt caaaataccct ctaaggcaag tgaagaccat      120
gagaaaaacc ctcagtggaa aaacatgct gaagaatttc ttgaaggagc atccttacag       180
actgtcccag atttcttttc gtggctcaaa tctaactatt cacccgctga ggaacatcat       240
gaatttggtc tacgtgggta acatcaccat tggaacaccc cctcaggaat tccaggttgt       300
ctttgacaca ggctcatctg acttgtgggt gccctccttt tgtaccatgc cagcatgctc       360
tgcaccggtt tggttcagac aacttcagtc ttccacccttc cagcctacca ataagacctt      420
caccatcacc tatggatctg ggagcatgaa gggatttctt gcttatgaca cagttcggat       480 tggggaccctt gtaagtactg atcagccgtt cggtctaagc gtggtggaat atgggttgga      540
gggcagaaat tatgatggtg tcttgggctt gaactacccc aacatatcct tctctggagc       600
catccccatc tttgacaacc tgaagaatca aggtgccatt tctgagcctg ttttttgcctt      660 ctacttgagc aaaaacaagc aggagggcag tgtggtgatg tttggtgggg tggaccacca       720
gtactacaag ggagagctca actggatacc actgattgaa gcaggcgaat ggagagtaca       780
catggaccgc atctccatga aaagaacggt tattgcttgt tctgatggct gtgaggccct       840
tgtgcacact gggacatcac atatcgaagg cccaggaaga ctggtgaata acatacacag       900
gctcatccgc accaggccat tgattccaa gcactacgtt tcatgttttg ccaccaaata       960
cctgccctct attactttca tcatcaacgg catcaagtac ccaatgacag ctcgagccta      1020
catctttaag gattctagag gccgctgcta ttccgctttt aaagagaaca cagtgagaac       1080
atctagagag acctggatcc tcggtgatgc cttcctgagg cggtatttct cagtctttga      1140
tcgaggaaat gacaggattg gcctggcacg ggcagtgtaa atgcttagag tggttcagga       1200
atcagtaagg ccgttcctaa cacacactaa ctcacacttt gggcactctt gcctaggatg       1260
ctggtgaacc tgtctttggt ggtcttgtac caccctattc tcagtaaaga a                1311
```

<210> SEQ ID NO 10
<211> LENGTH: 1328
<212> TYPE: DNA
<213> ORGANISM: bovidae

<400> SEQUENCE: 10

```
tccgactctg tcttgagcac ttcagtggag dacaaaagca tgaagtggct tggacttctc      60
gggctggtag ctctctcaga gtgcatggtc ataatccctc ttaggcaaat gaagaccatg     120
cgagaaaccc taagggaaag acatttgctg acaaatttct ctgaggaaca cccttacaac     180
ctgtcccaga aagctgctaa tgatcaaaac ataatttatc atcatccctt gaggagctat     240
aaggattttt cctacatcgg caacatcaac attggaacac cccctcagga gttccaggtc     300
ctctttgaca ccggctcatc tagcttgtgg gtgccctcca tatactgcca gagttccagc     360
tgctataaac acaatagctt cgtcccttgt aactcctcca ccttcaaggc cacgaacaag     420
atcttcaata ccaactacac cgctacatcg ataaagggat atcttgtcta tgacactgtt     480
cggatcggga accttgttag tgtggcccag ccatttggcc taagcctgaa ggagtttggg     540
tttgacgatg taccatttga tggcatcctg gactaggtt acccacgccg cactatcaca     600
ggggccaacc cgatcttcga caacctgtgg aaacaaggag tcatttctga gcctgtcttt     660
gccttctact tgagcagtca gaaagagaac ggcagcgtgg tgatgtttgg aggggtgaac     720
cgtgcctact ataagggaga actcaactgg gtaccagtgt cccaagtggg cagctggcat     780
ataaacatag acagcatctc catgaatggg acagtggttg cttgtaaacg tggctgccag     840
gcctcttgga tacggggacg cctttctgcg tggcccaaga ggatcgtcag caaaatccag     900
aaactcatcc atgccaggcc catcgatcgt gagcacgtgg tttcctgcca agccatcggg     960
acactgcctc ctgctgtctt cactatcaat gggatagact atccagtacc cgcccaagct    1020
tacatccaaa gtttgtcggg ctactgcttc agcaactttc ttgtgcgccc acagcgtgtg    1080
aacgagtcgg agacctggat cctgggtgac gtcttcctga ggctgtattt ctcagttttc    1140
gatcgaggaa acaacaggat tggcctggct cccgcagtgt aaatgctggg ctacttcagg    1200
aatcaatcag gcccactcca aacacatact catgtgaggg cacctgggt ggggccaggg    1260
atgctggtga actctgtttg ttgcgctgca aagccctact ctctatagag aataaaggat    1320
ttcatctc                                                            1328
```

<210> SEQ ID NO 11
<211> LENGTH: 1285
<212> TYPE: DNA
<213> ORGANISM: bovidae

<400> SEQUENCE: 11

```
gagatgaagt ggcttgtgtt ccttgggctg gtggccttct cagagtgcat agtcataatg      60
cttctaacta aaacgaagac aatgcgagaa atctggaggg aaaaaaaatt gctgaacagt     120
ttcctggagg aacaagccaa tagaatgtcc gatgattctg ctagtgaccc caaattatct     180
actcaccccc tgaggaacgc tctggatatg gcctatgtgg gtaacatcac cattggaaca     240
cccccctaagg agttccgggt tgtctttgac acgggctcat ctgacttgtg ggtgccctcc     300
atcaagtgca tcagtcctgc ctgtcataca catattacct tcgaccatca caaatcttcc     360
accttccggc ttacgcgcag gcccttccac atcctctacg atctgggat gatgaacgga     420
gttcttgcct atgacactgt tcggatcggg aaacttgtca gcactgacca gccgtttggc     480
ctaagcctgc agcaattcgg gtttgataat gcaccctttg atggtgtcct gggcttgtcc     540
```

-continued

```
taccccagcc tcgctgtccc aggaaccatc cccatctttg acaagctgaa gcaacaaggt      600
gccatttctg aacctatctt tgccttctac ttgagcaccc gcaaggagaa tggcagtgtg      660
ttgatgttag gtggggtgga ccactcctac acaagggaa agctcaactg gataccagtg       720
tcccaaacca aaagctggct aataactgtg gaccgcatct ccatgaatgg gagagtgatt      780
ggctgtgaac acggctgcga ggctcttgtg gataccggga catcactgat ccatggccca      840
gcaagaccag tcaccaacat ccaaaagttc atccacgcta tgccctacgg ttccgagtac      900
atggttttgt gtcctgtcat cagtatcctg cctcctgtca tcttcaccat caatggcatc      960
gattactcag tgcctcgtga agcctacatc caaaagattt ctaatagctt atgccttagc     1020 accttttcatg gggacgacac agaccaatgg atcctgggtg acgtcttcct gaggctgtat    1080
ttctcagttt atgaccgagg aaataacagg attggcctgg ctcctgctgt gtaaatgctt    1140
ggacttgttc aggaatcatt caggccagtc ctaacacaca cttgctcaca ctttagactc     1200
ctgcccagga tgctggtaaa ctgtgtttgg tgctctgaaa gtcatattct cactgaaaaa    1260
taaaaggttt cactcttaac atctt                                          1285
```

<210> SEQ ID NO 12
<211> LENGTH: 1130
<212> TYPE: DNA
<213> ORGANISM: bovidae

<400> SEQUENCE: 12

```
atgaagtggc ttgtgctcct cgggctggtg gccctctcag agtgcatagt cattttgcct       60
ctaaggaaaa tgaagacctt gcgagaaacc ctgagggaaa aaacttgct gaacaatttc      120 ctggaagaac gagcttacag actgtccaag aaagactcca aataactat tcaccccctt      180 aaaactatct ggatatggcc tacgtgggta atatcaccat ggaacacccc cctcaggaat     240
tccgggtcgt ctttgacaca ggctcagctg acttgtgggt gccttccatc agctgtgtca      300
gtccagcctg ttatacacac aaaaccttca atcttcacaa ttcttccagc ttcgggcaaa    360
cacaccagcc tattgcatc tcctatggac ctgggataat tcagggattt cttggctctg     420
acaccgttcg gatcgggaac cttgttagcc ttaaacagtc gtttggccta agccaggagg     480
aatatgggtt tgatggtgca ccctttgatg gcgtcctggg cttggcctac ccctccatca     540
gcatcaaagg tatcatcccc atctttgaca acttgtggtc gcaaggtgcc ttttctgaac     600
ctgtctttgc cttctacttg aacacatgcc agccggaagg cagtgtggtg atgtttggtg     660
gagtggacca ccgctactac aagggagagc tcaactggat accagtgtcc caaactcgct     720
actggcagat aagcatgaac cgcatcagca tgaacgggaa tgttactgct tgttctcgtg     780
gatgtcaggc ccttttggac accgggacat caatgatcca tggcccaaca agactgatca    840
ccaacatcca aagctcatg aacgccaggc accagggttc ggagtatgtg gtttcatgtg     900
atgccgtcaa gaccctgcct cctgtcatct tcaacatcaa tggcatcgac tatccactgc     960
cccctcaagc ctacatcacc aaggctcaaa acttctgcct tagcatcttt catgggggca    1020
cagaaactag ctctccagag acctggatcc tgggtggcgt cttcctgaga cagtacttct    1080 cagttttttga tcgaagaaat gacagtattg gcctggcaca ggtgtaaatg              1130
```

<210> SEQ ID NO 13
<211> LENGTH: 1173
<212> TYPE: DNA
<213> ORGANISM: bovidae

-continued

<400> SEQUENCE: 13

```
cccaagctta tgaagtggct tgtgctcctc gggctggtgg ccctctcaga gtgcatagtc      60
attttgcctc taaagaaaat gaagaccttg cgagaaaccc tgagggaaaa aaacttgctg     120
aacaatttcc tggaggaaca agcttacaga ctgtccaaga atgactccaa aataactatt     180
caccccctga ggaactatct ggatactgcc tacgtgggta acatcaccat tggaacaccc     240
cctcaggagt tccggtcgt ctttgacaca ggctcagcta acttgtgggt gccctgcatc      300
acctgtacca gtccagcctg ttatacacac aaaaccttca atcctcaaaa ttcttcaagc     360
ttccgggaag taggctcgcc tatcaccatc ttctatggat ctgggataat tcagggattt     420
cttggctctg acaccgttcg gatcgggaac cttgttagcc ttaaacagtc gtttggccta     480
agccaggagg aatatgggtt tgatggtgca ccctttgatg cgtcctggg cttggcctac      540
ccctccatca gcatcaaagg tatcatcccc atctttgaca acttgtggtc gcacggtgcc     600
ttttctgagc ctgtcttcgc cttctacttg aacacaaaca agccagaggg cagtgtggtg     660
atgtttggtg gggtggacca ccgctactac aagggagagc tcaactggat accagtgtcc     720
caaactagcc attggcagat aagcatgaac aacatcagca tgaatgggac tgtgacggct     780
tgttcttgtg gatgtgaggc ccttttggac accgggacat caatgatcta cggcccaaca     840
aaactggtca ccaacatcca aagctcatg aacgccaggc ttgagaattc tgagtatgtg      900
gtttcatgtg atgctgtcaa gaccctgcct cctgtcatct tcaacatcaa tggcatcgac     960
tatccactgc gccctcaagc ctacatcatc aagattcaaa acaactgccg cagcgtcttt    1020
caaggaggca cagaaaatag ctctctaaac acctggatcc ttggtgatat cttcctgagg    1080
cagtacttct cggttttga tcgtaaaaat agaaggattt gctggcacag gtgggtaccg     1140
actacaagga cgacgatgac aagtaagctt ccg                                 1173
```

<210> SEQ ID NO 14
<211> LENGTH: 1176
<212> TYPE: DNA
<213> ORGANISM: bovidae

<400> SEQUENCE: 14

```
cccaagctta tgaagtggct tgtgctcctt gcgctggtgg ccttctcaga gtgcataatc      60
aaaatacctc taaggagagt gaagaccatg agcaataccg ccagtggaaa aaacatgctg     120
aacaatttcc tgaagaagca tccttacaga ttgtcccaga tttctttcg tggctcaaat      180
ctcactactc acccactgat gaacatctgg gatttgctct acctgggtaa catcaccatt     240
ggaacacccc ctcaggaatt ccaggttctc tttgacacag gctcatctga cttgtgggtc     300
ccctctctct tgtgcaacag ctcaacctgt gctaaacacg ttatgttcag acatcgtctg     360
tcttccacct accggcctac caataagacc ttcatgatct tctatgcagt tgggaaaatt     420
gaaggagttg ttgttcgtga cacagttcgg attgggggacc ttgtaagtgc ggaccagacg    480
tttggtctaa gcattgcaga aactgggttt gagaacacaa ctcttgatgg catcttgggc     540
ttgagctacc ccaacacatc ctgctttgga accatcccca tctttgacaa gctgaagaat     600
gaaggtgcca tttctgagcc tgtactacat agtgtgagac gcaaagatga gcaggagggc     660
agtgtagtga tgtttggtgg tgtggaccac agttactaca agggagagct caactgggta     720
ccattgatca aagcaggcga ctggagtgta cgtgtggaca gcatcaccat gaaaagagag     780
gttattgctt gttctgacgg ctgcagggcc ctggtgaca ccggttcatc acatatccaa      840
ggcccaggaa gactgatcga taacgtacag aagctgatag gcaccatgcc acagggatcc     900
```

```
atgcactatg ttccatgttc tgcggtcaat accctgccct ctattatctt caccatcaac      960
agcatcagct acacagtgcc agctcaagcc tacatcctca agggttctag gggccgctgc     1020
tattccacct ttcaagggca cactatgagt tcatctacag agacctggat cctgggtgat     1080
gtcttcctga gtcagtattt ctcggtcttt gatcgaggaa atgacaggat tggcctggca     1140
caggtgggta ccgactacaa ggacgacgat gaaagt                               1176
```

<210> SEQ ID NO 15
<211> LENGTH: 1360
<212> TYPE: DNA
<213> ORGANISM: Felis domestica

<400> SEQUENCE: 15

```
aggaaagaag catgaagtgg ctttgggtcc ttgggctggt ggccctctca gagtgcttag       60
tcacaatccc tctgacgagg gtcaagtcca tgcgagaaaa cctcaggag aaagacaggc      120 tgaaggattt cctggagaac catccttaca acctggccta caagtttgtt gactctgtaa      180
atctggacct ggggatatat tttgaaccga tgaggaacta cctggatctg cctacgttg       240 gcaccatcag cattggaacg cccccccagg agttcaaggt catctttgac accggctcat      300
ctgacttgtg ggtgccctcc atctactgct ctagccctgc ctgcgctaat cacaacgtct      360
tcaaccctct gcggtcctcc accttccgga tctcgggccg gccatccac ctccagtacg       420 gctccgggac gatgtcagga tttctggcct acgacaccgt tcggttcggg ggcctcgttg      480
acgtggccca ggcgtttggc ctgagcctga gggagcccgg caagttcatg aatacgcag      540 ttttcgacgg catcctgggc ctggcctacc ccagcctcag cctcagaggg accgtccctg      600
tcttcgacaa cctgtggaag cagggtctca tttctcagga gctctttgcc ttctacttga      660
gcaaaaagga cgaagaaggc agtgtggtga tgttcggcgg tgtggaccac tcctactaca      720
gcggagacct caactgggtg ccggtgtcca acggctgta ctggcagtta tccatggaca       780
gcatctccat gaacggggaa gtcattgctt gtgacggtgg ctgccaggcc atcattgata      840
caggaacctc gctgctgatt ggcccatctc acgttgtctt caacatccag atgatcatcg      900
gcgccaacca gtcctacagc ggcgagtacg tagttgactg cgatgccgcc aacaccctgc      960
ccgacatcgt cttcaccatc aacggcatcg actacccgt gccagccagt gcctacatcc     1020
aggagggtcc tcagggcacc tgctacagcg gctttgacga gagcggagac agcttgttgg     1080
tctcagactc ctggatcctg ggcgatgtct tcctgaggtt gtatttcacc gtcttcgacc     1140
gagagaacaa caggattggc ctggccctgg cagtgtaaac actggggcca gctccaggaa     1200
gcaaccgtgc ccaccccaaa cccgcgcgcg cgtgtgcgca cacacacaca cacacaccc     1260 gcagtcaggg cattcctgcc caggggccgg cttgaactgt gtcttcggct ctgccaatcc     1320
cttctcccag tggagaataa aagacctcat cttccacggt                          1360
```

<210> SEQ ID NO 16
<211> LENGTH: 29
<212> TYPE: DNA
<213> ORGANISM: Artificial Sequence
<220> FEATURE:
<223> OTHER INFORMATION: Description of Artificial Sequence: PCR primer

<400> SEQUENCE: 16

```
cccaagctta tgaagtggct tgtgctcct                                         29
```

<210> SEQ ID NO 17

<211> LENGTH: 69
<212> TYPE: DNA
<213> ORGANISM: Artificial Sequence
<220> FEATURE:
<223> OTHER INFORMATION: Description of Artificial Sequence: PCR primer

<400> SEQUENCE: 17
gggaagctta cttgtcatcg tcgtccttgt agtcggtacc cacctgtgcc aggccaatcc    60
tgtcatttc                                                             69

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: PCR primer

<400> SEQUENCE: 18
cctcttttgc cttctacttg a                                               21

<210> SEQ ID NO 19
<211> LENGTH: 29
<212> TYPE: DNA
<213> ORGANISM: Artificial Sequence
<220> FEATURE:
<223> OTHER INFORMATION: Description of Artificial Sequence: PCR primer

<400> SEQUENCE: 19
gcgctcgagt tacactgccc gtgccaggc                                       29

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: PCR primer

<400> SEQUENCE: 20
tgggtaacat caccattgga a                                               21

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: PCR primer

<400> SEQUENCE: 21
tttctgagcc tgttttgcc                                                  20

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: PCR primer

<400> SEQUENCE: 22
tgggtaacat caccattgga ac                                              22

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: PCR primer

<400> SEQUENCE: 23
caaacatcac cacactgccc tcc                                                    23

<210> SEQ ID NO 24
<211> LENGTH: 380
<212> TYPE: PRT
<213> ORGANISM: bovidae

<400> SEQUENCE: 24

```
Met Lys Trp Leu Val Leu Leu Gly Leu Val Ala Phe Ser Glu Cys Ile
  1               5                  10                  15

Val Lys Ile Pro Leu Arg Arg Leu Lys Thr Met Arg Asn Val Val Ser
             20                  25                  30

Gly Lys Asn Met Leu Asn Asn Phe Leu Lys Glu His Ala Tyr Ser Leu
         35                  40                  45

Ser Gln Ile Ser Phe Arg Gly Ser Asn Leu Thr Thr His Pro Leu Arg
     50                  55                  60

Asn Ile Lys Asp Leu Val Tyr Met Gly Asn Ile Thr Ile Gly Thr Pro
 65                  70                  75                  80

Pro Gln Glu Phe Gln Val Val Phe Asp Thr Ala Ser Ser Asp Leu Trp
                 85                  90                  95

Val Pro Ser Asp Phe Cys Thr Ser Pro Ala Cys Ser Thr His Val Arg
            100                 105                 110

Phe Arg His Leu Gln Ser Ser Thr Phe Arg Leu Thr Asn Lys Thr Phe
        115                 120                 125

Arg Ile Thr Tyr Gly Ser Gly Arg Met Lys Gly Val Val His Asp
    130                 135                 140

Thr Val Arg Ile Gly Asn Leu Val Ser Thr Asp Gln Pro Phe Gly Leu
145                 150                 155                 160

Ser Ile Glu Glu Tyr Gly Phe Glu Gly Arg Ile Tyr Asp Gly Val Leu
                165                 170                 175

Gly Leu Asn Tyr Pro Asn Ile Ser Phe Ser Gly Ala Ile Pro Ile Phe
            180                 185                 190

Asp Lys Leu Lys Asn Gln Arg Ala Ile Ser Glu Pro Val Phe Ala Phe
        195                 200                 205

Tyr Leu Ser Lys Asp Glu Arg Glu Gly Ser Val Val Met Phe Gly Gly
    210                 215                 220

Val Asp His Arg Tyr Tyr Glu Gly Glu Leu Asn Trp Val Pro Leu Ile
225                 230                 235                 240

Gln Ala Gly Asp Trp Ser Val His Met Asp Arg Ile Ser Ile Glu Arg
                245                 250                 255

Lys Ile Ile Ala Cys Ser Asp Gly Cys Lys Ala Leu Val Asp Thr Gly
            260                 265                 270

Thr Ser Asp Ile Val Gly Pro Arg Arg Leu Val Asn Asn Ile His Arg
        275                 280                 285

Leu Ile Gly Ala Ile Pro Arg Gly Ser Glu His Tyr Val Pro Cys Ser
    290                 295                 300

Glu Val Asn Thr Leu Pro Ser Ile Val Phe Thr Ile Asn Gly Ile Asn
305                 310                 315                 320

Tyr Pro Val Pro Gly Arg Ala Tyr Ile Leu Lys Asp Asp Arg Gly Arg
                325                 330                 335

Cys Tyr Thr Thr Phe Gln Glu Asn Arg Val Ser Ser Ser Thr Glu Thr
            340                 345                 350
```

```
Trp Tyr Leu Gly Asp Val Phe Leu Arg Leu Tyr Phe Ser Val Phe Asp
        355                 360                 365

Arg Gly Asn Asp Arg Ile Gly Leu Ala Arg Ala Val
    370                 375                 380

<210> SEQ ID NO 25
<211> LENGTH: 376
<212> TYPE: PRT
<213> ORGANISM: bovidae

<400> SEQUENCE: 25

Met Lys Trp Leu Val Leu Leu Gly Leu Val Ala Leu Ser Glu Cys Ile
  1               5                  10                  15

Val Ile Leu Pro Leu Lys Lys Met Lys Thr Leu Arg Glu Thr Leu Arg
             20                  25                  30

Glu Lys Asn Leu Leu Asn Asn Phe Leu Glu Glu Gln Ala Tyr Arg Leu
         35                  40                  45

Ser Lys Asn Asp Ser Lys Ile Thr Ile His Pro Leu Arg Asn Tyr Leu
     50                  55                  60

Asp Thr Ala Tyr Val Gly Asn Ile Thr Ile Gly Thr Pro Pro Gln Glu
 65                  70                  75                  80

Phe Arg Val Val Phe Asp Thr Gly Ser Ala Asn Leu Trp Val Pro Cys
                 85                  90                  95

Ile Thr Cys Thr Ser Pro Ala Cys Tyr Thr His Lys Thr Phe Asn Pro
            100                 105                 110

Gln Asn Ser Ser Ser Phe Arg Glu Val Gly Ser Pro Ile Thr Ile Phe
        115                 120                 125

Tyr Gly Ser Gly Ile Ile Gln Gly Phe Leu Gly Ser Asp Thr Val Arg
    130                 135                 140

Ile Gly Asn Leu Val Ser Pro Glu Gln Ser Phe Gly Leu Ser Leu Glu
145                 150                 155                 160

Glu Tyr Gly Phe Asp Ser Leu Pro Phe Asp Gly Ile Leu Gly Leu Ala
                165                 170                 175

Phe Pro Ala Met Gly Ile Glu Asp Thr Ile Pro Ile Phe Asp Asn Leu
            180                 185                 190

Trp Ser His Gly Ala Phe Ser Glu Pro Val Phe Ala Phe Tyr Leu Asn
        195                 200                 205

Thr Asn Lys Pro Glu Gly Ser Val Val Met Phe Gly Gly Val Asp His
    210                 215                 220

Arg Tyr Tyr Lys Gly Glu Leu Asn Trp Ile Pro Val Ser Gln Thr Ser
225                 230                 235                 240

His Trp Gln Ile Ser Met Asn Asn Ile Ser Met Asn Gly Thr Val Thr
                245                 250                 255

Ala Cys Ser Cys Gly Cys Glu Ala Leu Leu Asp Thr Gly Thr Ser Met
            260                 265                 270

Ile Tyr Gly Pro Thr Lys Leu Val Thr Asn Ile His Lys Leu Met Asn
        275                 280                 285

Ala Arg Leu Glu Asn Ser Glu Tyr Val Val Ser Cys Asp Ala Val Lys
    290                 295                 300

Thr Leu Pro Pro Val Ile Phe Asn Ile Asn Gly Ile Asp Tyr Pro Leu
305                 310                 315                 320

Arg Pro Gln Ala Tyr Ile Ile Lys Ile Gln Asn Ser Cys Arg Ser Val
                325                 330                 335

Phe Gln Gly Gly Thr Glu Asn Ser Ser Leu Asn Thr Trp Ile Leu Gly
            340                 345                 350
```

-continued

```
Asp Ile Phe Leu Arg Gln Tyr Phe Ser Val Phe Asp Arg Lys Asn Arg
            355                 360                 365
Arg Ile Gly Leu Ala Pro Ala Val
        370                 375

<210> SEQ ID NO 26
<211> LENGTH: 381
<212> TYPE: PRT
<213> ORGANISM: bovidae

<400> SEQUENCE: 26

Met Asp Asp Leu Val Leu Leu Gly Leu Val Ala Phe Ser Glu Cys Ile
  1               5                  10                  15

Val Lys Ile Pro Leu Arg Arg Val Lys Thr Met Arg Asn Thr Val Ser
             20                  25                  30

Gly Lys Asn Ile Leu Asn Ile Leu Lys Glu His Val Tyr Arg Leu
         35                  40                  45

Ser Gln Ile Ser Phe Arg Gly Ser Asn Leu Thr Thr His Pro Leu Arg
     50                  55                  60

Asn Ile Lys Asp Leu Ile Tyr Val Gly Asn Ile Thr Ile Gly Thr Pro
 65                  70                  75                  80

Pro Gln Glu Phe Gln Val Val Phe Asp Thr Gly Ser Ser Asp Phe Trp
             85                  90                  95

Val Pro Ser Asp Phe Cys Thr Ser Arg Ala Cys Ser Thr His Val Arg
            100                 105                 110

Phe Arg His Leu Gln Ser Ser Thr Phe Arg Leu Thr Asn Lys Thr Phe
        115                 120                 125

Arg Ile Thr Tyr Gly Ser Gly Arg Met Lys Gly Val Val Ala His Asp
    130                 135                 140

Thr Val Arg Ile Gly Asp Leu Val Ser Thr Asp Gln Pro Phe Gly Leu
145                 150                 155                 160

Ser Val Glu Glu Tyr Gly Phe Glu Gly Arg Ala Tyr Tyr Asp Gly Val
                165                 170                 175

Leu Gly Leu Asn Tyr Pro Asn Ile Ser Phe Ser Gly Ala Ile Pro Ile
            180                 185                 190

Phe Asp Asn Leu Lys Asn Gln Gly Ala Ile Ser Glu Pro Val Phe Ala
        195                 200                 205

Ile Leu Leu Ser Lys Asp Glu Gln Glu Gly Ser Val Val Met Phe Gly
    210                 215                 220

Gly Val Asp His Arg Tyr Tyr Glu Gly Glu Leu Asn Trp Val Pro Leu
225                 230                 235                 240

Ile Glu Ala Gly Asp Trp Ile Ile His Met Asp Arg Ile Ser Met Lys
                245                 250                 255

Arg Lys Ile Ile Ala Cys Ser Gly Ser Cys Glu Ala Ile Val Asp Thr
            260                 265                 270

Gly Thr Ser Ala Ile Glu Gly Pro Arg Lys Leu Val Asn Lys Ile His
        275                 280                 285

Lys Leu Ile Gly Ala Arg Pro Arg His Ser Lys Tyr Tyr Ile Ser Cys
    290                 295                 300

Ser Ala Val Asn Thr Leu Pro Ser Ile Ile Phe Thr Ile Asn Gly Ile
305                 310                 315                 320

Asn Tyr Pro Cys Pro Gly Arg Ala Tyr Val Leu Lys Asp Ser Arg Gly
                325                 330                 335

Arg Cys Tyr Ser Met Phe Gln Glu Asn Lys Val Ser Ser Ser Thr Glu
```

```
                    340              345              350
Thr Trp Ile Leu Gly Asp Val Phe Leu Arg Val Tyr Phe Ser Val Phe
            355              360              365

Asp Arg Gly Asn Asp Arg Ile Gly Leu Ala Arg Ala Val
        370              375              380

<210> SEQ ID NO 27
<211> LENGTH: 380
<212> TYPE: PRT
<213> ORGANISM: bovidae

<400> SEQUENCE: 27

Met Lys Trp Leu Val Leu Leu Gly Leu Val Ala Phe Ser Glu Cys Ile
 1               5                   10                  15

Val Lys Ile Pro Leu Arg Arg Val Lys Thr Met Thr Lys Thr Leu Ser
            20                  25                  30

Gly Lys Asn Met Leu Asn Asn Phe Val Lys Glu His Ala Tyr Arg Leu
        35                  40                  45

Ser Gln Ile Ser Phe Arg Gly Ser Asn Leu Thr Ile His Pro Leu Arg
    50                  55                  60

Asn Ile Arg Asp Phe Phe Tyr Val Gly Asn Ile Thr Ile Gly Thr Pro
65                  70                  75                  80

Pro Gln Glu Phe Gln Val Ile Phe Asp Thr Gly Ser Ser Glu Leu Trp
                85                  90                  95

Val Pro Ser Ile Phe Cys Asn Ser Ser Thr Cys Ser Lys His Asp Arg
            100                 105                 110

Phe Arg His Leu Glu Ser Ser Thr Phe Arg Leu Ser Arg Arg Thr Phe
        115                 120                 125

Ser Ile Thr Tyr Gly Ser Gly Arg Ile Glu Ala Leu Val Val His Asp
    130                 135                 140

Thr Val Arg Ile Gly Asp Leu Val Ser Thr Asp Gln Gln Phe Gly Leu
145                 150                 155                 160

Cys Leu Glu Glu Ser Gly Phe Glu Gly Met Arg Phe Asp Gly Val Leu
                165                 170                 175

Gly Leu Ser Tyr Thr Asn Ile Ser Pro Ser Gly Ala Ile Pro Ile Phe
            180                 185                 190

Tyr Lys Leu Lys Asn Glu Gly Ala Ile Ser Glu Pro Val Phe Ala Phe
        195                 200                 205

Tyr Leu Ser Lys Asp Glu Arg Glu Gly Ser Val Val Met Phe Gly Gly
    210                 215                 220

Ala Asp His Arg Tyr Tyr Lys Gly Glu Leu Asn Trp Ile Pro Leu Met
225                 230                 235                 240

Lys Ala Gly Asp Trp Ser Val His Met Asp Arg Ile Ser Met Lys Arg
                245                 250                 255

Lys Val Ile Ala Cys Ser Gly Gly Cys Lys Ala Leu Val Asp Thr Gly
            260                 265                 270

Ser Ser Asp Ile Val Gly Pro Ser Thr Leu Val Asn Asn Ile Trp Lys
        275                 280                 285

Leu Ile Gly Ala Thr Pro Gln Gly Ser Glu His Tyr Val Ser Cys Ser
    290                 295                 300

Ala Val Asn Ser Leu Pro Ser Ile Ile Phe Thr Ile Lys Ser Asn Asn
305                 310                 315                 320

Tyr Arg Val Pro Gly Gln Ala Tyr Ile Leu Lys Asp Ser Arg Gly Arg
                325                 330                 335
```

```
Cys Phe Thr Ala Phe Lys Gly His Gln Gln Ser Ser Thr Glu Met
            340                 345                 350

Trp Ile Leu Gly Asp Val Phe Leu Arg Leu Tyr Phe Ser Val Phe Asp
            355                 360                 365

Arg Arg Lys Asp Arg Ile Gly Leu Ala Thr Lys Val
370                 375                 380

<210> SEQ ID NO 28
<211> LENGTH: 377
<212> TYPE: PRT
<213> ORGANISM: bovidae

<400> SEQUENCE: 28

Met Lys Trp Leu Val Leu Leu Gly Leu Leu Thr Ser Ser Glu Cys Ile
1               5                   10                  15

Val Ile Leu Pro Leu Thr Lys Val Lys Thr Met Arg Lys Thr Leu Ser
                20                  25                  30

Glu Lys Asn Met Leu Asn Phe Leu Lys Glu Gln Ala Tyr Arg Leu
            35                  40                  45

Ser Gln Ile Ser Ser Arg Gly Ser Asn Ile Thr Ile His Pro Leu Arg
    50                  55                  60

Asn Ile Met Asp Met Val Tyr Val Gly Lys Ile Thr Ile Gly Thr Pro
65              70                  75                  80

Pro Gln Glu Phe Gln Val Val Phe Asp Thr Gly Ser Ser Glu Leu Trp
                85                  90                  95

Val Pro Ser Val Phe Cys Pro Ser Ala Cys Ser Thr His Ile Arg
                100                 105                 110

Phe Arg His Leu Glu Ser Ser Thr Ser Gly Leu Thr Gln Lys Thr Phe
            115                 120                 125

Ser Ile Thr Tyr Gly Ser Gly Ser Thr Lys Gly Phe Leu Ala Tyr Asp
    130                 135                 140

Thr Val Arg Ile Gly Asp Leu Leu Ser Thr Asp Gln Glu Phe Gly Leu
145                 150                 155                 160

Ser Met Glu Glu His Gly Phe Glu Asp Leu Pro Phe Asp Gly Val Leu
                165                 170                 175

Gly Leu Asn Tyr Pro Asp Met Ser Phe Ile Thr Thr Ile Pro Ile Phe
            180                 185                 190

Asp Asn Leu Lys Asn Gln Gly Ala Phe Ser Glu Pro Val Phe Ala Phe
    195                 200                 205

Tyr Leu Gly Lys Val Lys Gly Ser Val Val Met Phe Gly Gly Val Asp
    210                 215                 220

His Thr Tyr Tyr Lys Gly Glu Leu Asn Trp Val Pro Leu Ile Gln Ala
225                 230                 235                 240

Gly Glu Trp Ser Leu His Met Asp Arg Ile Ser Met Lys Arg Lys Val
                245                 250                 255

Ile Ala Cys Ser Gly Gly Cys Glu Ala Phe Tyr Asp Thr Gly Thr Ser
            260                 265                 270

Leu Ile Leu Gly Pro Arg Arg Leu Val Asn Asn Ile Gln Lys Leu Ile
            275                 280                 285

Gly Ala Thr Pro Gln Gly Ser Glu His Tyr Ile Ser Cys Phe Ala Val
    290                 295                 300

Ile Ser Leu Pro Ser Ile Ile Phe Thr Ile Asn Gly Ile Asn Ile Pro
305                 310                 315                 320

Val Pro Ala Arg Ala Tyr Ile His Lys Asp Ser Arg Gly His Cys Tyr
                325                 330                 335
```

-continued

```
Pro Thr Phe Lys Glu Asn Thr Val Ser Thr Thr Glu Thr Trp Ile
            340                 345                 350

Leu Gly Asp Val Phe Leu Arg Leu Tyr Phe Ser Val Phe Asp Arg Gly
            355                 360                 365

Asn Asp Arg Ile Gly Leu Ala Gln Val
            370                 375

<210> SEQ ID NO 29
<211> LENGTH: 379
<212> TYPE: PRT
<213> ORGANISM: bovidae

<400> SEQUENCE: 29

Met Lys Trp Leu Val Leu Leu Gly Leu Val Ala Phe Ser Glu Cys Ile
  1               5                  10                  15

Val Lys Ile Pro Leu Arg Arg Val Lys Thr Met Arg Asn Ala Ile Ser
             20                  25                  30

Gly Lys Asn Thr Leu Asn Asn Ile Leu Lys Glu His Ala Tyr Arg Leu
         35                  40                  45

Pro Gln Ile Ser Phe Arg Gly Ser Asn Leu Thr His Pro Leu Arg Asn
     50                  55                  60

Ile Arg Asp Leu Phe Tyr Val Gly Asn Ile Thr Ile Gly Thr Pro Pro
 65                  70                  75                  80

Gln Glu Phe Gln Val Ile Phe Asp Thr Gly Ser Ser Asp Leu Trp Val
                 85                  90                  95

Ala Ser Ile Phe Cys Asn Ser Ser Cys Ala Ala His Val Arg Phe
                100                 105                 110

Arg His His Gln Ser Ser Thr Phe Arg Pro Thr Asn Lys Thr Phe Arg
                115                 120                 125

Ile Thr Tyr Gly Ser Gly Arg Met Lys Gly Val Val His Asp Thr
            130                 135                 140

Val Arg Ile Gly Asp Leu Val Ser Thr Asp Gln Pro Phe Gly Leu Cys
145                 150                 155                 160

Leu Lys Asp Ser Gly Phe Lys Gly Ile Pro Phe Asp Gly Ile Leu Gly
                165                 170                 175

Leu Ser Tyr Pro Asn Lys Thr Phe Ser Gly Ala Phe Pro Ile Phe Asp
                180                 185                 190

Lys Leu Lys Asn Glu Gly Ala Ile Ser Glu Pro Val Phe Ala Phe Tyr
                195                 200                 205

Leu Ser Lys Asp Lys Gln Glu Gly Ser Val Val Met Phe Gly Gly Val
            210                 215                 220

Asp His Arg Tyr Tyr Lys Gly Glu Leu Asn Trp Val Pro Leu Ile Gln
225                 230                 235                 240

Val Gly Asp Trp Phe Val His Met Asp Arg Thr Thr Met Lys Arg Lys
                245                 250                 255

Val Ile Ala Cys Ser Asp Gly Cys Lys Ala Leu Val Asp Thr Gly Thr
                260                 265                 270

Ser Asp Ile Val Gly Pro Ser Thr Leu Val Asn Ile Trp Lys Leu
            275                 280                 285

Ile Arg Ala Arg Pro Leu Gly Pro Gln Tyr Phe Val Ser Cys Ser Ala
            290                 295                 300

Val Asn Thr Leu Pro Ser Ile Ile Phe Thr Ile Asn Gly Ile Asn Tyr
305                 310                 315                 320

Arg Leu Pro Ala Arg Ala Tyr Ile His Lys Asp Ser Arg Gly Arg Cys
```

```
                    325                 330                 335
Tyr Thr Ala Phe Lys Glu His Arg Phe Ser Pro Ile Glu Thr Trp
                340                 345                 350

Leu Leu Gly Asp Val Phe Leu Arg Arg Tyr Phe Ser Val Phe Asp Arg
                355                 360                 365

Gly Asn Asp Arg Ile Gly Leu Ala Arg Ala Val
            370                 375

<210> SEQ ID NO 30
<211> LENGTH: 341
<212> TYPE: PRT
<213> ORGANISM: bovidae

<400> SEQUENCE: 30

Met Lys Trp Leu Val Leu Leu Gly Leu Val Ala Phe Ser Glu Cys Ile
  1               5                  10                  15

Val Lys Ile Pro Leu Arg Arg Val Lys Thr Met Arg Lys Thr Leu Ser
             20                  25                  30

Gly Lys Asn Met Leu Asn Asn Phe Leu Lys Glu Asp Pro Tyr Arg Leu
         35                  40                  45

Ser His Ile Ser Phe Arg Gly Ser Asn Leu Thr Ile His Pro Leu Arg
     50                  55                  60

Asn Ile Arg Asp Ile Phe Tyr Val Gly Asn Ile Thr Ile Gly Thr Pro
 65                  70                  75                  80

Pro Gln Glu Phe Gln Val Ile Phe Asp Thr Gly Ser Ser Asp Leu Trp
                 85                  90                  95

Val Pro Ser Ile Asp Cys Asn Ser Thr Ser Cys Ala Thr His Val Arg
            100                 105                 110

Phe Arg His Leu Gln Ser Ser Thr Phe Arg Pro Thr Asn Lys Thr Phe
        115                 120                 125

Arg Ile Ile Tyr Gly Ser Gly Arg Met Asn Gly Val Ile Ala Tyr Asp
    130                 135                 140

Thr Val Arg Ile Gly Asp Leu Val Ser Thr Asp Gln Pro Phe Gly Leu
145                 150                 155                 160

Ser Val Glu Glu Tyr Gly Phe Ala His Lys Arg Phe Asp Gly Ile Leu
                165                 170                 175

Gly Leu Asn Tyr Trp Asn Leu Ser Trp Ser Lys Ala Met Pro Ile Phe
            180                 185                 190

Asp Lys Leu Lys Asn Glu Gly Ala Ile Ser Glu Pro Val Phe Ala Phe
        195                 200                 205

Tyr Leu Ser Asn Ile Thr Met Asn Arg Glu Val Ile Ala Cys Ser Glu
    210                 215                 220

Gly Cys Ala Ala Leu Val Asp Thr Gly Ser Ser Asn Ile Gln Gly Pro
225                 230                 235                 240

Gly Arg Leu Ile Asp Asn Ile Gln Arg Ile Gly Ala Thr Pro Arg
                245                 250                 255

Gly Ser Lys Tyr Tyr Val Ser Cys Ser Ala Val Asn Ile Leu Pro Ser
            260                 265                 270

Ile Ile Phe Thr Ile Asn Gly Val Asn Tyr Pro Val Pro Pro Arg Ala
        275                 280                 285

Tyr Ile Leu Lys Asp Ser Arg Gly His Cys Tyr Thr Thr Phe Lys Glu
    290                 295                 300

Lys Arg Val Arg Arg Ser Thr Glu Ser Trp Val Leu Gly Glu Val Phe
305                 310                 315                 320
```

-continued

```
Leu Arg Leu Tyr Phe Ser Val Phe Asp Arg Gly Asn Asp Arg Ile Gly
                325                 330                 335
Leu Ala Arg Arg Val
            340

<210> SEQ ID NO 31
<211> LENGTH: 387
<212> TYPE: PRT
<213> ORGANISM: bovidae

<400> SEQUENCE: 31

Met Lys Trp Leu Val Leu Leu Gly Leu Val Ala Leu Ser Glu Cys Ile
 1               5                  10                  15
Val Lys Ile Pro Leu Thr Lys Met Lys Thr Met Gln Glu Ala Ile Arg
            20                  25                  30
Glu Lys Gln Leu Leu Glu Asp Phe Leu Asp Glu Gln Pro His Ser Leu
         35                 40                  45
Ser Gln His Ser Asp Pro Asp Lys Lys Phe Ser His Gln Leu Lys
     50                  55                  60
Asn Phe Gln Asn Ala Val Tyr Phe Gly Thr Ile Thr Ile Gly Thr Pro
 65                 70                  75                  80
Pro Gln Glu Phe Gln Val Asn Phe Asp Thr Gly Ser Ser Asp Leu Trp
                85                  90                  95
Val Pro Ser Val Asp Cys Gln Ser Pro Ser Cys Ser Lys His Lys Arg
            100                 105                 110
Phe Asp Pro Gln Lys Ser Thr Thr Phe Gln Pro Leu Asn Gln Lys Ile
        115                 120                 125
Glu Leu Val Tyr Gly Ser Gly Thr Met Lys Gly Val Leu Gly Ser Asp
    130                 135                 140
Thr Ile Gln Ile Gly Asn Leu Val Ile Val Asn Gln Ile Phe Gly Leu
145                 150                 155                 160
Ser Gln Asn Gln Ser Ser Gly Val Leu Glu Gln Val Pro Tyr Asp Gly
                165                 170                 175
Ile Leu Gly Leu Ala Tyr Pro Ser Leu Ala Ile Gln Gly Thr Thr Pro
            180                 185                 190
Val Phe Asp Asn Leu Lys Asn Arg Glu Val Ile Ser Glu Pro Val Phe
        195                 200                 205
Ala Phe Tyr Leu Ser Ser Arg Pro Glu Asn Ile Ser Thr Val Met Phe
    210                 215                 220
Gly Gly Val Asp His Thr Tyr His Lys Gly Lys Leu Gln Trp Ile Pro
225                 230                 235                 240
Val Thr Gln Ala Arg Phe Trp Gln Val Ala Met Ser Ser Met Thr Met
                245                 250                 255
Asn Gly Asn Val Val Gly Cys Ser Gln Gly Cys Gln Ala Val Val Asp
            260                 265                 270
Thr Gly Thr Ser Leu Leu Val Gly Pro Thr His Leu Val Thr Asp Ile
        275                 280                 285
Leu Lys Leu Ile Asn Pro Asn Pro Ile Leu Asn Asp Glu Gln Met Leu
    290                 295                 300
Ser Cys Asp Ala Ile Asn Ser Leu Pro Thr Leu Leu Thr Ile Asn
305                 310                 315                 320
Gly Ile Val Tyr Pro Val Pro Asp Tyr Tyr Ile Gln Arg Phe Ser
                325                 330                 335
Glu Arg Ile Cys Phe Ile Ser Phe Gln Gly Gly Thr Glu Ile Leu Lys
            340                 345                 350
```

```
Asn Leu Gly Thr Ser Glu Thr Trp Ile Leu Gly Asp Val Phe Leu Arg
            355                 360                 365

Leu Tyr Phe Ser Val Tyr Asp Arg Gly Asn Asn Arg Ile Gly Leu Ala
    370                 375                 380

Pro Ala Ala
385

<210> SEQ ID NO 32
<211> LENGTH: 379
<212> TYPE: PRT
<213> ORGANISM: bovidae

<400> SEQUENCE: 32

Met Lys Trp Ile Val Leu Leu Gly Leu Val Ala Phe Ser Glu Cys Ile
  1               5                  10                  15

Val Lys Ile Pro Leu Arg Gln Val Lys Thr Met Arg Lys Thr Leu Ser
             20                  25                  30

Gly Lys Asn Met Leu Lys Asn Phe Leu Lys Glu His Pro Tyr Arg Leu
         35                  40                  45

Ser Gln Ile Ser Phe Arg Gly Ser Asn Leu Thr Ile His Pro Leu Arg
     50                  55                  60

Asn Ile Met Asn Leu Val Tyr Val Gly Asn Ile Thr Ile Gly Thr Pro
 65                  70                  75                  80

Pro Gln Glu Phe Gln Val Val Phe Asp Thr Gly Ser Ser Asp Leu Trp
                 85                  90                  95

Val Pro Ser Phe Cys Thr Met Pro Ala Cys Ser Ala Pro Val Trp Phe
            100                 105                 110

Arg Gln Leu Gln Ser Ser Thr Phe Gln Pro Thr Asn Lys Thr Phe Thr
        115                 120                 125

Ile Thr Tyr Gly Ser Gly Ser Met Lys Gly Phe Leu Ala Tyr Asp Thr
    130                 135                 140

Val Arg Ile Gly Asp Leu Val Ser Thr Asp Gln Pro Phe Gly Leu Ser
145                 150                 155                 160

Val Val Glu Tyr Gly Leu Glu Gly Arg Asn Tyr Asp Gly Val Leu Gly
                165                 170                 175

Leu Asn Tyr Pro Asn Ile Ser Phe Ser Gly Ala Ile Pro Ile Phe Asp
            180                 185                 190

Asn Leu Lys Asn Gln Gly Ala Ile Ser Glu Pro Val Phe Ala Phe Tyr
        195                 200                 205

Leu Ser Lys Asn Lys Gln Glu Gly Ser Val Val Met Phe Gly Gly Val
    210                 215                 220

Asp His Gln Tyr Tyr Lys Gly Glu Leu Asn Trp Ile Pro Leu Ile Glu
225                 230                 235                 240

Ala Gly Glu Trp Arg Val His Met Asp Arg Ile Ser Met Lys Arg Thr
                245                 250                 255

Val Ile Ala Cys Ser Asp Gly Cys Glu Ala Leu Val His Thr Gly Thr
            260                 265                 270

Ser His Ile Glu Gly Pro Gly Arg Leu Val Asn Asn Ile His Arg Leu
        275                 280                 285

Ile Arg Thr Arg Pro Phe Asp Ser Lys His Tyr Val Ser Cys Phe Ala
    290                 295                 300

Thr Lys Tyr Leu Pro Ser Ile Thr Phe Ile Ile Asn Gly Ile Lys Tyr
305                 310                 315                 320

Pro Met Thr Ala Arg Ala Tyr Ile Phe Lys Asp Ser Arg Gly Arg Cys
```

```
                      325                 330                 335
Tyr Ser Ala Phe Lys Glu Asn Thr Val Arg Thr Ser Arg Glu Thr Trp
                340                 345                 350

Ile Leu Gly Asp Ala Phe Leu Arg Arg Tyr Phe Ser Val Phe Asp Arg
                355                 360                 365

Gly Asn Asp Arg Ile Gly Leu Ala Arg Ala Val
                370                 375

<210> SEQ ID NO 33
<211> LENGTH: 380
<212> TYPE: PRT
<213> ORGANISM: bovidae

<400> SEQUENCE: 33

Met Lys Trp Leu Gly Leu Leu Gly Leu Val Ala Leu Ser Glu Cys Met
  1               5                  10                  15

Val Ile Ile Pro Leu Arg Gln Met Lys Thr Met Arg Glu Thr Leu Arg
                 20                  25                  30

Glu Arg His Leu Leu Thr Asn Phe Ser Glu Glu His Pro Tyr Asn Leu
             35                  40                  45

Ser Gln Lys Ala Ala Asn Asp Gln Asn Ile Ile Tyr His His Pro Leu
         50                  55                  60

Arg Ser Tyr Lys Asp Phe Ser Tyr Ile Gly Asn Ile Asn Ile Gly Thr
 65                  70                  75                  80

Pro Pro Gln Glu Phe Gln Val Leu Phe Asp Thr Gly Ser Ser Ser Leu
                 85                  90                  95

Trp Val Pro Ser Ile Tyr Cys Gln Ser Ser Cys Tyr Lys His Asn
                100                 105                 110

Ser Phe Val Pro Cys Asn Ser Ser Thr Phe Lys Ala Thr Asn Lys Ile
            115                 120                 125

Phe Asn Thr Asn Tyr Thr Ala Thr Ser Ile Lys Gly Tyr Leu Val Tyr
        130                 135                 140

Asp Thr Val Arg Ile Gly Asn Leu Val Ser Val Ala Gln Pro Phe Gly
145                 150                 155                 160

Leu Ser Leu Lys Glu Phe Gly Phe Asp Asp Val Pro Phe Asp Gly Ile
                165                 170                 175

Leu Gly Leu Gly Tyr Pro Arg Arg Thr Ile Thr Gly Ala Asn Pro Ile
            180                 185                 190

Phe Asp Asn Leu Trp Lys Gln Gly Val Ile Ser Glu Pro Val Phe Ala
        195                 200                 205

Phe Tyr Leu Ser Ser Gln Lys Glu Asn Gly Ser Val Val Met Phe Gly
    210                 215                 220

Gly Val Asn Arg Ala Tyr Tyr Lys Gly Glu Leu Asn Trp Val Pro Val
225                 230                 235                 240

Ser Gln Val Gly Ser Trp His Ile Asn Ile Asp Ser Ile Ser Met Asn
                245                 250                 255

Gly Thr Val Val Ala Cys Lys Arg Gly Cys Gln Ala Ser Trp Ile Arg
            260                 265                 270

Gly Arg Leu Ser Ala Trp Pro Lys Arg Ile Val Ser Lys Ile Gln Lys
        275                 280                 285

Leu Ile His Ala Arg Pro Ile Asp Arg Glu His Val Val Ser Cys Gln
    290                 295                 300

Ala Ile Gly Thr Leu Pro Pro Ala Val Phe Thr Ile Asn Gly Ile Asp
305                 310                 315                 320
```

-continued

```
Tyr Pro Val Pro Ala Gln Ala Tyr Ile Gln Ser Leu Ser Gly Tyr Cys
            325                 330                 335

Phe Ser Asn Phe Leu Val Arg Pro Gln Arg Val Asn Glu Ser Glu Thr
            340                 345                 350

Trp Ile Leu Gly Asp Val Phe Leu Arg Leu Tyr Phe Ser Val Phe Asp
            355                 360                 365

Arg Gly Asn Asn Arg Ile Gly Leu Ala Pro Ala Val
            370                 375         380

<210> SEQ ID NO 34
<211> LENGTH: 376
<212> TYPE: PRT
<213> ORGANISM: bovidae

<400> SEQUENCE: 34

Met Lys Trp Leu Val Phe Leu Gly Leu Val Ala Phe Ser Glu Cys Ile
  1               5                  10                  15

Val Ile Met Leu Leu Thr Lys Thr Lys Thr Met Arg Glu Ile Trp Arg
             20                  25                  30

Glu Lys Lys Leu Leu Asn Ser Phe Leu Glu Glu Gln Ala Asn Arg Met
         35                  40                  45

Ser Asp Asp Ser Ala Ser Asp Pro Lys Leu Ser Thr His Pro Leu Arg
     50                  55                  60

Asn Ala Leu Asp Met Ala Tyr Val Gly Asn Ile Thr Ile Gly Thr Pro
 65                  70                  75                  80

Pro Lys Glu Phe Arg Val Val Phe Asp Thr Gly Ser Ser Asp Leu Trp
                 85                  90                  95

Val Pro Ser Ile Lys Cys Ile Ser Pro Ala Cys His Thr His Ile Thr
            100                 105                 110

Phe Asp His His Lys Ser Ser Thr Phe Arg Leu Thr Arg Arg Pro Phe
            115                 120                 125

His Ile Leu Tyr Gly Ser Gly Met Met Asn Gly Val Leu Ala Tyr Asp
            130                 135                 140

Thr Val Arg Ile Gly Lys Leu Val Ser Thr Asp Gln Pro Phe Gly Leu
145                 150                 155                 160

Ser Leu Gln Gln Phe Gly Phe Asp Asn Ala Pro Phe Asp Gly Val Leu
                165                 170                 175

Gly Leu Ser Tyr Pro Ser Leu Ala Val Pro Gly Thr Ile Pro Ile Phe
            180                 185                 190

Asp Lys Leu Lys Gln Gln Gly Ala Ile Ser Glu Pro Ile Phe Ala Phe
            195                 200                 205

Tyr Leu Ser Thr Arg Lys Glu Asn Gly Ser Val Leu Met Leu Gly Gly
            210                 215                 220

Val Asp His Ser Tyr His Lys Gly Lys Leu Asn Trp Ile Pro Val Ser
225                 230                 235                 240

Gln Thr Lys Ser Trp Leu Ile Thr Val Asp Arg Ile Ser Met Asn Gly
                245                 250                 255

Arg Val Ile Gly Cys Glu His Gly Cys Glu Ala Leu Val Asp Thr Gly
            260                 265                 270

Thr Ser Leu Ile His Gly Pro Ala Arg Pro Val Thr Asn Ile Gln Lys
            275                 280                 285

Phe Ile His Ala Met Pro Tyr Gly Ser Glu Tyr Met Val Leu Cys Pro
            290                 295                 300

Val Ile Ser Ile Leu Pro Pro Val Ile Phe Thr Ile Asn Gly Ile Asp
305                 310                 315                 320
```

```
Tyr Ser Val Pro Arg Glu Ala Tyr Ile Gln Lys Ile Ser Asn Ser Leu
            325                 330                 335

Cys Leu Ser Thr Phe His Gly Asp Asp Thr Asp Gln Trp Ile Leu Gly
            340                 345                 350

Asp Val Phe Leu Arg Leu Tyr Phe Ser Val Tyr Asp Arg Gly Asn Asn
            355                 360                 365

Arg Ile Gly Leu Ala Pro Ala Val
            370             375

<210> SEQ ID NO 35
<211> LENGTH: 375
<212> TYPE: PRT
<213> ORGANISM: bovidae

<400> SEQUENCE: 35

Met Lys Trp Leu Val Leu Leu Gly Leu Val Ala Leu Ser Glu Cys Ile
  1               5                  10                  15

Val Ile Leu Pro Leu Arg Lys Met Lys Thr Leu Arg Glu Thr Leu Arg
             20                  25                  30

Glu Lys Asn Leu Leu Asn Asn Phe Leu Glu Arg Ala Tyr Arg Leu
             35                  40                  45

Ser Lys Lys Asp Ser Lys Ile Thr Ile His Pro Leu Lys Asn Tyr Leu
 50                  55                  60

Asp Met Ala Tyr Val Gly Asn Ile Thr Ile Gly Thr Pro Pro Gln Glu
 65                  70                  75                  80

Phe Arg Val Val Phe Asp Thr Gly Ser Ala Asp Leu Trp Val Pro Ser
                 85                  90                  95

Ile Ser Cys Val Ser Pro Ala Cys Tyr Thr His Lys Thr Phe Asn Leu
            100                 105                 110

His Asn Ser Ser Ser Phe Gly Gln Thr His Gln Pro Ile Ser Ile Ser
            115                 120                 125

Tyr Gly Pro Gly Ile Ile Gln Gly Phe Leu Gly Ser Asp Thr Val Arg
            130                 135                 140

Ile Gly Asn Leu Val Ser Leu Lys Gln Ser Phe Gly Leu Ser Gln Glu
145                 150                 155                 160

Glu Tyr Gly Phe Asp Gly Ala Pro Phe Asp Gly Val Leu Gly Leu Ala
                165                 170                 175

Tyr Pro Ser Ile Ser Ile Lys Gly Ile Ile Pro Ile Phe Asp Asn Leu
            180                 185                 190

Trp Ser Gln Gly Ala Phe Ser Glu Pro Val Phe Ala Phe Tyr Leu Asn
            195                 200                 205

Thr Cys Gln Pro Glu Gly Ser Val Val Met Phe Gly Gly Val Asp His
            210                 215                 220

Arg Tyr Tyr Lys Gly Glu Leu Asn Trp Ile Pro Val Ser Gln Thr Arg
225                 230                 235                 240

Tyr Trp Gln Ile Ser Met Asn Arg Ile Ser Met Asn Gly Asn Val Thr
                245                 250                 255

Ala Cys Ser Arg Gly Cys Gln Ala Leu Leu Asp Thr Gly Thr Ser Met
            260                 265                 270

Ile His Gly Pro Thr Arg Leu Ile Thr Asn Ile His Lys Leu Met Asn
            275                 280                 285

Ala Arg His Gln Gly Ser Glu Tyr Val Val Ser Cys Asp Ala Val Lys
            290                 295                 300

Thr Leu Pro Pro Val Ile Phe Asn Ile Asn Gly Ile Asp Tyr Pro Leu
```

```
305                 310                 315                 320
Pro Pro Gln Ala Tyr Ile Thr Lys Ala Gln Asn Phe Cys Leu Ser Ile
                325                 330                 335

Phe His Gly Gly Thr Glu Thr Ser Ser Pro Glu Thr Trp Ile Leu Gly
                340                 345                 350

Gly Val Phe Leu Arg Gln Tyr Phe Ser Val Phe Asp Arg Arg Asn Asp
                355                 360                 365

Ser Ile Gly Leu Ala Gln Val
        370                 375

<210> SEQ ID NO 36
<211> LENGTH: 391
<212> TYPE: PRT
<213> ORGANISM: bovidae

<400> SEQUENCE: 36

Met Lys Trp Leu Val Leu Leu Gly Leu Val Ala Leu Ser Glu Cys Ile
  1               5                  10                  15

Val Ile Leu Pro Leu Lys Lys Met Lys Thr Leu Arg Glu Thr Leu Arg
                 20                  25                  30

Glu Lys Asn Leu Leu Asn Asn Phe Leu Glu Glu Gln Ala Tyr Arg Leu
             35                  40                  45

Ser Lys Asn Asp Ser Lys Ile Thr Ile His Pro Leu Arg Asn Tyr Leu
         50                  55                  60

Asp Thr Ala Tyr Val Gly Asn Ile Thr Ile Gly Thr Pro Pro Gln Glu
 65                  70                  75                  80

Phe Arg Val Val Phe Asp Thr Gly Ser Ala Asn Leu Trp Val Pro Cys
                 85                  90                  95

Ile Thr Cys Thr Ser Pro Ala Cys Tyr Thr His Lys Thr Phe Asn Pro
                100                 105                 110

Gln Asn Ser Ser Phe Arg Glu Val Gly Ser Pro Ile Thr Ile Phe
             115                 120                 125

Tyr Gly Ser Gly Ile Ile Gln Gly Phe Leu Gly Ser Asp Thr Val Arg
         130                 135                 140

Ile Gly Asn Leu Val Ser Leu Lys Gln Ser Phe Gly Leu Ser Gln Glu
145                 150                 155                 160

Glu Tyr Gly Phe Asp Gly Ala Pro Phe Asp Gly Val Leu Gly Leu Ala
                165                 170                 175

Tyr Pro Ser Ile Ser Ile Lys Gly Ile Ile Pro Ile Phe Asp Asn Leu
                180                 185                 190

Trp Ser His Gly Ala Phe Ser Glu Pro Val Phe Ala Phe Tyr Leu Asn
                195                 200                 205

Thr Asn Lys Pro Glu Gly Ser Val Val Met Phe Gly Gly Val Asp His
    210                 215                 220

Arg Tyr Tyr Lys Gly Glu Leu Asn Trp Ile Pro Val Ser Gln Thr Ser
225                 230                 235                 240

His Trp Gln Ile Ser Met Asn Asn Ile Ser Met Asn Gly Thr Val Thr
                245                 250                 255

Ala Cys Ser Cys Gly Cys Glu Ala Leu Leu Asp Thr Gly Thr Ser Met
                260                 265                 270

Ile Tyr Gly Pro Thr Lys Leu Val Thr Asn Ile His Lys Leu Met Asn
            275                 280                 285

Ala Arg Leu Glu Asn Ser Glu Tyr Val Val Ser Cys Asp Ala Val Lys
    290                 295                 300
```

```
Thr Leu Pro Pro Val Ile Phe Asn Ile Asn Gly Ile Asp Tyr Pro Leu
305                 310                 315                 320

Arg Pro Gln Ala Tyr Ile Ile Lys Ile Gln Asn Asn Cys Arg Ser Val
            325                 330                 335

Phe Gln Gly Gly Thr Glu Asn Ser Ser Leu Asn Thr Trp Ile Leu Gly
        340                 345                 350

Asp Ile Phe Leu Arg Gln Tyr Phe Ser Val Phe Asp Arg Lys Asn Arg
    355                 360                 365

Arg Ile Cys Trp His Arg Trp Val Pro Thr Thr Arg Thr Thr Met Thr
370                 375                 380

Ser Lys Leu Pro Pro Lys Leu
385                 390

<210> SEQ ID NO 37
<211> LENGTH: 392
<212> TYPE: PRT
<213> ORGANISM: bovidae

<400> SEQUENCE: 37

Met Lys Trp Leu Val Leu Leu Ala Leu Val Ala Phe Ser Glu Cys Ile
1               5                   10                  15

Ile Lys Ile Pro Leu Arg Arg Val Lys Thr Met Ser Asn Thr Ala Ser
            20                  25                  30

Gly Lys Asn Met Leu Asn Asn Phe Leu Lys Lys His Pro Tyr Arg Leu
        35                  40                  45

Ser Gln Ile Ser Phe Arg Gly Ser Asn Leu Thr Thr His Pro Leu Met
    50                  55                  60

Asn Ile Trp Asp Leu Leu Tyr Leu Gly Asn Ile Thr Ile Gly Thr Pro
65                  70                  75                  80

Pro Gln Glu Phe Gln Val Leu Phe Asp Thr Gly Ser Ser Asp Leu Trp
                85                  90                  95

Val Pro Ser Leu Leu Cys Asn Ser Ser Thr Cys Ala Lys His Val Met
            100                 105                 110

Phe Arg His Arg Leu Ser Ser Thr Tyr Arg Pro Thr Asn Lys Thr Phe
        115                 120                 125

Met Ile Phe Tyr Ala Val Gly Lys Ile Glu Gly Val Val Val Arg Asp
    130                 135                 140

Thr Val Arg Ile Gly Asp Leu Val Ser Ala Asp Gln Thr Phe Gly Leu
145                 150                 155                 160

Ser Ile Ala Glu Thr Gly Phe Glu Asn Thr Thr Leu Asp Gly Ile Leu
                165                 170                 175

Gly Leu Ser Tyr Pro Asn Thr Ser Cys Phe Gly Thr Ile Pro Ile Phe
            180                 185                 190

Asp Lys Leu Lys Asn Glu Gly Ala Ile Ser Glu Pro Val Leu His Ser
        195                 200                 205

Val Arg Arg Lys Asp Glu Gln Glu Gly Ser Val Val Met Phe Gly Gly
    210                 215                 220

Val Asp His Ser Tyr Tyr Lys Gly Glu Leu Asn Trp Val Pro Leu Ile
225                 230                 235                 240

Lys Ala Gly Asp Trp Ser Val Arg Val Asp Ser Ile Thr Met Lys Arg
                245                 250                 255

Glu Val Ile Ala Cys Ser Asp Gly Cys Arg Ala Leu Val Asp Thr Gly
            260                 265                 270

Ser Ser His Ile Gln Gly Pro Gly Arg Leu Ile Asp Asn Val Gln Lys
        275                 280                 285
```

-continued

```
Leu Ile Gly Thr Met Pro Gln Gly Ser Met His Tyr Val Pro Cys Ser
    290                 295                 300

Ala Val Asn Thr Leu Pro Ser Ile Ile Phe Thr Ile Asn Ser Ile Ser
305                 310                 315                 320

Tyr Thr Val Pro Ala Gln Ala Tyr Ile Leu Lys Gly Ser Arg Gly Arg
                325                 330                 335

Cys Tyr Ser Thr Phe Gln Gly His Thr Met Ser Ser Ser Thr Glu Thr
                340                 345                 350

Trp Ile Leu Gly Asp Val Phe Leu Ser Gln Tyr Phe Ser Val Phe Asp
            355                 360                 365

Arg Gly Asn Asp Arg Ile Gly Leu Ala Gln Val Gly Thr Asp Tyr Lys
    370                 375                 380

Asp Asp Asp Glu Ser Pro Lys Leu
385                 390

<210> SEQ ID NO 38
<211> LENGTH: 388
<212> TYPE: PRT
<213> ORGANISM: Felis domestica

<400> SEQUENCE: 38

Met Lys Trp Leu Trp Val Leu Gly Leu Val Ala Leu Ser Glu Cys Leu
  1               5                  10                  15

Val Thr Ile Pro Leu Thr Arg Val Lys Ser Met Arg Glu Asn Leu Arg
                 20                  25                  30

Glu Lys Asp Arg Leu Lys Asp Phe Leu Glu Asn His Pro Tyr Asn Leu
             35                  40                  45

Ala Tyr Lys Phe Val Asp Ser Val Asn Leu Asp Leu Gly Ile Tyr Phe
         50                  55                  60

Glu Pro Met Arg Asn Tyr Leu Asp Leu Ala Tyr Val Gly Thr Ile Ser
 65                  70                  75                  80

Ile Gly Thr Pro Pro Gln Glu Phe Lys Val Ile Phe Asp Thr Gly Ser
                 85                  90                  95

Ser Asp Leu Trp Val Pro Ser Ile Tyr Cys Ser Ser Pro Ala Cys Ala
                100                 105                 110

Asn His Asn Val Phe Asn Pro Leu Arg Ser Ser Thr Phe Arg Ile Ser
            115                 120                 125

Gly Arg Pro Ile His Leu Gln Tyr Gly Ser Gly Thr Met Ser Gly Phe
        130                 135                 140

Leu Ala Tyr Asp Thr Val Arg Phe Gly Gly Leu Val Asp Val Ala Gln
145                 150                 155                 160

Ala Phe Gly Leu Ser Leu Arg Glu Pro Gly Lys Phe Met Glu Tyr Ala
                165                 170                 175

Val Phe Asp Gly Ile Leu Gly Leu Ala Tyr Pro Ser Leu Ser Leu Arg
            180                 185                 190

Gly Thr Val Pro Val Phe Asp Asn Leu Trp Lys Gln Gly Leu Ile Ser
        195                 200                 205

Gln Glu Leu Phe Ala Phe Tyr Leu Ser Lys Lys Asp Glu Glu Gly Ser
    210                 215                 220

Val Val Met Phe Gly Gly Val Asp His Ser Tyr Tyr Ser Gly Asp Leu
225                 230                 235                 240

Asn Trp Val Pro Val Ser Lys Arg Leu Tyr Trp Gln Leu Ser Met Asp
                245                 250                 255

Ser Ile Ser Met Asn Gly Glu Val Ile Ala Cys Asp Gly Gly Cys Gln
```

```
              260                 265                 270
Ala Ile Ile Asp Thr Gly Thr Ser Leu Leu Ile Gly Pro Ser His Val
            275                 280                 285
Val Phe Asn Ile Gln Met Ile Ile Gly Ala Asn Gln Ser Tyr Ser Gly
            290                 295                 300
Glu Tyr Val Val Asp Cys Asp Ala Ala Asn Thr Leu Pro Asp Ile Val
305                 310                 315                 320
Phe Thr Ile Asn Gly Ile Asp Tyr Pro Val Pro Ala Ser Ala Tyr Ile
                325                 330                 335
Gln Glu Gly Pro Gln Gly Thr Cys Tyr Ser Gly Phe Asp Glu Ser Gly
            340                 345                 350
Asp Ser Leu Leu Val Ser Asp Ser Trp Ile Leu Gly Asp Val Phe Leu
            355                 360                 365
Arg Leu Tyr Phe Thr Val Phe Asp Arg Glu Asn Asn Arg Ile Gly Leu
            370                 375                 380
Ala Leu Ala Val
385

<210> SEQ ID NO 39
<211> LENGTH: 1158
<212> TYPE: DNA
<213> ORGANISM: bovidae

<400> SEQUENCE: 39
aggaaagaag catgaagtgg cttgtggtcc tcgggctggt ggccttctca gagtgcatag       60
tcaaaatacc tctaaggaga gtgaagacca tgagaaaaac tctcagtgga aaaaacatgc      120
tgaacaattt cttgaaggag gatccttaca gactgtccca gatttctttt cgtggctcaa      180
atctaactat tcaccgctg agaaacatca gagatatctt ctatgtcgga acatcacca        240
ttggaacacc ccctcaggaa ttccaggtta tctttgacac aggctcatct gacttgtggg      300
tgccctcgat cgattgcaac agtacatcct gtgctacaca tgttaggttc agacatcttc      360
agtcttccac cttccggcct accaataaga ccttcaggat catctatgga tctgggagaa      420
tgaacggagt tattgcttat gacacagttc ggattgggga ccttgtaagt accgaccagc      480
catttggtct aagcgtggag gaatatgggt ttgcgcacaa agatttgat ggcatcttgg       540
gcttgaacta ctggaaccta tcctggtcta aggccatgcc catctttgac aagctgaaga      600
atgaaggcgc catttctgag cctgtttttg ccttctactt gagcaaagac aagcgggagg      660
gcagtgtggt gatgtttggt ggggtggacc accgctacta caaggagag ctcaagtggg      720
taccactgat ccaagcagtc gactggagtg tacacgtaga ccgcatcacc atgaacagag      780
aggttattgc ttgttctgaa ggctgtgcgg cccttgtgga cactgggtca tcaaatatcc      840
aaggcccaag aagactgatt gataacatac agaggatcat cggcgccacg ccacggggtt      900
ccaagtacta cgtttcatgt tctgcggtca atatcctgcc ctctattatc ttccaccatca     960
acggcgtcaa ctacccagtg ccacctcgag cttacatcct caaggattct agaggccact     1020
gctataccac ctttaaagag aaaagagtga ggagatctac agagagctgg gtcctgggtg     1080
aagtcttcct gaggctgtat ttctcagtct tgatcgagg aaatgacagg attggcctgg      1140
cacgggcagt gtaactcg                                                   1158

<210> SEQ ID NO 40
<211> LENGTH: 380
<212> TYPE: PRT
<213> ORGANISM: bovidae
```

<400> SEQUENCE: 40

```
Met Lys Trp Leu Val Val Leu Gly Leu Val Ala Phe Ser Glu Cys Ile
 1               5                  10                  15
Val Lys Ile Pro Leu Arg Arg Val Lys Thr Met Arg Lys Thr Leu Ser
            20                  25                  30
Gly Lys Asn Met Leu Asn Asn Phe Leu Lys Glu Asp Pro Tyr Arg Leu
        35                  40                  45
Ser Gln Ile Ser Phe Arg Gly Ser Asn Leu Thr Ile His Pro Leu Arg
    50                  55                  60
Asn Ile Arg Asp Ile Phe Tyr Val Gly Asn Ile Thr Ile Gly Thr Pro
 65                  70                  75                  80
Pro Gln Glu Phe Gln Val Ile Phe Asp Thr Gly Ser Ser Asp Leu Trp
                85                  90                  95
Val Pro Ser Ile Asp Cys Asn Ser Thr Ser Cys Ala Thr His Val Arg
            100                 105                 110
Phe Arg His Leu Gln Ser Ser Thr Phe Arg Pro Thr Asn Lys Thr Phe
        115                 120                 125
Arg Ile Ile Tyr Gly Ser Gly Arg Met Asn Gly Val Ile Ala Tyr Asp
    130                 135                 140
Thr Val Arg Ile Gly Asp Leu Val Ser Thr Asp Gln Pro Phe Gly Leu
145                 150                 155                 160
Ser Val Glu Glu Tyr Gly Phe Ala His Lys Arg Phe Asp Gly Ile Leu
                165                 170                 175
Gly Leu Asn Tyr Trp Asn Leu Ser Trp Ser Lys Ala Met Pro Ile Phe
            180                 185                 190
Asp Lys Leu Lys Asn Glu Gly Ala Ile Ser Glu Pro Val Phe Ala Phe
        195                 200                 205
Tyr Leu Ser Lys Asp Lys Arg Glu Gly Ser Val Val Met Phe Gly Gly
    210                 215                 220
Val Asp His Arg Tyr Tyr Lys Gly Glu Leu Lys Trp Val Pro Leu Ile
225                 230                 235                 240
Gln Ala Val Asp Trp Ser Val His Val Asp Arg Ile Thr Met Asn Arg
                245                 250                 255
Glu Val Ile Ala Cys Ser Glu Gly Cys Ala Ala Leu Val Asp Thr Gly
            260                 265                 270
Ser Ser Asn Ile Gln Gly Pro Arg Arg Leu Ile Asp Asn Ile Gln Arg
        275                 280                 285
Ile Ile Gly Ala Thr Pro Arg Gly Ser Lys Tyr Tyr Val Ser Cys Ser
    290                 295                 300
Ala Val Asn Ile Leu Pro Ser Ile Ile Phe Thr Ile Asn Gly Val Asn
305                 310                 315                 320
Tyr Pro Val Pro Pro Arg Ala Tyr Ile Leu Lys Asp Ser Arg Gly His
                325                 330                 335
Cys Tyr Thr Thr Phe Lys Glu Lys Arg Val Arg Ser Thr Glu Ser
            340                 345                 350
Trp Val Leu Gly Glu Val Phe Leu Arg Leu Tyr Phe Ser Val Phe Asp
        355                 360                 365
Arg Gly Asn Asp Arg Ile Gly Leu Ala Arg Ala Val
    370                 375                 380
```

<210> SEQ ID NO 41
<211> LENGTH: 1155
<212> TYPE: DNA

<213> ORGANISM: bovidae

<400> SEQUENCE: 41

```
aggaaagaag catgaagtgg attgtgctcc tcgggctgat ggccttctca gagtgcatag     60
tccaaatacc tctaaggcaa gtgaagacca tgagaaaaac cctcagtgga aaaaacatgc    120
tgaagaattt cttgaaggag catccttaca gactgtccca gatttctttt cgtggctcaa    180
atctaactat tcacccgctg aggaacatca tgaatttggt ctacgtgggt aacatcacca    240
ttggaacacc ccctcaggaa ttccaggttg tctttgacac aggctcatct gacttgtggg    300
tgccctcctt ttgtaccatg ccagcatgct ctgcaccggt tggttcaga caacttcagt     360
cttccacctt ccagcctacc aataagacct tcaccatcac ctatggatct gggagcatga    420
agggatttct tgcttatgac acagttcgga ttggggacct tgtaagtact gatcagccgt    480
tcggtctaag cgtggtggaa tatgggttgg agggcagaaa ttatgatggt gccttgggct    540
tgaactaccc caacatatcc ttctctggag ccatccccat ctttgacaac ctgaagaatc    600
aaggtgccat ttctgagcct gtttttgcct tctacttgag caaaaacaag caggagggca    660
gtgtggtgat gtttggtggg gtggaccacc agtactacaa gggagagctc aactggatac    720
cactgattga agcaggcgaa tggagagtac acatggaccg catctccatg aaaagaacgg    780
ttattgcttg ttctgatggc tgtgaggccc ttgtgcacac tgggacatca catatcgaag    840
gcccaggaag actggtgaat aacatacaca ggctcatccg caccaggcca tttgattcca    900
agcactacgt ttcatgtttt gccaccaata ccctgccctc tattactttc atcatcaacg    960
gcatcaagta cccaatgaca gctcgagcct acatctttaa ggattctaga ggccgctgct   1020
attccgcttt taaagagaac acagtgagaa catctagaga gacctggatc ctcggtgatg   1080
ccttcctgag gcggtatttc tcagtctttg atcgaggaaa tgacaggatt ggcctggcac   1140
gggcagtgta actcg                                                    1155
```

<210> SEQ ID NO 42
<211> LENGTH: 379
<212> TYPE: PRT
<213> ORGANISM: bovidae

<400> SEQUENCE: 42

```
Met Lys Trp Ile Val Leu Leu Gly Leu Met Ala Phe Ser Glu Cys Ile
  1               5                  10                  15

Val Gln Ile Pro Leu Arg Gln Val Lys Thr Met Arg Lys Thr Leu Ser
             20                  25                  30

Gly Lys Asn Met Leu Lys Asn Phe Leu Lys Glu His Pro Tyr Arg Leu
         35                  40                  45

Ser Gln Ile Ser Phe Arg Gly Ser Asn Leu Thr Ile His Pro Leu Arg
     50                  55                  60

Asn Ile Met Asn Leu Val Tyr Val Gly Asn Ile Thr Ile Gly Thr Pro
 65                  70                  75                  80

Pro Gln Glu Phe Gln Val Val Phe Asp Thr Gly Ser Ser Asp Leu Trp
                 85                  90                  95

Val Pro Ser Phe Cys Thr Met Pro Ala Cys Ser Ala Pro Val Trp Phe
            100                 105                 110

Arg Gln Leu Gln Ser Ser Thr Phe Gln Pro Thr Asn Lys Thr Phe Thr
        115                 120                 125

Ile Thr Tyr Gly Ser Gly Ser Met Lys Gly Phe Leu Ala Tyr Asp Thr
    130                 135                 140
```

```
Val Arg Ile Gly Asp Leu Val Ser Thr Asp Gln Pro Phe Gly Leu Ser
145                 150                 155                 160

Val Val Glu Tyr Gly Leu Glu Gly Arg Asn Tyr Asp Gly Ala Leu Gly
                165                 170                 175

Leu Asn Tyr Pro Asn Ile Ser Phe Ser Gly Ala Ile Pro Ile Phe Asp
            180                 185                 190

Asn Leu Lys Asn Gln Gly Ala Ile Ser Glu Pro Val Phe Ala Phe Tyr
        195                 200                 205

Leu Ser Lys Asn Lys Gln Glu Gly Ser Val Val Met Phe Gly Gly Val
    210                 215                 220

Asp His Gln Tyr Tyr Lys Gly Glu Leu Asn Trp Ile Pro Leu Ile Glu
225                 230                 235                 240

Ala Gly Glu Trp Arg Val His Met Asp Arg Ile Ser Met Lys Arg Thr
                245                 250                 255

Val Ile Ala Cys Ser Asp Gly Cys Glu Ala Leu Val His Thr Gly Thr
            260                 265                 270

Ser His Ile Glu Gly Pro Gly Arg Leu Val Asn Asn Ile His Arg Leu
        275                 280                 285

Ile Arg Thr Arg Pro Phe Asp Ser Lys His Tyr Val Ser Cys Phe Ala
    290                 295                 300

Thr Asn Thr Leu Pro Ser Ile Thr Phe Ile Ile Asn Gly Ile Lys Tyr
305                 310                 315                 320

Pro Met Thr Ala Arg Ala Tyr Ile Phe Lys Asp Ser Arg Gly Arg Cys
                325                 330                 335

Tyr Ser Ala Phe Lys Glu Asn Thr Val Arg Thr Ser Arg Glu Thr Trp
            340                 345                 350

Ile Leu Gly Asp Ala Phe Leu Arg Arg Tyr Phe Ser Val Phe Asp Arg
        355                 360                 365

Gly Asn Asp Arg Ile Gly Leu Ala Arg Ala Val
    370                 375

<210> SEQ ID NO 43
<211> LENGTH: 1154
<212> TYPE: DNA
<213> ORGANISM: bovidae

<400> SEQUENCE: 43
aggaaagaag catgaagtgg cttgtgctcc tagggctggt ggccttctca gagtgcgtag      60
tcaaaatacc tctaaggaga gtgaagacca tgacaaaaac cctcagtggg aaaaacatgc     120
tgaacaattt cctgaaggag catgcttaca gactgtccca gatttctttt catggctcaa     180
atctaactat tcacccgctg agaaacatca gggatttgtt ctacatgggt aacatcacca     240
ttggaacacc ccctcaggaa ttcctggttg tctttgacac aggctcatct gacttgtggg     300
ttccctccga cttttgcacc agtccagcct gttctaaaca ctttaggttc agacatcttc     360
agtcttccac attccggctt accaataaga ccttcagcat gaatacggga tctgggacaa     420
tggaaggaat tgttgctcat gacacagttc ggattgggga ccttgtaagc actgaccagc     480
cgtttggtct aagcatgaca gaatccgggt tgagggtat accttttgat ggcgtcttgg     540
gcttgaacta ccccaacata tccttctctg agccatccc catctttgac aagctgaaga     600
atcaaggtgc catttctgag cctgttttg ccttctattt gagcaaagac gagcaggagg     660
gcagtgtggt gatgtttggt ggggtggacc accgctacta caaggagag ctcaaatggg     720 taccattgat tgaagcgggt gactggattg tacacatgga ctgcatctcc atgagaagaa     780
```

```
aggttattgc ttgttctggc ggctgtgagg ccgttgttga caccggggta tcaatgatca    840
aaggcccaaa acactggtt gataacatcc agaagctcat cggtgccact ctacggggtt    900
tcaagcacta cgtttcatgt tctgcagtcg atacccctgcc ctctattacc ttcaccataa    960
acggtatcaa ctaccgagtg ccagctcgag cctacatcct caaggattct agaggctgct   1020
gctatagcag ctttcaagag accactgtga gtccatctac agagacctgg atcctgggtg   1080
acgtcttcct gagactgtat ttctcagtct ttgatcgagg aaatgacagg attgggctgg   1140
cacgggcagt gtaa                                                     1154
```

<210> SEQ ID NO 44
<211> LENGTH: 380
<212> TYPE: PRT
<213> ORGANISM: bovidae

<400> SEQUENCE: 44

```
Met Lys Trp Leu Val Leu Leu Gly Leu Val Ala Phe Ser Glu Cys Val
  1               5                  10                  15

Val Lys Ile Pro Leu Arg Arg Val Lys Thr Met Thr Lys Thr Leu Ser
             20                  25                  30

Gly Lys Asn Met Leu Asn Asn Phe Leu Lys Glu His Ala Tyr Arg Leu
         35                  40                  45

Ser Gln Ile Ser Phe His Gly Ser Asn Leu Thr Ile His Pro Leu Arg
     50                  55                  60

Asn Ile Arg Asp Leu Phe Tyr Met Gly Asn Ile Thr Ile Gly Thr Pro
 65                  70                  75                  80

Pro Gln Glu Phe Leu Val Val Phe Asp Thr Gly Ser Ser Asp Leu Trp
                 85                  90                  95

Val Pro Ser Asp Phe Cys Thr Ser Pro Ala Cys Ser Lys His Phe Arg
            100                 105                 110

Phe Arg His Leu Gln Ser Ser Thr Phe Arg Leu Thr Asn Lys Thr Phe
        115                 120                 125

Ser Ile Glu Tyr Gly Ser Gly Thr Met Glu Gly Ile Val Ala His Asp
    130                 135                 140

Thr Val Arg Ile Gly Asp Leu Val Ser Thr Asp Gln Pro Phe Gly Leu
145                 150                 155                 160

Ser Met Thr Glu Ser Gly Phe Glu Gly Ile Pro Phe Asp Gly Val Leu
                165                 170                 175

Gly Leu Asn Tyr Pro Asn Ile Ser Phe Ser Gly Ala Ile Pro Ile Phe
            180                 185                 190

Asp Lys Leu Lys Asn Gln Gly Ala Ile Ser Glu Pro Val Phe Ala Phe
        195                 200                 205

Tyr Leu Ser Lys Asp Glu Gln Glu Gly Ser Val Val Met Phe Gly Gly
    210                 215                 220

Val Asp His Arg Tyr Tyr Lys Gly Glu Leu Lys Trp Val Pro Leu Ile
225                 230                 235                 240

Glu Ala Gly Asp Trp Ile Val His Met Asp Cys Ile Ser Met Arg Arg
                245                 250                 255

Lys Val Ile Ala Cys Ser Gly Gly Cys Glu Ala Val Val Asp Thr Gly
            260                 265                 270

Val Ser Met Ile Lys Gly Pro Lys Thr Leu Val Asp Asn Ile Gln Lys
        275                 280                 285

Leu Ile Gly Ala Thr Leu Arg Gly Phe Lys His Tyr Val Ser Cys Ser
    290                 295                 300
```

```
Ala Val Asp Thr Leu Pro Ser Ile Thr Phe Thr Ile Asn Gly Ile Asn
305                 310                 315                 320

Tyr Arg Val Pro Ala Arg Ala Tyr Ile Leu Lys Asp Ser Arg Gly Cys
            325                 330                 335

Cys Tyr Ser Ser Phe Gln Glu Thr Thr Val Ser Pro Ser Thr Glu Thr
            340                 345                 350

Trp Ile Leu Gly Asp Val Phe Leu Arg Leu Tyr Phe Ser Val Phe Asp
        355                 360                 365

Arg Gly Asn Asp Arg Ile Gly Leu Ala Arg Ala Val
    370                 375                 380

<210> SEQ ID NO 45
<211> LENGTH: 1168
<212> TYPE: DNA
<213> ORGANISM: bovidae

<400> SEQUENCE: 45
```

| | | | | | |
|---|---|---|---|---|---|
| aggaaagaag | catgaagtgg | cttgtgctcc | tcgggctggt | ggccttctca | gagtgcatag | 60 |
| tcaaatacc | tctaaggaga | gtgaagacca | tgagaaaaac | cctcagtgga | aaaaacacgc | 120 |
| tgaacaattt | cttgaaggag | catccttaca | gactgtccca | tatttctttt | cgtggctcaa | 180 |
| atctaactac | tctgccgctg | agaaacatca | gagatatgct | ctacgtgggt | aacatcacca | 240 |
| ttggaacacc | ccctcaagaa | ttccaggttg | tctttgacac | aggttcatct | gacttgtggg | 300 |
| tgccctctga | cttttgcacc | agtccagcct | gttctacaca | cgttaggttc | agacattttc | 360 |
| agtcttccac | cttccggcct | accactaaga | ccttcaggat | catctatgga | tctgggagaa | 420 |
| tgaaaggagt | tgttgcgcat | gacacagttc | ggattgggaa | ccttgtaagt | actgaccagc | 480 |
| cgttcggcct | aagcatggcg | aatacgggt | tggagagcag | aagatttgat | ggcatcttgg | 540 |
| gcttgaacta | ccccaatcta | tcctgctctg | ggccattcc | catctttgat | aagctgaaga | 600 |
| atcaaggtgc | catttctgat | cctatttttg | ccttctactt | gagcaaagac | aagcgagagg | 660 |
| gcagtgtggt | gatgtttggt | ggggtggacc | accgctacta | caagggagag | ctcaactggg | 720 |
| taccactgat | tcgagcaggt | gactggattg | tacacgtaga | ccgcatcacc | atgaaaagag | 780 |
| aggttattgc | ttgttctgat | ggctgcgcgg | cccttgtgga | cactgggaca | tcacttatcc | 840 |
| aaggcccagg | aagagtgatc | gataacatac | acaagctcat | tggtgccacg | ccacgggggtt | 900 |
| ccaagcatta | cgtttcatgt | tctgtggtca | atactctgcc | ctctattatc | ttcaccatca | 960 |
| atggcatcaa | ctacccagtg | ccagctccag | cctacatcct | caaggattct | agaggctact | 1020 |
| gctataccgc | ctttaaagag | caaagagtga | ggagatctac | agagagctgg | ttactgggtg | 1080 |
| acgtcttcct | gaggctgtat | ttctcagtct | ttgatcgagg | aaatgacagg | attggcctgg | 1140 |
| cacgggcagt | gtaactcgaa | tcactagt | | | | 1168 |

```
<210> SEQ ID NO 46
<211> LENGTH: 380
<212> TYPE: PRT
<213> ORGANISM: bovidae

<400> SEQUENCE: 46

Met Lys Trp Leu Val Leu Leu Gly Leu Val Ala Phe Ser Glu Cys Ile
1               5                   10                  15

Val Lys Ile Pro Leu Arg Arg Val Lys Thr Met Arg Lys Thr Leu Ser
            20                  25                  30

Gly Lys Asn Thr Leu Asn Asn Phe Leu Lys Glu His Pro Tyr Arg Leu
        35                  40                  45
```

```
Ser His Ile Ser Phe Arg Gly Ser Asn Leu Thr Thr Leu Pro Leu Arg
 50                  55                  60

Asn Ile Arg Asp Met Leu Tyr Val Gly Asn Ile Thr Ile Gly Thr Pro
 65                  70                  75                  80

Pro Gln Glu Phe Gln Val Val Phe Asp Thr Gly Ser Ser Asp Leu Trp
                 85                  90                  95

Val Pro Ser Asp Phe Cys Thr Ser Pro Ala Cys Ser His Val Arg
             100                 105                 110

Phe Arg His Phe Gln Ser Ser Thr Phe Arg Pro Thr Thr Lys Thr Phe
             115                 120                 125

Arg Ile Ile Tyr Gly Ser Gly Arg Met Lys Gly Val Ala His Asp
 130                 135                 140

Thr Val Arg Ile Gly Asn Leu Val Ser Thr Asp Gln Pro Phe Gly Leu
145                 150                 155                 160

Ser Met Ala Glu Tyr Gly Leu Glu Ser Arg Arg Phe Asp Gly Ile Leu
                165                 170                 175

Gly Leu Asn Tyr Pro Asn Leu Ser Cys Ser Gly Ala Ile Pro Ile Phe
                180                 185                 190

Asp Lys Leu Lys Asn Gln Gly Ala Ile Ser Asp Pro Ile Phe Ala Phe
            195                 200                 205

Tyr Leu Ser Lys Asp Lys Arg Glu Gly Ser Val Val Met Phe Gly Gly
210                 215                 220

Val Asp His Arg Tyr Tyr Lys Gly Glu Leu Asn Trp Val Pro Leu Ile
225                 230                 235                 240

Arg Ala Gly Asp Trp Ile Val His Val Asp Arg Ile Thr Met Lys Arg
                245                 250                 255

Glu Val Ile Ala Cys Ser Asp Gly Cys Ala Ala Leu Val Asp Thr Gly
                260                 265                 270

Thr Ser Leu Ile Gln Gly Pro Gly Arg Val Ile Asp Asn Ile His Lys
        275                 280                 285

Leu Ile Gly Ala Thr Pro Arg Gly Ser Lys His Tyr Val Ser Cys Ser
290                 295                 300

Val Val Asn Thr Leu Pro Ser Ile Ile Phe Thr Ile Asn Gly Ile Asn
305                 310                 315                 320

Tyr Pro Val Pro Ala Pro Ala Tyr Ile Leu Lys Asp Ser Arg Gly Tyr
                325                 330                 335

Cys Tyr Thr Ala Phe Lys Glu Gln Arg Val Arg Arg Ser Thr Glu Ser
            340                 345                 350

Trp Leu Leu Gly Asp Val Phe Leu Arg Leu Tyr Phe Ser Val Phe Asp
        355                 360                 365

Arg Gly Asn Asp Arg Ile Gly Leu Ala Arg Ala Val
        370                 375                 380

<210> SEQ ID NO 47
<211> LENGTH: 1158
<212> TYPE: DNA
<213> ORGANISM: bovidae

<400> SEQUENCE: 47
aggaaagaag catgaagtgg cttgtgctcc tctggctagt ggccttctca gagtgtatag      60 tcaaatacc tctaaggcaa gtgaagacca tgagaaaaac cctcagtgga aaaacacgc      120 tgaacaattt cttgaggaa catacttaca gtctgtccca gatttcttct cgtggttcaa     180
atctaactat tcacccactg agaaacatca tggatatgct ctacgtgggt aacatcacca   240
```

```
ttggaacacc ccctcaggaa ttccaggttg tctttgacac aggctcatct gacttgtggg    300
tgccctccgt cttttgccaa agtctagcct gtgctacaaa ggttatgttc atacatcttc    360
attcttccac cttccggcat acccaaaagg tcttcaacat caagtacaat actggaagga    420
tgaaaggact tcttgtttat gacactgttc ggattgggga ccttgtaagt actgaccagc    480
cattctgtat aagcctggca gaagttgggt ttgacggtat accttttgat ggtgtcttgg    540
gcttgaacta tccgaacatg tccttctctg gagccatccc catctttgac aacctgaaga    600
atgaaggtgc catttctgag cctgtttttg ccttctactt gagcaaagac aagcgggagg    660
gcagtgtggt gatgtttggt ggggtggacc accgctacta caagggagag ctcaactggg    720
tgccattgat ccaagcgggc ggctggactg tacacgtgga ccgcatctcc atgaaaagaa    780
agattattgc ttgttctgga ggctgcgagg cccttgtgga caccggaaca gcactgatca    840
aaggcccaag aagactggtc aataacatac agaagctcat cggcaccacg ccacggggtt    900
ccaagcacta cgtttcatgt tctgtggtca ataccctgcc ctctattatc ttcaccatca    960
acggcatcaa ctaccggtg ccagcacgag cctacatcct caaggattct gaaagcaact   1020
gctatacaac ctttaaagag aacacagtga ggacgtctag agagacctgg atcctgggtg   1080
acgtcttccc gaggctgtat ttctcagtct tgatcgagg aaatgacagg attggcctgg   1140
cacgggcagt gtaactcg                                                1158
```

<210> SEQ ID NO 48
<211> LENGTH: 380
<212> TYPE: PRT
<213> ORGANISM: bovidae

<400> SEQUENCE: 48

```
Met Lys Trp Leu Val Leu Leu Trp Leu Val Ala Phe Ser Glu Cys Ile
  1               5                  10                  15

Val Lys Ile Pro Leu Arg Gln Val Lys Thr Met Arg Lys Thr Leu Ser
             20                  25                  30

Gly Lys Asn Thr Leu Asn Asn Phe Leu Lys Glu His Thr Tyr Ser Leu
         35                  40                  45

Ser Gln Ile Ser Ser Arg Gly Ser Asn Leu Thr Ile His Pro Leu Arg
     50                  55                  60

Asn Ile Met Asp Met Leu Tyr Val Gly Asn Ile Thr Ile Gly Thr Pro
 65                  70                  75                  80

Pro Gln Glu Phe Gln Val Val Phe Asp Thr Gly Ser Ser Asp Leu Trp
                 85                  90                  95

Val Pro Ser Val Phe Cys Gln Ser Leu Ala Cys Ala Thr Lys Val Met
            100                 105                 110

Phe Ile His Leu His Ser Ser Thr Phe Arg His Thr Gln Lys Val Phe
        115                 120                 125

Asn Ile Lys Tyr Asn Thr Gly Arg Met Lys Gly Leu Leu Val Tyr Asp
    130                 135                 140

Thr Val Arg Ile Gly Asp Leu Val Ser Thr Asp Gln Pro Phe Cys Ile
145                 150                 155                 160

Ser Leu Ala Glu Val Gly Phe Asp Gly Ile Pro Phe Asp Gly Val Leu
                165                 170                 175

Gly Leu Asn Tyr Pro Asn Met Ser Phe Ser Gly Ala Ile Pro Ile Phe
            180                 185                 190

Asp Asn Leu Lys Asn Glu Gly Ala Ile Ser Glu Pro Val Phe Ala Phe
        195                 200                 205
```

-continued

| | | | | | | | | | | | |
|---|---|---|---|---|---|---|---|---|---|---|---|
|Tyr|Leu|Ser|Lys|Asp|Lys|Arg|Glu|Gly|Ser|Val|Val|Met|Phe|Gly|Gly|
| |210| | | |215| | | |220| | |

Val Asp His Arg Tyr Tyr Lys Gly Glu Leu Asn Trp Val Pro Leu Ile
225                 230                 235                 240

Gln Ala Gly Gly Trp Thr Val His Val Asp Arg Ile Ser Met Lys Arg
                245                 250                 255

Lys Ile Ile Ala Cys Ser Gly Cys Glu Ala Leu Val Asp Thr Gly
            260                 265                 270

Thr Ala Leu Ile Lys Gly Pro Arg Arg Leu Val Asn Asn Ile Gln Lys
            275                 280                 285

Leu Ile Gly Thr Thr Pro Arg Gly Ser Lys His Tyr Val Ser Cys Ser
        290                 295                 300

Val Val Asn Thr Leu Pro Ser Ile Ile Phe Thr Ile Asn Gly Ile Asn
305                 310                 315                 320

Tyr Pro Val Pro Ala Arg Ala Tyr Ile Leu Lys Asp Ser Glu Ser Asn
                325                 330                 335

Cys Tyr Thr Thr Phe Lys Glu Asn Thr Val Arg Thr Ser Arg Glu Thr
            340                 345                 350

Trp Ile Leu Gly Asp Val Phe Pro Arg Leu Tyr Phe Ser Val Phe Asp
        355                 360                 365

Arg Gly Asn Asp Arg Ile Gly Leu Ala Arg Ala Val
370                 375                 380

<210> SEQ ID NO 49
<211> LENGTH: 1158
<212> TYPE: DNA
<213> ORGANISM: bovidae

<400> SEQUENCE: 49

```
taggaaagaa gcatgaagtg gcttgtgctc ctcgggctgg tggccttctc agagtgcata      60
gtcaaaatac ctctaaggag agtgaagacc atgagaaaaa ccctcagtgg aaaaaacatc    120
ctgaacaatt tcctgaagga acatgcttac agactgtccc agatttcttc ttgtggctca    180
aatctaactt ttcaccccctt gagaaacatc aaggataggc tctacgtggg taacatcacc    240
attggaacac cccctcaaga attccaggtt atctttgaca caggctcatc tgacttgtgg    300
gtgacctccg tcttttgcac cagcccaacc tgttctacac atgttatgtt cagacatttt    360
gattcttcca cctccggcc taccaaaaag accttcagca tcaactacgg ttctggaagg    420
atgaaaggag ttgttgttca tgacacagtt cggattgggg accttgtaag tactgaccag    480
ccatttggtc taagtgtggt ggaacttggg tttgatggta taccttttga tggcgtcatg    540
ggcttgaact accccaaact atccttctct ggagccattc ccatctttga caacctgagg    600
aatcaaggtg ccatttctga gcctgttttt gccttctact tgagcaaaga cgagcaggag    660
ggcagtgtgg tgatgtttgg tggggtggac caccgctact acaagggaga gctcaactgg    720
ataccactga tccaagcagg cgactggagt gtacacatgg acagcatctc catgaaaaga    780
aaggttattg cttgctctgg tggctgcaag gccgttgtgg acaccgggac atcactgatt    840
gaaggcccaa gaagactggt caataacata cagaagctca tcagagccat gccacggggt    900
tccgagtact acgtttcatg ttctgcggtc aatacctgc ccctatat cttcaccatc    960
aaaggcatca actacccagt gccagctcaa gcctacatcc tcaaggattc tagaggccac   1020
tgctatacca cctttaaaga ggacagattg agtccaccat ctacagagac ctggatcctg   1080
ggtgacgtct tcctgaggcg gtatttctcg gtctttgatc gaggaaatga caggattggc   1140
```
ctggcacggg cagtgtaa                                              1158

<210> SEQ ID NO 50
<211> LENGTH: 381
<212> TYPE: PRT
<213> ORGANISM: bovidae

<400> SEQUENCE: 50

```
Met Lys Trp Leu Val Leu Leu Gly Leu Val Ala Phe Ser Glu Cys Ile
 1               5                  10                  15

Val Lys Ile Pro Leu Arg Arg Val Lys Thr Met Arg Lys Thr Leu Ser
            20                  25                  30

Gly Lys Asn Ile Leu Asn Asn Phe Leu Lys Glu His Ala Tyr Arg Leu
        35                  40                  45

Ser Gln Ile Ser Ser Cys Gly Ser Asn Leu Thr Phe His Pro Leu Arg
    50                  55                  60

Asn Ile Lys Asp Arg Leu Tyr Val Gly Asn Ile Thr Ile Gly Thr Pro
 65                  70                  75                  80

Pro Gln Glu Phe Gln Val Ile Phe Asp Thr Gly Ser Ser Asp Leu Trp
                85                  90                  95

Val Thr Ser Val Phe Cys Thr Ser Pro Thr Cys Ser Thr His Val Met
            100                 105                 110

Phe Arg His Phe Asp Ser Ser Thr Phe Arg Pro Thr Lys Lys Thr Phe
        115                 120                 125

Ser Ile Asn Tyr Gly Ser Gly Arg Met Lys Gly Val Val His Asp
    130                 135                 140

Thr Val Arg Ile Gly Asp Leu Val Ser Thr Asp Gln Pro Phe Gly Leu
145                 150                 155                 160

Ser Val Val Glu Leu Gly Phe Asp Gly Ile Pro Phe Asp Gly Val Met
                165                 170                 175

Gly Leu Asn Tyr Pro Lys Leu Ser Phe Ser Gly Ala Ile Pro Ile Phe
            180                 185                 190

Asp Asn Leu Arg Asn Gln Gly Ala Ile Ser Glu Pro Val Phe Ala Phe
        195                 200                 205

Tyr Leu Ser Lys Asp Glu Gln Glu Gly Ser Val Val Met Phe Gly Gly
    210                 215                 220

Val Asp His Arg Tyr Tyr Lys Gly Glu Leu Asn Trp Ile Pro Leu Ile
225                 230                 235                 240

Gln Ala Gly Asp Trp Ser Val His Met Asp Ser Ile Ser Met Lys Arg
                245                 250                 255

Lys Val Ile Ala Cys Ser Gly Gly Cys Lys Ala Val Val Asp Thr Gly
            260                 265                 270

Thr Ser Leu Ile Glu Gly Pro Arg Arg Leu Val Asn Asn Ile Gln Lys
        275                 280                 285

Leu Ile Arg Ala Met Pro Arg Gly Ser Glu Tyr Tyr Val Ser Cys Ser
    290                 295                 300

Ala Val Asn Thr Leu Pro Pro Ile Ile Phe Thr Ile Lys Gly Ile Asn
305                 310                 315                 320

Tyr Pro Val Pro Ala Gln Ala Tyr Ile Leu Lys Asp Ser Arg Gly His
                325                 330                 335

Cys Tyr Thr Thr Phe Lys Glu Asp Arg Leu Ser Pro Ser Thr Glu
            340                 345                 350

Thr Trp Ile Leu Gly Asp Val Phe Leu Arg Arg Tyr Phe Ser Val Phe
        355                 360                 365
```

Asp Arg Gly Asn Asp Arg Ile Gly Leu Ala Arg Ala Val
         370                 375                 380

<210> SEQ ID NO 51
<211> LENGTH: 1154
<212> TYPE: DNA
<213> ORGANISM: bovidae

<400> SEQUENCE: 51

| | | | | | |
|---|---|---|---|---|---|
| aggaaagaag | catgaagtgg | cttgtggtcc | tcggacttgt | ggccttctca | gagtgcatag | 60 |
| tcaaaatacc | tctaaggaga | gtgaagacca | tgagaaaagc | cctcagtgga | aaaaacatgc | 120 |
| tgaacaattt | cctgaaggaa | catgcttaca | gactgtccca | gatttctttt | cgtggctcaa | 180 |
| atctaactag | tcaccctgctg | agaaacatca | aggatttggt | ctacctggct | aatatcacca | 240 |
| ttggaacacc | ccctcaggag | ttccaggttt | tccttgacac | aggctcatct | gacttgtggg | 300 |
| tgccctctga | cttttgcacc | agcccaggct | gttctaaaca | cgttagattc | agacatcttc | 360 |
| agtcttccac | cttccggctt | accaataaga | ccttcagcat | cacctatgga | tctgggagaa | 420 |
| ttaaaggagt | tgttgctcat | gacacagttc | ggattgggga | ccttgtaagc | actgaccagc | 480 |
| cgttcagtct | aagcatggca | gaatacgggc | ttgagcatat | accttttgat | ggcatcttgg | 540 |
| gcttgaacta | ccccaacgta | tcttcttctg | gagcaatccc | tatctttgac | aagctgaaga | 600 |
| atcaaggtgc | catttctgaa | cctgtttttg | ccttctactt | gagcaaagac | aagcaggagg | 660 |
| gcagtgtggt | gatgtttggt | ggggtggacc | atcgctatta | caggggaaag | ctcaactggg | 720 |
| taccattgat | ccaagcggga | aactggatta | tacacatgga | cagcatctcc | attgaaagaa | 780 |
| aggttattgc | ttgttctgga | ggctgcgtgg | cctttgttga | catcgggaca | gcattcatcg | 840 |
| aaggcccaaa | accactggtc | gataacatgc | agaagctcat | cagggccaag | ccatggcgtt | 900 |
| ccaagcacta | tgtttcatgt | tctgcggtca | atacactgcc | ctctattacc | ttcaccatca | 960 |
| acggcatcaa | ctacccagtg | ccaggtcgag | cctacatcct | caaggattct | agacgccgtt | 1020 |
| gctatagcac | ctttaaagag | atcccattga | gtccaactac | agagttctgg | atgctgggtg | 1080 |
| acgtcttcct | gaggctgtat | ttctcagtct | ttgatcgagg | aaatgacagg | attgggctgg | 1140 |
| cacgggcagt | gtaa | | | | | 1154 |

<210> SEQ ID NO 52
<211> LENGTH: 380
<212> TYPE: PRT
<213> ORGANISM: bovidae

<400> SEQUENCE: 52

Met Lys Trp Leu Val Val Leu Gly Leu Val Ala Phe Ser Glu Cys Ile
 1               5                  10                  15

Val Lys Ile Pro Leu Arg Arg Val Lys Thr Met Arg Lys Ala Leu Ser
            20                  25                  30

Gly Lys Asn Met Leu Asn Asn Phe Leu Lys Glu His Ala Tyr Arg Leu
        35                  40                  45

Ser Gln Ile Ser Phe Arg Gly Ser Asn Leu Thr Ser His Pro Leu Arg
    50                  55                  60

Asn Ile Lys Asp Leu Val Tyr Leu Ala Asn Ile Thr Ile Gly Thr Pro
65                  70                  75                  80

Pro Gln Glu Phe Gln Val Phe Leu Asp Thr Gly Ser Ser Asp Leu Trp
                85                  90                  95

Val Pro Ser Asp Phe Cys Thr Ser Pro Gly Cys Ser Lys His Val Arg

```
                     100                 105                 110
        Phe Arg His Leu Gln Ser Ser Thr Phe Arg Leu Thr Asn Lys Thr Phe
                    115                 120                 125

Ser Ile Thr Tyr Gly Ser Gly Arg Ile Lys Gly Val Val Ala His Asp
                    130                 135                 140

Thr Val Arg Ile Gly Asp Leu Val Ser Thr Asp Gln Pro Phe Ser Leu
        145                 150                 155                 160

Ser Met Ala Glu Tyr Gly Leu Glu His Ile Pro Phe Asp Gly Ile Leu
                            165                 170                 175

Gly Leu Asn Tyr Pro Asn Val Ser Ser Gly Ala Ile Pro Ile Phe
                        180                 185                 190

Asp Lys Leu Lys Asn Gln Gly Ala Ile Ser Glu Pro Val Phe Ala Phe
                    195                 200                 205

Tyr Leu Ser Lys Asp Lys Gln Glu Gly Ser Val Val Met Phe Gly Gly
                    210                 215                 220

Val Asp His Arg Tyr Tyr Arg Gly Lys Leu Asn Trp Val Pro Leu Ile
        225                 230                 235                 240

Gln Ala Gly Asn Trp Ile Ile His Met Asp Ser Ile Ser Ile Glu Arg
                            245                 250                 255

Lys Val Ile Ala Cys Ser Gly Gly Cys Val Ala Phe Val Asp Ile Gly
                        260                 265                 270

Thr Ala Phe Ile Glu Gly Pro Lys Pro Leu Val Asp Asn Met Gln Lys
                    275                 280                 285

Leu Ile Arg Ala Lys Pro Trp Arg Ser Lys His Tyr Val Ser Cys Ser
                    290                 295                 300

Ala Val Asn Thr Leu Pro Ser Ile Thr Phe Thr Ile Asn Gly Ile Asn
        305                 310                 315                 320

Tyr Pro Val Pro Gly Arg Ala Tyr Ile Leu Lys Asp Ser Arg Arg Arg
                            325                 330                 335

Cys Tyr Ser Thr Phe Lys Glu Ile Pro Leu Ser Pro Thr Thr Glu Phe
                        340                 345                 350

Trp Met Leu Gly Asp Val Phe Leu Arg Leu Tyr Phe Ser Val Phe Asp
                    355                 360                 365

Arg Gly Asn Asp Arg Ile Gly Leu Ala Arg Ala Val
                    370                 375                 380

<210> SEQ ID NO 53
<211> LENGTH: 1154
<212> TYPE: DNA
<213> ORGANISM: bovidae

<400> SEQUENCE: 53
aggaaagaag catgaagtgg cttgtgctcc tcggtctggt ggccttctca gagtgcatat      60 tcaaatacc tctaaggaga gtgaagacca tgagaaaaac cctcagtgga aaaaacatgc     120
tgaacaattt cctgaaggag catccttaca aactgtccca gatttctttt cgtggctcaa    180
atctaaccac tctcccactg aggaacatct gggatatatt ctacataggt accatcacca    240
ttggaacacc ccctcaggaa ttccaggttg tctttgacac agcctcatct gacttgtggg    300
tgccctccat catttgcaac agctcaacct gttctacaca cgttagattc agacatcgtc    360
agtcttccac cttccggctt accaataaga cgttcgggat cacgtatgga tctgggagaa    420
tgaaaggagt tgttgttcat gacacagttc ggattgggga ccttgtaagt actgaccagc    480
cattcggtct aagcgtggcg gaatacgggt ttgagggcag aagatttgat ggtgtcttgg    540
```

-continued

```
gcttgaacta ccccaacata tccttctcta aagccatccc catctttgat aagctgaaga    600
atgaaggtgc catttcagag cctgttttg ccttctactt gagcaaagac aagcagaagg    660
gcagtgtggt gatgtttggt ggggtggacc accgctacta caaggagag ctcaactggg    720
taccattgat ccgagcgggt gactggagtg tacacgtaga ccgcatcacc atgaaaggag    780
aggttattgg ttgttctgat ggctgcacgg ccatggtgga caccgggtca tcaaatatcc    840
aaggcccagg aagagtgatc gataacatac acaagctcat tggtgccaca ccacgggtt    900
ccaagcacta cgtttcatgt tctgcggtca gtgctctgcc ctctgttgtc ttcaccatca    960
atggcatcaa ctacccagtg ccagctcgag cctacgtcct caaggatttt acaggcaact   1020
gctacaccac ctttaaagag aaaagggtaa ggagatctac ggagttctgg atcctgggtg   1080
aagccttcct gaggctgtat ttctcggtct ttgatcgagg aaatgacagg attggcctgg   1140
cacgggcagt gtaa                                                    1154
```

<210> SEQ ID NO 54
<211> LENGTH: 380
<212> TYPE: PRT
<213> ORGANISM: bovidae

<400> SEQUENCE: 54

```
Met Lys Trp Leu Val Leu Leu Gly Leu Val Ala Phe Ser Glu Cys Ile
  1               5                  10                  15

Phe Lys Ile Pro Leu Arg Arg Val Lys Thr Met Arg Lys Thr Leu Ser
             20                  25                  30

Gly Lys Asn Met Leu Asn Asn Phe Leu Lys Glu His Pro Tyr Lys Leu
         35                  40                  45

Ser Gln Ile Ser Phe Arg Gly Ser Asn Leu Thr Thr Leu Pro Leu Arg
     50                  55                  60

Asn Ile Trp Asp Ile Phe Tyr Ile Gly Thr Ile Thr Ile Gly Thr Pro
 65                  70                  75                  80

Pro Gln Glu Phe Gln Val Val Phe Asp Thr Ala Ser Ser Asp Leu Trp
                 85                  90                  95

Val Pro Ser Ile Ile Cys Asn Ser Ser Thr Cys Ser Thr His Val Arg
            100                 105                 110

Phe Arg His Arg Gln Ser Ser Thr Phe Arg Leu Thr Asn Lys Thr Phe
        115                 120                 125

Gly Ile Thr Tyr Gly Ser Gly Arg Met Lys Gly Val Val His Asp
    130                 135                 140

Thr Val Arg Ile Gly Asp Leu Val Ser Thr Asp Gln Pro Phe Gly Leu
145                 150                 155                 160

Ser Val Ala Glu Tyr Gly Phe Glu Gly Arg Arg Phe Asp Gly Val Leu
                165                 170                 175

Gly Leu Asn Tyr Pro Asn Ile Ser Phe Ser Lys Ala Ile Pro Ile Phe
            180                 185                 190

Asp Lys Leu Lys Asn Glu Gly Ala Ile Ser Glu Pro Val Phe Ala Phe
        195                 200                 205

Tyr Leu Ser Lys Asp Lys Gln Lys Gly Ser Val Val Met Phe Gly Gly
    210                 215                 220

Val Asp His Arg Tyr Tyr Lys Gly Glu Leu Asn Trp Val Pro Leu Ile
225                 230                 235                 240

Arg Ala Gly Asp Trp Ser Val His Val Asp Arg Ile Thr Met Lys Gly
                245                 250                 255

Glu Val Ile Gly Cys Ser Asp Gly Cys Thr Ala Met Val Asp Thr Gly
```

```
                260             265             270
Ser Ser Asn Ile Gln Gly Pro Gly Arg Val Ile Asp Asn Ile His Lys
            275             280             285
Leu Ile Gly Ala Thr Pro Arg Gly Ser Lys His Tyr Val Ser Cys Ser
        290             295             300
Ala Val Ser Ala Leu Pro Ser Val Val Phe Thr Ile Asn Gly Ile Asn
305             310             315             320
Tyr Pro Val Pro Ala Arg Ala Tyr Val Leu Lys Asp Phe Thr Gly Asn
                325             330             335
Cys Tyr Thr Thr Phe Lys Glu Lys Arg Val Arg Arg Ser Thr Glu Phe
            340             345             350
Trp Ile Leu Gly Glu Ala Phe Leu Arg Leu Tyr Phe Ser Val Phe Asp
        355             360             365
Arg Gly Asn Asp Arg Ile Gly Leu Ala Arg Ala Val
370             375             380
```

<210> SEQ ID NO 55
<211> LENGTH: 1320
<212> TYPE: DNA
<213> ORGANISM: bovidae

<400> SEQUENCE: 55

```
gtcgacggaa agaagcatga agtgggttgt gctccttggg ctggtggcct tctcagagtg      60
catagtcaaa atacctctaa ggcgagtgaa gaccatgaga aaaaccctca gtggtaaaaa     120
catgctgaac aatttcttga aggagcatgg taacagattg tccaagattt cttttcgtgg     180
ctcaaatcta actactctcc cgctgagaaa catcgaggat ttgatgtacg tgggtaacat     240
caccattgga acacccccac aggaattcca ggttgtcttt gatacaggct catctgactt     300
ttgggtgccc tccgactttt gcactagtcc agactgtatt acacacgtta gattcagaca     360
acatcagtct tccaccttcc ggcctaccaa taagaccttc agcatcacct atggatctgg     420
gagaatgaga ggagttgttg ttcatgacac agttcggatt ggggaccttg taagtactga     480
ccagccgttc ggtctaagcg tgtcagaata cgggtttaag gacagagctt atgatggcat     540
cctgggcttg aactaccccg acgaatcctt ctctgaagcc atccccatct tgacaagct      600
aaagaatgaa ggtgccattt ctgagcctat ttttgccttc tacttgagca aaaaaaagcg     660
ggagggcagt gtggtgatgt tggtgggt ggaccaccgc tactacaagg gagagctcaa       720
ctgggtacca ttgatcgaag agggtgactg gagtgtacgc atggacggca tctccatgaa     780
aacaaaggta gttgcttgtt ctgacggctg cgaggctgtt gttgacactg ggacatcact     840
gataaaaggc ccaagaaaac tggtcaataa aatacgaag ctcattggtg ccacgccacg      900
gggttccaag cactacgttt attgttctgc ggtcaatgct ctgccctcta ttatcttcac     960
catcaatggc atcaactacc cagtgccagc tcgagcctac attctcaagg attctagagg    1020
ccgctgctat accgccttta aaaagcaacg attcagttca tctacagaga cctggctcct    1080
gggtgacgcc ttcctgaggg tgtatttctc ggtctttgat cgaggaaatg caggattgg     1140
cctggcacag gcagtgtaaa tgcttggagt ggttcaagaa tcagtaaggc cgcttntaac    1200
acacactcac tcacactagg gcactcctgc ccaggatggt ggtgaactgt atttggtggt    1260
ctgtacaccc tattctcagt gaagaataaa cggtttcact cttaatggtg ctgaaaaaaa    1320
```

<210> SEQ ID NO 56
<211> LENGTH: 380
<212> TYPE: PRT

<213> ORGANISM: bovidae

<400> SEQUENCE: 56

```
Met Lys Trp Val Val Leu Leu Gly Leu Val Ala Phe Ser Glu Cys Ile
  1               5                  10                  15
Val Lys Ile Pro Leu Arg Arg Val Lys Thr Met Arg Lys Thr Leu Ser
                 20                  25                  30
Gly Lys Asn Met Leu Asn Asn Phe Leu Lys Glu His Gly Asn Arg Leu
             35                  40                  45
Ser Lys Ile Ser Phe Arg Gly Ser Asn Leu Thr Thr Leu Pro Leu Arg
         50                  55                  60
Asn Ile Glu Asp Leu Met Tyr Val Gly Asn Ile Thr Ile Gly Thr Pro
 65                  70                  75                  80
Pro Gln Glu Phe Gln Val Val Phe Asp Thr Gly Ser Ser Asp Phe Trp
                 85                  90                  95
Val Pro Ser Asp Phe Cys Thr Ser Pro Asp Cys Ile Thr His Val Arg
                100                 105                 110
Phe Arg Gln His Gln Ser Ser Thr Phe Arg Pro Thr Asn Lys Thr Phe
            115                 120                 125
Ser Ile Thr Tyr Gly Ser Gly Arg Met Arg Gly Val Val His Asp
        130                 135                 140
Thr Val Arg Ile Gly Asp Leu Val Ser Thr Asp Gln Pro Phe Gly Leu
145                 150                 155                 160
Ser Val Ser Glu Tyr Gly Phe Lys Asp Arg Ala Tyr Asp Gly Ile Leu
                165                 170                 175
Gly Leu Asn Tyr Pro Asp Glu Ser Phe Ser Glu Ala Ile Pro Ile Phe
            180                 185                 190
Asp Lys Leu Lys Asn Glu Gly Ala Ile Ser Glu Pro Ile Phe Ala Phe
        195                 200                 205
Tyr Leu Ser Lys Lys Arg Glu Gly Ser Val Val Met Phe Gly Gly
        210                 215                 220
Val Asp His Arg Tyr Tyr Lys Gly Glu Leu Asn Trp Val Pro Leu Ile
225                 230                 235                 240
Glu Glu Gly Asp Trp Ser Val Arg Met Asp Gly Ile Ser Met Lys Thr
                245                 250                 255
Lys Val Val Ala Cys Ser Asp Gly Cys Glu Ala Val Val Asp Thr Gly
                260                 265                 270
Thr Ser Leu Ile Lys Gly Pro Arg Lys Leu Val Asn Lys Ile Gln Lys
        275                 280                 285
Leu Ile Gly Ala Thr Pro Arg Gly Ser Lys His Tyr Val Tyr Cys Ser
        290                 295                 300
Ala Val Asn Ala Leu Pro Ser Ile Ile Phe Thr Ile Asn Gly Ile Asn
305                 310                 315                 320
Tyr Pro Val Pro Ala Arg Ala Tyr Ile Leu Lys Asp Ser Arg Gly Arg
                325                 330                 335
Cys Tyr Thr Ala Phe Lys Lys Gln Arg Phe Ser Ser Ser Thr Glu Thr
                340                 345                 350
Trp Leu Leu Gly Asp Ala Phe Leu Arg Val Tyr Phe Ser Val Phe Asp
            355                 360                 365
Arg Gly Asn Gly Arg Ile Gly Leu Ala Gln Ala Val
        370                 375                 380
```